(12) United States Patent
Hames et al.

(10) Patent No.: US 8,489,340 B2
(45) Date of Patent: Jul. 16, 2013

(54) METHOD FOR PREDICTING THE AMOUNT OF ACCESSIBLE CARBOHYDRATE IN A FEEDSTOCK SAMPLE USING A NEAR-INFRARED MODEL

(75) Inventors: Bonnie Hames, Newbury Park, CA (US); Tanya Kruse, Winnetka, CA (US); Steven R. Thomas, Wheat Ridge, CO (US); Amr Saad Ragab, Blacksburg, VA (US)

(73) Assignee: Ceres, Inc., Thousand Oaks, CA (US)

( * ) Notice: Subject to any disclaimer, the term of this patent is extended or adjusted under 35 U.S.C. 154(b) by 107 days.

(21) Appl. No.: 12/740,941

(22) PCT Filed: Oct. 31, 2008

(86) PCT No.: PCT/US2008/082047
§ 371 (c)(1),
(2), (4) Date: Dec. 8, 2010

(87) PCT Pub. No.: WO2009/059176
PCT Pub. Date: May 7, 2009

(65) Prior Publication Data
US 2011/0087470 A1    Apr. 14, 2011

Related U.S. Application Data

(60) Provisional application No. 61/056,631, filed on May 28, 2008, provisional application No. 61/025,033, filed on Jan. 31, 2008, provisional application No. 60/984,976, filed on Nov. 2, 2007.

(51) Int. Cl.
*G01N 31/00* (2006.01)

(52) U.S. Cl.
USPC .......................................................... 702/28

(58) Field of Classification Search
None
See application file for complete search history.

(56) References Cited

U.S. PATENT DOCUMENTS

| | | | |
|---|---|---|---|
| 4,982,027 A | 1/1991 | Korff et al. | |
| 5,499,095 A | 3/1996 | Gast et al. | |
| 5,766,847 A | 6/1998 | Jackle et al. | |
| 5,874,274 A | 2/1999 | Jakobsen et al. | |
| 5,878,215 A | 3/1999 | Kling et al. | |
| 6,090,595 A | 7/2000 | Foody et al. | |
| 6,137,108 A | 10/2000 | DeThomas et al. | |
| 6,333,181 B1 | 12/2001 | Ingram et al. | |
| 6,483,583 B1 | 11/2002 | Wright et al. | |
| 7,059,993 B2 | 6/2006 | Ding et al. | |
| 7,112,429 B2 | 9/2006 | Ding et al. | |
| 7,285,402 B2 | 10/2007 | Gaddy et al. | |
| 2003/0092097 A1 | 5/2003 | Andersen et al. | |
| 2007/0092935 A1 | 4/2007 | Jones et al. | |
| 2007/0275447 A1 | 11/2007 | Lewis et al. | |
| 2008/0057554 A1 | 3/2008 | Huhnke et al. | |

FOREIGN PATENT DOCUMENTS

| | | |
|---|---|---|
| CN | 1888860 A | 1/2007 |
| EP | 0 534 858 | 3/1993 |
| EP | 1 894 461 | 3/2008 |

OTHER PUBLICATIONS

Ehrman (Handbook on Bioethanol: Production and Utilization, 1996, Ch. 18, p. 395-415).*
Ye et al. (ASABE Annual International Meeting, Jul. 2006, pp. 1-10).*
Lanza et al. (Journal of Food Science, vol. 49, Issue 4, pp. 995-998, Jul. 1984).*
Waldon et al. (Appl Microbiol Biotechnol, 1986, 24:487-492).*
EPOBIO (Cell Wall Saccharification, Nov. 2006, p. 1-69).*
International Preliminary Report on Patentability in PCT/US2008/082047 mailed May 4, 2010, 34 pages.
International Search Report in PCT/US2008/082047 mailed Jul. 2, 2009, 26 pages.
Alonso-Blanco et al., "The use of recombinant inbred lines (RILs) for genetic mapping," In Methods in Molecular Biology (J.M. Martinez-Zapater and J. Salinas, Humana Press, Totowa, NJ., 1998), 82: 137-146.
ASTM International, "Standard test method for ash in biomass," Designation E1755-01, 2007, 3 pages.
ASTM International, "Standard test method for determination of acid-insoluble residue in biomass," Designation: E1721-01, 2009, 3 pages.
ASTM International, "Standard test method for determination of carbohydrates in biomass by high performance liquid chromatography," Designation: E1758-01, 2007, 5 pages.
Burr et al., "Gene mapping with recombinant inbreds in maize," *Genetics*, 1988, 118: 519-526.
Burr et al., "Mapping Genes with Recombinant Inbreds," In Freeling and Walbot (Ed.), *The Maize Handbook*, (New York, Springer-Verlag, 1994), pp. 249-254.
Chemical variation in mature corn stover cell walls' [online]. American Society of Plant Biologists, 2002 [retrieved on Dec. 16, 2010]. Retrieved from the Internet: <URL: http://abstracts.aspb.org/pb2002/public/P44/0025.html>, 1 page.
Datar et al., "Fermentation of biomass-generated producer gas to ethanol," *Biotechnology and Bioengineering*, 2004, 86(5): 587-594.
Gab et al., "NIR spectroscopic investigation of foliage of ozone-stressed *Fagus sylvatica* trees," *Journal of Forest Research*, 2006, 11(2): 69-75.
Gardiner et al., "Development of a core RFLP map in maize using an immortalized F2 population," *Genetics*, 1993, 134: 917-930.

(Continued)

*Primary Examiner* — Pablo S Whaley
(74) *Attorney, Agent, or Firm* — Fish & Richardson P.C.

(57) ABSTRACT

The present invention is directed to a method of using a near-infrared (NIR) model to predict the amount of accessible carbohydrate material in a feedstock sample. The NIR model is generated by subjecting a set of biomass calibration feedstock samples to near infrared spectroscopy which produces NIR spectroscopic data, measuring the chemical compositions of each said calibration feedstock sample by wet chemical techniques, and measuring the total amount of monosaccharides and disaccharides solubilized by each said calibration feedstock sample after processing under a defined pretreatment condition or defined enzyme load condition. The method is then applied to NIR spectral data obtained from a test feedstock sample to predict the amount of accessible carbohydrate material in the test feedstock sample.

15 Claims, 19 Drawing Sheets

OTHER PUBLICATIONS

Geladi and Kowalski, "Partial least-squares regression: A tutorial," *Analytica Chimica Acta*, 1986, 185:1-17.

Hames et al., "Determination of protein content in biomass: Laboratory analytical procedure (LAP)," *National Renewable Energy Laboratory (NREL)*, 2008, 8 pages.

Hames et al., "Rapid Biomass analysis: New analytical methods supporting fuels and chemical production from biomass," *Abstracts of Papers American Chemical Society*, 2002, 223 (1-2): 130.

Hames, "Rapid biomass analysis: New tools for compositional analysis of corn stover feed stocks and process intermediates from ethanol production," *Applied Biochemistry and Biotechnology*, 2003, 105-108: 5-16.

Hoskuldsson, "PLS regression methods," *J. Chemometrics*, 1988, 2:211-228.

Narra et al., "Total nonstructural carbohydrate assessment in creeping bentgrass at different mowing heights," *Crop Science*, 2004, 44(3): 908-913.

Pordesimo et al., "Variation in corn stover composition and energy content with crop maturity," *Biomass and Bioenergy*, 2005, 28(4): 366-374.

Refseth et al., "Hybridization capture of microsatellites directly from genomic DNA" *Electrophoresis*, 18:1519-1523 (1997).

Sanderson et al., "Compositional analysis of biomass feedstocks by near infrared reflectance spectroscopy," *Biomass and Bioenergy*, 1996, 11(5): 365-370.

Saulinier et al., "Isolation and Partial Characterization of feruloylated oligosaccharides from maize bran," *Carbohydrate Research*, 1995, 272: 241-253.

Sluiter et al., "Determination of structural carbohydrates and lignin in biomass," NREL/TP-510-42618, Apr. 2008, National Renewable Energy Laboratory, Golden, Colorado.

Sohn, "Near infrared analysis of ground barley for use as a feedstock for fuel ethanol production," *Applied Spectroscopy*, 2007, 61(11): 1178-1183.

Vogel and Jung, "Genetic modification of herbaceous plants for feed and fuel," *Critical Rev. Plant Sci.*, 2001, 20(1):15-49.

Werpy and Petersen "Top Value Added Chemicals from Biomass: vol. 1—Results of screening for potential candidates from sugars and synthesis gas" U.S. Dept. of Energy, NREL, PNNL-14808, 2004, 76 pages.

Wold S. et al., "Principal component analysis," *Chemometrics Intelligent Laboratory Systems*, 1987, 2:37-52.

Ye et al., "Fast classification and compositional analysis of cornstover fractions using Fourier transform near-infrared techniques," *ScienceDirect*, 2008, 99: 7323-7332.

Xinqin Feng, Agent, The Patent Office of the People's Republic of China, Chinese Office Action, CN Application 200880123038.0, issued Sep. 28, 2011, 7 pages.

\* cited by examiner

| Constituent Name: Protein | | | Equation:PLS | | | | | | |
|---|---|---|---|---|---|---|---|---|---|
| Scatter:NSVD | | | Regression: Modified PLS | | | | | | |
| Number of Terms 3 | | | | | | | | | |
| Segment 1 408-1092 | | | Segment 8 | | | | | | |
| Segment2: 1108 - 2492 | | | Segment 8 | | | | | | |
| | Loading Coefficients | | | | | | | | |
| Concentration Coefficients | PC1 | PC2 | PC3 | Data point | Wavelength | Derivative | Segment | Block | Polynomial |
| -0.9491 | 0298289 | -0.2268181 | 0.4724126 | 5 | 408 | 1 | 4 | 4 | 1 |
| -0.1527 | 2797483 | -0.0474248 | 0.0300819 | 9 | 416 | 1 | 4 | 4 | 1 |
| -1.2402 | 3189894 | 0.0633619 | -0.1565211 | 13 | 424 | 1 | 4 | 4 | 1 |
| 0.0631 | 3086548 | 0.204904 | -0.3019251 | 17 | 432 | 1 | 4 | 4 | 1 |
| -0.4006 | 2525997 | 0.2986068 | -0.4439142 | 21 | 440 | 1 | 4 | 4 | 1 |
| -0.0416 | 1647938 | 0.3611889 | -0.5910953 | 25 | 448 | 1 | 4 | 4 | 1 |
| -0.0158 | 0657302 | 0.3839316 | -0.6891987 | 29 | 456 | 1 | 4 | 4 | 1 |
| -0.4483 | 0222351 | 0.4014674 | -0.7127866 | 33 | 464 | 1 | 4 | 4 | 1 |
| 0.0923 | 0830106 | 0.4244998 | -0.6678132 | 37 | 472 | 1 | 4 | 4 | 1 |
| -0.1819 | 1161762 | 0.4379519 | -0.6112673 | 41 | 480 | 1 | 4 | 4 | 1 |
| -0.4734 | 0976522 | 0.417154 | -0.5502027 | 45 | 488 | 1 | 4 | 4 | 1 |
| 0.0111 | 0166539 | 0.3671316 | -0.4848528 | 49 | 496 | 1 | 4 | 4 | 1 |
| 0.4829 | 0886453 | 0.2621567 | -0.3603398 | 53 | 504 | 1 | 4 | 4 | 1 |
| 0.5978 | 1669909 | 0.1389464 | -0.2294191 | 57 | 512 | 1 | 4 | 4 | 1 |
| -0.2536 | 1915192 | 0.0251486 | -0.1357904 | 61 | 520 | 1 | 4 | 4 | 1 |
| -1.2585 | 1719448 | -0.0734455 | -0.0957339 | 65 | 528 | 1 | 4 | 4 | 1 |
| -1.5422 | 1461509 | -0.1020104 | -0.1032614 | 69 | 536 | 1 | 4 | 4 | 1 |
| -1.9759 | 1323145 | -0.0595756 | -0.112226 | 73 | 544 | 1 | 4 | 4 | 1 |
| -2.0429 | 0.12211 | -0.0558964 | -0.1007662 | 77 | 552 | 1 | 4 | 4 | 1 |
| -2.2672 | 1260177 | -0.1083809 | -0.0776803 | 81 | 560 | 1 | 4 | 4 | 1 |
| -1.921 | 1461328 | -0.1610869 | -0.0470461 | 85 | 568 | 1 | 4 | 4 | 1 |
| -1.225 | 1548374 | -0.2047525 | 0.0065508 | 89 | 576 | 1 | 4 | 4 | 1 |
| -0.3841 | 1424392 | -0.2450112 | 0.0609974 | 93 | 584 | 1 | 4 | 4 | 1 |
| 0.2356 | 1180658 | -0.2716325 | 0.0991446 | 97 | 592 | 1 | 4 | 4 | 1 |
| 0.9637 | 0935725 | -0.2699188 | 0.1154241 | 101 | 600 | 1 | 4 | 4 | 1 |
| 1.1831 | 0712909 | -0.2194149 | 0.106214 | 105 | 608 | 1 | 4 | 4 | 1 |
| 1.3446 | 0487492 | -0.1487638 | 0.0890747 | 109 | 616 | 1 | 4 | 4 | 1 |
| 1.2116 | 0140323 | -0.138018 | 0.0867819 | 113 | 624 | 1 | 4 | 4 | 1 |
| 0.748 | 0461735 | -0.2438653 | 0.0772413 | 117 | 632 | 1 | 4 | 4 | 1 |
| 0.7031 | 0961742 | -0.4010255 | 0.0906111 | 121 | 640 | 1 | 4 | 4 | 1 |
| 0.4567 | 0652106 | -0.438279 | 0.2008534 | 125 | 648 | 1 | 4 | 4 | 1 |
| 0.5702 | 0355418 | -0.4113469 | 0.3015277 | 129 | 656 | 1 | 4 | 4 | 1 |
| 1.1499 | 0623678 | -0.3144462 | 0.2200452 | 133 | 664 | 1 | 4 | 4 | 1 |
| 2.0011 | .028066 | 0.1142587 | -0.0990094 | 137 | 672 | 1 | 4 | 4 | 1 |
| 1.6945 | 2236402 | 0.5643604 | -0.2395304 | 141 | 680 | 1 | 4 | 4 | 1 |
| 0.0977 | 2666233 | 0.5750148 | 0.0618667 | 145 | 688 | 1 | 4 | 4 | 1 |
| 0.4581 | 1029303 | 0.3843774 | 0.366539 | 149 | 696 | 1 | 4 | 4 | 1 |
| 1.9146 | 049501 | 0.2633675 | 0.5019444 | 153 | 704 | 1 | 4 | 4 | 1 |
| 2.2326 | 1039189 | 0.1555958 | 0.4694388 | 157 | 712 | 1 | 4 | 4 | 1 |
| 2.0982 | 1085475 | 0.0683544 | 0.3513496 | 161 | 720 | 1 | 4 | 4 | 1 |
| 2.5034 | 1067774 | 0.02683 | 0.2681375 | 165 | 728 | 1 | 4 | 4 | 1 |

FIGURE 2A

| | | | | | | | | | |
|---|---|---|---|---|---|---|---|---|---|
| 2.8199 | 1019523 | 0.0065758 | 0.2053909 | 169 | 736 | 1 | 4 | 4 | 1 |
| 2.6745 | .09427 | -0.0059185 | 0.1405898 | 173 | 744 | 1 | 4 | 4 | 1 |
| 1.9878 | 0872397 | -0.009921 | 0.092575 | 177 | 752 | 1 | 4 | 4 | 1 |
| 1.3739 | 0807018 | -0.0052382 | 0.0677451 | 181 | 760 | 1 | 4 | 4 | 1 |
| 1.3333 | 0777523 | -0.0010198 | 0.0512533 | 185 | 768 | 1 | 4 | 4 | 1 |
| 1.6606 | 0779681 | -0.0021209 | 0.0318117 | 189 | 776 | 1 | 4 | 4 | 1 |
| 0.7324 | 0767962 | -0.004291 | 0.0123137 | 193 | 784 | 1 | 4 | 4 | 1 |
| 0.1708 | 075528 | -0.0057157 | -0.0016204 | 197 | 792 | 1 | 4 | 4 | 1 |
| 0.1744 | 0.0726 | -0.0065159 | -0.0120794 | 201 | 800 | 1 | 4 | 4 | 1 |
| -0.3166 | 0695227 | -0.0068202 | -0.0185115 | 205 | 808 | 1 | 4 | 4 | 1 |
| -0.5496 | 066195 | -0.0066382 | -0.0226552 | 209 | 816 | 1 | 4 | 4 | 1 |
| -0.8315 | 0611415 | -0.006409 | -0.0271551 | 213 | 824 | 1 | 4 | 4 | 1 |
| -0.5432 | 0563414 | -0.0057566 | -0.0314391 | 217 | 832 | 1 | 4 | 4 | 1 |
| -0.6775 | 0519972 | -0.0064194 | -0.0347483 | 221 | 840 | 1 | 4 | 4 | 1 |
| -0.8205 | 0487205 | -0.0071523 | -0.0381124 | 225 | 848 | 1 | 4 | 4 | 1 |
| -0.9192 | 0467818 | -0.0083626 | -0.0410311 | 229 | 856 | 1 | 4 | 4 | 1 |
| -0.9728 | 0443748 | -0.0104905 | -0.0422615 | 233 | 864 | 1 | 4 | 4 | 1 |
| -1.1779 | 0438229 | -0.0129833 | -0.0438376 | 237 | 872 | 1 | 4 | 4 | 1 |
| -1.2342 | 044959 | -0.015538 | -0.0442278 | 241 | 880 | 1 | 4 | 4 | 1 |
| -1.1637 | 0458128 | -0.0184223 | -0.0447334 | 245 | 888 | 1 | 4 | 4 | 1 |
| -1.1558 | 0448685 | -0.0209269 | -0.0455889 | 249 | 896 | 1 | 4 | 4 | 1 |
| -1.2248 | 0411451 | -0.0191387 | -0.0488943 | 253 | 904 | 1 | 4 | 4 | 1 |
| -1.4622 | 0316038 | -0.0126967 | -0.0541815 | 257 | 912 | 1 | 4 | 4 | 1 |
| -1.7447 | 0203553 | -0.0040466 | -0.0596027 | 261 | 920 | 1 | 4 | 4 | 1 |
| -1.7221 | 014654 | 0.0018769 | -0.0634794 | 265 | 928 | 1 | 4 | 4 | 1 |
| -1.5183 | 0138816 | 0.0027397 | -0.0636183 | 269 | 936 | 1 | 4 | 4 | 1 |
| -1.4113 | 0183508 | -0.0003699 | -0.0607394 | 273 | 944 | 1 | 4 | 4 | 1 |
| -1.2008 | 0297463 | -0.005696 | -0.0565986 | 277 | 952 | 1 | 4 | 4 | 1 |
| -0.7625 | 0452878 | -0.0196933 | -0.048561 | 281 | 960 | 1 | 4 | 4 | 1 |
| -0.4977 | 059251 | -0.0434015 | -0.036861 | 285 | 968 | 1 | 4 | 4 | 1 |
| -0.5079 | 0514129 | -0.0489869 | -0.033235 | 289 | 976 | 1 | 4 | 4 | 1 |
| -0.9927 | 0177175 | -0.0195416 | -0.0455457 | 293 | 984 | 1 | 4 | 4 | 1 |
| -1.3616 | 0057094 | -0.0055916 | -0.0559383 | 297 | 992 | 1 | 4 | 4 | 1 |
| -1.5325 | 0198612 | -0.0027406 | -0.0623553 | 301 | 1000 | 1 | 4 | 4 | 1 |
| -1.5479 | 0313788 | 0.0051454 | -0.0695467 | 305 | 1008 | 1 | 4 | 4 | 1 |
| -1.6904 | 0395028 | 0.0124443 | -0.0753072 | 309 | 1016 | 1 | 4 | 4 | 1 |
| -1.6812 | .045687 | 0.0172638 | -0.0784585 | 313 | 1024 | 1 | 4 | 4 | 1 |
| -1.5483 | 0491985 | 0.0199021 | -0.0798416 | 317 | 1032 | 1 | 4 | 4 | 1 |
| -1.4066 | 0499585 | 0.021406 | -0.080727 | 321 | 1040 | 1 | 4 | 4 | 1 |
| -1.3251 | 0503685 | 0.0227752 | -0.0807964 | 325 | 1048 | 1 | 4 | 4 | 1 |
| -1.2936 | 0522987 | 0.0234987 | -0.0806451 | 329 | 1056 | 1 | 4 | 4 | 1 |
| -1.3316 | 0556884 | 0.0239591 | -0.0807981 | 333 | 1064 | 1 | 4 | 4 | 1 |
| -1.2151 | 0586985 | 0.0237557 | -0.080083 | 337 | 1072 | 1 | 4 | 4 | 1 |
| -1.0836 | 0606114 | 0.0251248 | -0.0805719 | 341 | 1080 | 1 | 4 | 4 | 1 |
| -0.9036 | .061297 | 0.027247 | -0.0814273 | 345 | 1088 | 1 | 4 | 4 | 1 |
| -1.2982 | 0625755 | 0.0074961 | -0.040613 | 355 | 1108 | 1 | 4 | 4 | 1 |
| -0.1505 | 0981438 | 0.0392831 | -0.0729907 | 359 | 1116 | 1 | 4 | 4 | 1 |
| 0.9801 | 1266927 | 0.0620493 | -0.0889237 | 363 | 1124 | 1 | 4 | 4 | 1 |
| 1.63 | 132253 | 0.055532 | -0.0713364 | 367 | 1132 | 1 | 4 | 4 | 1 |
| 1.4198 | 1264827 | 0.037009 | -0.04339 | 371 | 1140 | 1 | 4 | 4 | 1 |
| 1.4866 | 1415472 | 0.0386029 | -0.0341621 | 375 | 1148 | 1 | 4 | 4 | 1 |

FIGURE 2B

| | | | | | | | | | |
|---|---|---|---|---|---|---|---|---|---|
| 1.492 | 1399466 | 0.0159145 | -0.0152278 | 379 | 1156 | 1 | 4 | 4 | 1 |
| 0.8254 | 1130491 | -0.0240164 | 0.0107612 | 383 | 1164 | 1 | 4 | 4 | 1 |
| 0.2563 | 0968584 | -0.051528 | 0.0215443 | 387 | 1172 | 1 | 4 | 4 | 1 |
| 0.6434 | 0934167 | -0.0476326 | -0.0003821 | 391 | 1180 | 1 | 4 | 4 | 1 |
| 0.9558 | 0866028 | -0.0261261 | -0.0229418 | 395 | 1188 | 1 | 4 | 4 | 1 |
| 0.7258 | 0614387 | 0.0168786 | -0.0332744 | 399 | 1196 | 1 | 4 | 4 | 1 |
| 0.3704 | 042349 | 0.0592296 | -0.0563424 | 403 | 1204 | 1 | 4 | 4 | 1 |
| 0.1601 | 0342253 | 0.0770434 | -0.060578 | 407 | 1212 | 1 | 4 | 4 | 1 |
| 0.2821 | 0253471 | 0.0574134 | -0.0351952 | 411 | 1220 | 1 | 4 | 4 | 1 |
| 0.1069 | 0130307 | 0.0230549 | -0.0081342 | 415 | 1228 | 1 | 4 | 4 | 1 |
| -0.795 | 0069837 | -0.010187 | 0.0119636 | 419 | 1236 | 1 | 4 | 4 | 1 |
| -0.4807 | 0081111 | -0.0217149 | 0.0212737 | 423 | 1244 | 1 | 4 | 4 | 1 |
| -0.3524 | 0105909 | -0.0168778 | 0.0199868 | 427 | 1252 | 1 | 4 | 4 | 1 |
| -0.1328 | 0127645 | -0.0065866 | 0.0111371 | 431 | 1260 | 1 | 4 | 4 | 1 |
| 0.1625 | 0087689 | 0.0014911 | 0.0062663 | 435 | 1268 | 1 | 4 | 4 | 1 |
| 0.0851 | .002427 | 0.0003595 | 0.0106478 | 439 | 1276 | 1 | 4 | 4 | 1 |
| -0.1717 | 0069893 | 0.0044472 | 0.0103912 | 443 | 1284 | 1 | 4 | 4 | 1 |
| 0.1173 | 0003891 | 0.0168233 | 0.0030043 | 447 | 1292 | 1 | 4 | 4 | 1 |
| 0.4544 | 0126303 | 0.033023 | -0.0079831 | 451 | 1300 | 1 | 4 | 4 | 1 |
| 1.1751 | 0273852 | 0.0490611 | -0.0178994 | 455 | 1308 | 1 | 4 | 4 | 1 |
| 1.0343 | 0454174 | 0.0705813 | -0.0285391 | 459 | 1316 | 1 | 4 | 4 | 1 |
| 1.336 | 0693379 | 0.0980824 | -0.0434089 | 463 | 1324 | 1 | 4 | 4 | 1 |
| 1.7192 | 0992789 | 0.1289065 | -0.0639615 | 467 | 1332 | 1 | 4 | 4 | 1 |
| 1.6788 | 1228603 | 0.1438925 | -0.0792502 | 471 | 1340 | 1 | 4 | 4 | 1 |
| 1.3828 | 1166148 | 0.1172261 | -0.0658707 | 475 | 1348 | 1 | 4 | 4 | 1 |
| 1.3142 | 096384 | 0.1042059 | -0.0543224 | 479 | 1356 | 1 | 4 | 4 | 1 |
| 1.3214 | 0547843 | 0.0780036 | -0.0257346 | 483 | 1364 | 1 | 4 | 4 | 1 |
| 0.3426 | 0034114 | 0.0529143 | 0.0010614 | 487 | 1372 | 1 | 4 | 4 | 1 |
| 0.6435 | 0161797 | 0.1354519 | -0.0360578 | 491 | 1380 | 1 | 4 | 4 | 1 |
| 0.1483 | 0023443 | 0.2333444 | -0.079905 | 495 | 1388 | 1 | 4 | 4 | 1 |
| 0.545 | 0299861 | 0.2717732 | -0.0836878 | 499 | 1396 | 1 | 4 | 4 | 1 |
| 1.3428 | 0768361 | 0.1878083 | -0.0429562 | 503 | 1404 | 1 | 4 | 4 | 1 |
| 1.2669 | 1392033 | -0.0182201 | 0.0319516 | 507 | 1412 | 1 | 4 | 4 | 1 |
| 0.2043 | 1844036 | -0.244083 | 0.1117934 | 511 | 1420 | 1 | 4 | 4 | 1 |
| -0.3473 | 2011124 | -0.3937384 | 0.1730638 | 515 | 1428 | 1 | 4 | 4 | 1 |
| -0.7019 | 0791705 | -0.2212603 | 0.1319247 | 519 | 1436 | 1 | 4 | 4 | 1 |
| -0.306 | 0146456 | -0.0539326 | 0.0701138 | 523 | 1444 | 1 | 4 | 4 | 1 |
| -0.3225 | 0077498 | -0.0585162 | 0.0489745 | 527 | 1452 | 1 | 4 | 4 | 1 |
| -0.6526 | .009078 | -0.0443871 | 0.029443 | 531 | 1460 | 1 | 4 | 4 | 1 |
| -0.1816 | 0124514 | -0.0334645 | 0.0170465 | 535 | 1468 | 1 | 4 | 4 | 1 |
| -0.2002 | 0161213 | -0.0292145 | 0.0083452 | 539 | 1476 | 1 | 4 | 4 | 1 |
| -0.749 | 0195381 | -0.0224174 | 0.0017061 | 543 | 1484 | 1 | 4 | 4 | 1 |
| -0.8945 | 0174908 | -0.0190351 | 0.0016491 | 547 | 1492 | 1 | 4 | 4 | 1 |
| -0.8393 | 0137431 | -0.0284181 | 0.0138157 | 551 | 1500 | 1 | 4 | 4 | 1 |
| -0.3829 | 0080367 | -0.0515576 | 0.0328564 | 555 | 1508 | 1 | 4 | 4 | 1 |
| 0.1601 | .001741 | -0.0633391 | 0.0425248 | 559 | 1516 | 1 | 4 | 4 | 1 |
| 0.0424 | 0005201 | -0.0531697 | 0.0375337 | 563 | 1524 | 1 | 4 | 4 | 1 |
| 0.3253 | 0026616 | -0.0401694 | 0.0308803 | 567 | 1532 | 1 | 4 | 4 | 1 |
| 0.3143 | 0105201 | -0.0489114 | 0.0357112 | 571 | 1540 | 1 | 4 | 4 | 1 |
| 0.0588 | 0168383 | -0.0685377 | 0.0459402 | 575 | 1548 | 1 | 4 | 4 | 1 |
| -0.2271 | 0141516 | -0.0766551 | 0.0462445 | 579 | 1556 | 1 | 4 | 4 | 1 |

FIGURE 2C

| | | | | | | | | | |
|---|---|---|---|---|---|---|---|---|---|
| -0.2747 | 0036056 | -0.0550916 | 0.0293165 | 583 | 1564 | 1 | 4 | 4 | 1 |
| -0.209 | 0068931 | -0.0192458 | 0.006623 | 587 | 1572 | 1 | 4 | 4 | 1 |
| -0.5235 | 0165892 | 0.0024981 | -0.0058384 | 591 | 1580 | 1 | 4 | 4 | 1 |
| -0.6894 | 0257216 | 0.0033233 | 0.0007962 | 595 | 1588 | 1 | 4 | 4 | 1 |
| -0.9907 | 0325489 | 0.005091 | 0.0075638 | 599 | 1596 | 1 | 4 | 4 | 1 |
| -1.4623 | 0358991 | 0.0134806 | 0.0062863 | 603 | 1604 | 1 | 4 | 4 | 1 |
| -1.108 | 0368747 | 0.0267156 | -0.0059277 | 607 | 1612 | 1 | 4 | 4 | 1 |
| -1.1478 | 0346921 | 0.0463785 | -0.0263763 | 611 | 1620 | 1 | 4 | 4 | 1 |
| -1.0832 | 0245849 | 0.0706615 | -0.0537231 | 615 | 1628 | 1 | 4 | 4 | 1 |
| -0.982 | 0085592 | 0.0960436 | -0.0913609 | 619 | 1636 | 1 | 4 | 4 | 1 |
| -0.7235 | 0038849 | 0.1390248 | -0.1341754 | 623 | 1644 | 1 | 4 | 4 | 1 |
| -0.2835 | 007225 | 0.1906535 | -0.1640824 | 627 | 1652 | 1 | 4 | 4 | 1 |
| 0.3436 | 0096046 | 0.1945012 | -0.1498101 | 631 | 1660 | 1 | 4 | 4 | 1 |
| 0.3529 | 0399073 | 0.0992329 | -0.0437883 | 635 | 1668 | 1 | 4 | 4 | 1 |
| -0.8184 | 0435475 | -0.0940939 | 0.0760264 | 639 | 1676 | 1 | 4 | 4 | 1 |
| -1.061 | 0665911 | -0.1918068 | 0.1019738 | 643 | 1684 | 1 | 4 | 4 | 1 |
| -0.0178 | 0745507 | -0.1075903 | 0.0542916 | 647 | 1692 | 1 | 4 | 4 | 1 |
| -0.1962 | 0568652 | -0.0486746 | 0.0381079 | 651 | 1700 | 1 | 4 | 4 | 1 |
| -0.9876 | 0359296 | 0.0326932 | -0.0085001 | 655 | 1708 | 1 | 4 | 4 | 1 |
| -1.6143 | 0445135 | -0.0015629 | -0.0342265 | 659 | 1716 | 1 | 4 | 4 | 1 |
| -1.7684 | 0869317 | -0.0932002 | 0.0278987 | 663 | 1724 | 1 | 4 | 4 | 1 |
| 0.6249 | 0002187 | -0.0692027 | 0.1025195 | 667 | 1732 | 1 | 4 | 4 | 1 |
| 1.8449 | 021823 | -0.0097241 | 0.0768349 | 671 | 1740 | 1 | 4 | 4 | 1 |
| 1.1003 | 0091217 | 0.0330577 | 0.0130689 | 675 | 1748 | 1 | 4 | 4 | 1 |
| 0.4758 | 0183744 | 0.0637341 | -0.0379127 | 679 | 1756 | 1 | 4 | 4 | 1 |
| 1.4846 | 007979 | 0.0812069 | -0.0275499 | 683 | 1764 | 1 | 4 | 4 | 1 |
| 1.3403 | 0161786 | 0.0748846 | -0.0264033 | 687 | 1772 | 1 | 4 | 4 | 1 |
| 0.331 | 0006392 | 0.0816648 | -0.0607518 | 691 | 1780 | 1 | 4 | 4 | 1 |
| -0.2963 | 0165192 | 0.084768 | -0.0687295 | 695 | 1788 | 1 | 4 | 4 | 1 |
| -0.3476 | 0269646 | 0.0891919 | -0.0572376 | 699 | 1796 | 1 | 4 | 4 | 1 |
| 0.0249 | 0226229 | 0.0882287 | -0.0486869 | 703 | 1804 | 1 | 4 | 4 | 1 |
| -0.0892 | 0140487 | 0.0603995 | -0.0304747 | 707 | 1812 | 1 | 4 | 4 | 1 |
| -0.1821 | .012267 | 0.0552065 | -0.0250661 | 711 | 1820 | 1 | 4 | 4 | 1 |
| -0.0406 | 0214814 | 0.0652396 | -0.0241926 | 715 | 1828 | 1 | 4 | 4 | 1 |
| 0.137 | 0216104 | 0.0594556 | -0.0167628 | 719 | 1836 | 1 | 4 | 4 | 1 |
| -0.6244 | 0171192 | 0.0633336 | -0.0103936 | 723 | 1844 | 1 | 4 | 4 | 1 |
| 0.1904 | 0241178 | 0.0767511 | -0.0073243 | 727 | 1852 | 1 | 4 | 4 | 1 |
| 0.7272 | 0480685 | 0.0964676 | 0.003384 | 731 | 1860 | 1 | 4 | 4 | 1 |
| 0.5274 | 0952503 | 0.1655956 | -0.0082466 | 735 | 1868 | 1 | 4 | 4 | 1 |
| 0.7945 | 1627059 | 0.2836901 | -0.0720872 | 739 | 1876 | 1 | 4 | 4 | 1 |
| -0.8043 | .255067 | 0.4373213 | -0.1750227 | 743 | 1884 | 1 | 4 | 4 | 1 |
| -1.8354 | 2936671 | 0.5286364 | -0.2287892 | 747 | 1892 | 1 | 4 | 4 | 1 |
| 0.7469 | 2341329 | 0.3477146 | -0.0877712 | 751 | 1900 | 1 | 4 | 4 | 1 |
| 0.2449 | 1489632 | -0.033803 | 0.1290147 | 755 | 1908 | 1 | 4 | 4 | 1 |
| -0.5388 | 0749652 | -0.3197428 | 0.2581663 | 759 | 1916 | 1 | 4 | 4 | 1 |
| -0.6419 | .017671 | -0.4208475 | 0.2800128 | 763 | 1924 | 1 | 4 | 4 | 1 |
| -1.1277 | 0222391 | -0.3676704 | 0.2030359 | 767 | 1932 | 1 | 4 | 4 | 1 |
| -1.1656 | 0422177 | -0.2480358 | 0.1083611 | 771 | 1940 | 1 | 4 | 4 | 1 |
| -0.7399 | 0462454 | -0.1413512 | 0.0579245 | 775 | 1948 | 1 | 4 | 4 | 1 |
| -0.1724 | 0437607 | -0.0731532 | 0.0423612 | 779 | 1956 | 1 | 4 | 4 | 1 |
| 0.245 | 0387386 | -0.0434038 | 0.0426443 | 783 | 1964 | 1 | 4 | 4 | 1 |

FIGURE 2D

| | | | | | | | | | |
|---|---|---|---|---|---|---|---|---|---|
| 0.5111 | 0408553 | -0.0397072 | 0.0336391 | 787 | 1972 | 1 | 4 | 4 | 1 |
| 0.1528 | 0539403 | -0.051742 | 0.0101872 | 791 | 1980 | 1 | 4 | 4 | 1 |
| -0.1085 | 075701 | -0.0816762 | -0.0088214 | 795 | 1988 | 1 | 4 | 4 | 1 |
| -0.0353 | 1095578 | -0.1463078 | -0.0027388 | 799 | 1996 | 1 | 4 | 4 | 1 |
| 0.2241 | 1562687 | -0.2376028 | 0.0223669 | 803 | 2004 | 1 | 4 | 4 | 1 |
| 0.4098 | 1599784 | -0.2389191 | 0.024658 | 807 | 2012 | 1 | 4 | 4 | 1 |
| 0.6149 | 1685745 | -0.2672103 | 0.0290887 | 811 | 2020 | 1 | 4 | 4 | 1 |
| -0.0612 | 185789 | -0.3372449 | 0.0481759 | 815 | 2028 | 1 | 4 | 4 | 1 |
| -0.5676 | 1823562 | -0.3832788 | 0.066848 | 819 | 2036 | 1 | 4 | 4 | 1 |
| -0.0587 | 1632611 | -0.3737507 | 0.0726149 | 823 | 2044 | 1 | 4 | 4 | 1 |
| -0.48 | 1312414 | -0.2768166 | 0.0682096 | 827 | 2052 | 1 | 4 | 4 | 1 |
| -0.135 | 1344321 | -0.2128445 | 0.0645757 | 831 | 2060 | 1 | 4 | 4 | 1 |
| 1.5287 | 117833 | -0.1622568 | 0.0583514 | 835 | 2068 | 1 | 4 | 4 | 1 |
| 0.5959 | 0489719 | -0.0820892 | 0.0568112 | 839 | 2076 | 1 | 4 | 4 | 1 |
| 1.0318 | 0.00299 | -0.0139699 | 0.0447392 | 843 | 2084 | 1 | 4 | 4 | 1 |
| 0.25 | 0243698 | 0.0390305 | 0.0126787 | 847 | 2092 | 1 | 4 | 4 | 1 |
| 0.0445 | 0594492 | 0.1154319 | -0.0263021 | 851 | 2100 | 1 | 4 | 4 | 1 |
| -0.0593 | 0617888 | 0.1314909 | -0.0396635 | 855 | 2108 | 1 | 4 | 4 | 1 |
| -0.8562 | 0347472 | 0.1080563 | -0.0475418 | 859 | 2116 | 1 | 4 | 4 | 1 |
| -0.8562 | 0270219 | 0.1117846 | -0.0668531 | 863 | 2124 | 1 | 4 | 4 | 1 |
| -0.1393 | .050247 | 0.1188499 | -0.0702093 | 867 | 2132 | 1 | 4 | 4 | 1 |
| -1.3975 | 0645408 | 0.077724 | -0.0531877 | 871 | 2140 | 1 | 4 | 4 | 1 |
| -1.1432 | 0697033 | 0.0741271 | -0.0521471 | 875 | 2148 | 1 | 4 | 4 | 1 |
| -0.2733 | 0838305 | 0.1118103 | -0.0598748 | 879 | 2156 | 1 | 4 | 4 | 1 |
| -0.2517 | 0756611 | 0.1263029 | -0.0507805 | 883 | 2164 | 1 | 4 | 4 | 1 |
| 0.2724 | .042196 | 0.1376595 | -0.051825 | 887 | 2172 | 1 | 4 | 4 | 1 |
| 0.9113 | 0017157 | 0.1254588 | -0.0595678 | 891 | 2180 | 1 | 4 | 4 | 1 |
| 0.8766 | 0051536 | 0.1462821 | -0.0666593 | 895 | 2188 | 1 | 4 | 4 | 1 |
| 3.1112 | 0140879 | 0.1752303 | -0.0671997 | 899 | 2196 | 1 | 4 | 4 | 1 |
| 2.6735 | 0012583 | 0.165346 | -0.078699 | 903 | 2204 | 1 | 4 | 4 | 1 |
| 1.2158 | 0242778 | 0.1713437 | -0.1187224 | 907 | 2212 | 1 | 4 | 4 | 1 |
| 0.7702 | 0494174 | 0.2165613 | -0.1833169 | 911 | 2220 | 1 | 4 | 4 | 1 |
| 1.8376 | 0720025 | 0.2613153 | -0.2372307 | 915 | 2228 | 1 | 4 | 4 | 1 |
| 0.4567 | 0915369 | 0.1761955 | -0.2049605 | 919 | 2236 | 1 | 4 | 4 | 1 |
| -0.3705 | 0859843 | -0.0256055 | -0.0785582 | 923 | 2244 | 1 | 4 | 4 | 1 |
| -1.5174 | 0042859 | -0.1448509 | -0.0013478 | 927 | 2252 | 1 | 4 | 4 | 1 |
| -0.5258 | 0747545 | -0.2715632 | 0.0754112 | 931 | 2260 | 1 | 4 | 4 | 1 |
| 0.2839 | 0785018 | -0.3944573 | 0.2136819 | 935 | 2268 | 1 | 4 | 4 | 1 |
| -0.4514 | 0.09844 | -0.3503446 | 0.3234998 | 939 | 2276 | 1 | 4 | 4 | 1 |
| 0.4945 | 1598304 | -0.0827608 | 0.2089848 | 943 | 2284 | 1 | 4 | 4 | 1 |
| -1.49 | 2231499 | 0.1665051 | 0.0066736 | 947 | 2292 | 1 | 4 | 4 | 1 |
| -2.2608 | 2012532 | 0.0140123 | -0.0982895 | 951 | 2300 | 1 | 4 | 4 | 1 |
| -1.4086 | 0702564 | -0.0585169 | -0.124995 | 955 | 2308 | 1 | 4 | 4 | 1 |
| 3.4879 | 1771957 | 0.1381918 | 0.0153921 | 959 | 2316 | 1 | 4 | 4 | 1 |
| 2.8298 | 0881344 | 0.2182197 | -0.0723481 | 963 | 2324 | 1 | 4 | 4 | 1 |
| 0.0521 | 0278635 | 0.1384929 | -0.1379226 | 967 | 2332 | 1 | 4 | 4 | 1 |
| -0.5042 | 0890663 | 0.0448882 | -0.0754787 | 971 | 2340 | 1 | 4 | 4 | 1 |
| -1.9967 | 0893057 | 0.0956985 | -0.0843435 | 975 | 2348 | 1 | 4 | 4 | 1 |
| 1.633 | 0677622 | 0.1103047 | 0.0127988 | 979 | 2356 | 1 | 4 | 4 | 1 |
| 0.9262 | 0302188 | 0.0070979 | 0.0055675 | 983 | 2364 | 1 | 4 | 4 | 1 |
| -0.8083 | 0071355 | 0.0245187 | -0.0367879 | 987 | 2372 | 1 | 4 | 4 | 1 |

FIGURE 2E

| -1.2252 | 0163733 | -0.0097774 | -0.0317304 | 991 | 2380 | 1 | 4 | 4 | 1 |
| 0.07 | 0114154 | -0.0809886 | 0.0729404 | 995 | 2388 | 1 | 4 | 4 | 1 |
| -0.918 | 0019331 | -0.1697068 | 0.1723908 | 999 | 2396 | 1 | 4 | 4 | 1 |
| -0.2346 | 0291271 | -0.2178754 | 0.1755645 | 1003 | 2404 | 1 | 4 | 4 | 1 |
| -0.1923 | 0634367 | -0.2323132 | 0.1389374 | 1007 | 2412 | 1 | 4 | 4 | 1 |
| 1.7413 | 0222494 | -0.1123926 | 0.0814187 | 1011 | 2420 | 1 | 4 | 4 | 1 |
| -0.1827 | 0199519 | -0.0550661 | 0.0539011 | 1015 | 2428 | 1 | 4 | 4 | 1 |
| -1.5177 | 0507124 | -0.0448004 | 0.0500707 | 1019 | 2436 | 1 | 4 | 4 | 1 |
| -0.2804 | 0234917 | -0.0477237 | 0.057649 | 1023 | 2444 | 1 | 4 | 4 | 1 |
| -3.0762 | 0091297 | -0.0619199 | 0.0290244 | 1027 | 2452 | 1 | 4 | 4 | 1 |
| -0.0636 | 0004693 | -0.0580129 | 0.0087214 | 1031 | 2460 | 1 | 4 | 4 | 1 |
| -0.6692 | 0034797 | -0.0730763 | 0.0204012 | 1035 | 2468 | 1 | 4 | 4 | 1 |
| -0.6659 | 007201 | -0.0719952 | 0.0121356 | 1039 | 2476 | 1 | 4 | 4 | 1 |
| -1.3137 | 0078079 | 0.0006311 | -0.027481 | 1043 | 2484 | 1 | 4 | 4 | 1 |

FIGURE 2F

METHOD FOR PREDICTING THE AMOUNT OF ACCESSIBLE CARBOHYDRATE IN A FEEDSTOCK SAMPLE USING A NEAR-INFRARED MODEL

CROSS-REFERENCE TO RELATED APPLICATIONS

This application is a National Stage application under 35 U.S.C. §371 and claims the benefit of International Application No. PCT/US2008/082047, filed Oct. 31, 2008, which claims the benefit of priority of U.S. Provisional Application Nos. 61/056,631, filed May 28, 2008, 61/025,033, filed Jan. 31, 2008, and 60/984,976, filed Nov. 2, 2007. The contents of all of the foregoing applications are hereby incorporated by reference in their entireties.

TECHNICAL FIELD

This document relates to methods and materials involved in determining the compositional characteristics of plant biomass and the conversion efficiency of the biomass to produce fuels, chemicals and/or heat and power under various processing conditions. For example, this document provides materials and methods for measuring levels of accessible carbohydrate and for identifying plant material having higher levels of accessible carbohydrate.

BACKGROUND

Plants store energy from sunlight in the form of chemical bonds that compose plants. The energy stored in plant materials can be converted to forms of energy such as heat, electricity and liquid fuels, depending upon the plant material employed and the process applied to extract energy from it. Other processes can produce chemical intermediates from plant biomass that are useful in a variety of industrial processes, for instance lactic acid, succinic acid, etc.

Plant materials have been used for millennia by humans to generate heat by direct combustion in air. For building and process heating purposes, this heat is typically used to generate steam, which is a more transportable heat source used to heat buildings and public areas using heat exchangers of various design. The production of steam may also be used to drive turbines, which transform heat energy into electrical energy. These processes typically involve a simple, direct combustion process of the plant material alone, or a co-firing process with coal or other energy source.

Fuels such as ethanol can be produced from plant materials by a number of different processes. For example, the sucrose in sugarcane can be extracted from the plant material and directly fermented to ethanol using a microorganism, such as brewer's yeast. Brazil has converted a significant portion of its transportation sector over to ethanol derived from sugarcane, proving this can be done on a very large scale over broad geography. As another example, the starch from corn can be processed using α-amylase and glucoamylase to liberate free glucose that is subsequently fermented to ethanol. The US uses a significant portion of its corn crop to produce ethanol from starch. While these advances are significant, the ability to increase the amount of liquid transportation fuel obtained from plant material is limited and insufficient to achieve federally mandated renewable energy targets because only a small fraction of the solar energy captured and transformed into chemical energy in plants is converted into biofuels in these industrial processes.

Plant material can be used for the production of cellulosic biofuels by biochemical processes employing enzymes and/or microorganisms or by thermochemical processes such as. Biomass to Liquids (BtL) technology using high temperature and non-enzymatic catalysts. There are also examples of hybrid thermochemical/biochemical processes. Biochemical processes typically employ physical and chemical pretreatments, enzymes, and microorganisms to deconstruct the lignocellulose matrix of biomass in order to liberate the fermentable from cellulose, hemicellulose, and other cell wall carbohydrates, which are subsequently fermented to ethanol by a microorganism. Currently, many different processing methods are being developed for biofuel production that employ different strategies for pretreatment, enzyme cocktails, and microorganisms. Many of these processes are focused on the production of ethanol, but butanol and other useful molecules (e.g., lactic acid, succinic acid, polyalkanoates, etc.) can also be produced in this type of process. The conversion product molecule produced is usually defined by the microorganisms selected for fermentation.

Thermochemical processes employ very high temperatures in a low oxygen (i.e., $O_2$) environment to completely degrade the organic constituents of biomass to syngas, largely composed of molecular hydrogen ($H_2$) and carbon monoxide (CO) gas. These simple molecules are then re-formed into more useful and valuable molecules (fuels or chemical intermediates) utilizing a Fischer-Tropsch process or other methods usually employing a chemical catalyst of some sort. These processes are effective at producing biofuels that are similar to current petrochemical-based hydrocarbon fuels (i.e., gasoline, diesel, jet fuel), although other biofuel molecules can also be produced in these types of processes (i.e., ethanol, butanol, kerosene).

A variant form of thermochemical process uses pyrolysis (i.e., thermal degradation in the complete absence of oxygen) to partially degrade the organic constituents present in plant biomass to a chemically heterogeneous liquid bio-oil. This serves to increase the energy density of the biomass to facilitate transport to centralized processing facilities where the bio-oil is further processed to a desired product slate.

The economic viability of biomass conversion processes is significantly impacted by the composition of the plant material and its conversion efficiency to heat, electricity, biofuels or chemical intermediates under specific processing conditions. For biochemical processes producing biofuels or other chemicals, the recalcitrance of the lignocellulose matrix of the biomass is a major factor in conversion efficiency. Current analytical methods for measuring various parameters relevant to the conversion of plant materials to energy are slow, expensive and require highly skilled labor to produce accurate and reliable information. The low throughput and high cost of these methods limits their use in selecting and breeding for varieties of plant biomass feedstocks improved in their conversion performance characteristics. For the same reasons, these methods are also limited in their use for monitoring various process intermediates during biomass processing. These difficulties in feedstock and process development have limited the realization of the potential of cellulosic biofuels and hindered the development of economically viable processes.

SUMMARY

The invention is based in part on the discovery that NIR models can be developed that characterize the nature and/or quantity of plant biomass components of significance to various biomass conversion processes. For example, it has been surprisingly found that enzymatic saccharification conversion efficiency can be predicted based on NIR spectroscopy of the dried and milled biomass. Such NIR models can be used to predict saccharification efficiency of unknown biomass samples under identical or similar processing conditions. Such models can also be used to predict the final yield of biofuel from a particular biomass material under those same specific processing conditions. Thus, such models can be used to determine optimum conditions for processing a particular feedstock in a biorefinery. NIR models can be used in plant breeding to select for plants having higher levels of accessible carbohydrate and higher yield of biofuel (i.e., ethanol) in gallons/ton of biomass. Such selected plants may be used to produce improved varieties having a higher amount of accessible carbohydrate and higher saccharification efficiency as a value-added trait. Such plants are useful to produce biomass that may be converted to a liquid fuel or other chemicals.

Thus, in one aspect, the invention features a method of formulating a NIR model. The method comprises subjecting a plurality of diverse biomass feedstock samples of the same type to near infrared spectroscopy to produce NIR spectroscopic data from each sample. The chemical composition of each feedstock sample is measured independently using established wet chemical or other techniques, as well as the total amount of mono- and di-saccharides solubilized from each sample after processing under defined sets of pretreatment/enzyme load conditions. The NIR model is generated from the correlations that emerge between the spectroscopic data, the chemical composition data, and the saccharification results. The resulting NIR model is capable of predicting the amount of accessible carbohydrate in a test feedstock sample if it were to be processed under the same or similar defined pretreatment/enzyme load condition. In some embodiments, the generating step comprises regressing the spectral data against the chemical composition data and saccharification results, and deriving a calibration equation using multivariate statistical methods. The method can further include measuring the total amount of mono- and di-saccharides solubilized from each of the feedstock samples after processing by a second defined pretreatment/enzymatic load condition, and generating a second NIR model from the mono- and di-saccharide amounts solubilized under the second defined pretreatment/enzymatic load conditions, the spectroscopic data and chemical composition data. The chemical composition predicted by the NIR model can include the ferulate and/or acetate content of the biomass, if the method has been properly calibrated for those constituents. The NIR model can be generated from recalcitrant carbohydrate values.

In another aspect, the invention features a method for determining the amount of accessible carbohydrate material in a feedstock sample. The method comprises collecting NIR spectral data from a feedstock sample to be tested, applying a NIR model of accessible carbohydrate in feedstocks of the same type as the sample to the spectral data, and predicting the amount of accessible carbohydrate material in the sample based on the results of applying the model.

In another aspect, the invention features a method for determining the amount of recalcitrant carbohydrate material in a feedstock sample. The method comprises collecting NIR spectral data from a feedstock sample to be tested, applying a NIR model of recalcitrant carbohydrate in feedstocks of the same type as the sample to the spectral data, and predicting the amount of recalcitrant carbohydrate material in the sample based on the results of applying the model.

In another aspect, the invention features a method for predicting the saccharification conversion efficiency of a feedstock sample. The method comprises collecting NIR spectral data from a test feedstock sample, applying a NIR model of accessible carbohydrate in feedstocks of the same type as the sample to the spectral data, and predicting the saccharification conversion efficiency of the sample, based on the results of applying the model. The saccharification conversion efficiency can be, for example, glucose conversion efficiency or glucose+ xylose conversion efficiency. The method can further include predicting the yield of monosaccharides from the feedstock sample.

In another aspect, a method for predicting the product yield of a feedstock sample is disclosed. The method comprises collecting NIR spectral data from a feedstock sample to be tested, applying a NIR model of product yield in feedstocks of the same type as the sample to the spectral data and predicting the product yield of the feedstock sample, based on the results of applying the model. The product yield in the method can be biofuel yield. The feedstock sample can be an herbaceous or woody material, e.g., switchgrass, sorghum, sugarcane, miscanthus, poplar, willow, rice or corn.

In another aspect, the invention features a method for determining the amount of ferulate and acetate content in a feedstock sample. The method comprises collecting NIR spectral data from a feedstock sample to be tested, applying a NIR model of ferulate and acetate content in feedstocks of the same type as the sample to the spectral data and predicting the amount of ferulate and acetate content in the feedstock sample, based on the results of applying the model.

In another aspect, the invention features a method for determining enzymatic conditions for processing a biomass feedstock. The method comprises collecting NIR spectral data from a test feedstock sample, applying one or more NIR models of accessible carbohydrate in feedstocks of the same type as the sample to the spectral data, and predicting enzyme loading conditions that produce a defined saccharification of the sample, based on the results of the applying step. In some embodiments, the method also includes predicting pretreatment conditions that produce a defined saccharification of the feedstock sample, based on the results of applying the model.

In another aspect, a method for determining processing conditions for a biomass feedstock is disclosed. The method comprises collecting NIR spectral data from a feedstock sample to be tested, applying one or more NIR models of processing conditions in feedstocks of the same type as the sample to the spectral data and predicting processing conditions that produce a defined saccharification of the feedstock sample, based on the results of the applying step. The processing conditions can comprise a pretreatment. The processing conditions can include the use of one or more enzymes used to saccharify the pretreated feedstock sample. The feedstock sample can be an herbaceous or woody material. The feedstock sample can comprise a species selected from the group consisting of switchgrass, sorghum, sugarcane, miscanthus, poplar, willow, rice and corn.

In another aspect, the invention features a method of selecting a plant. The method comprises providing a population of plants of a biomass species, collecting NIR spectral data from a feedstock sample from plants in the population, applying a NIR model of accessible carbohydrate in feedstocks of the same type as the sample to the spectral data, predicting the saccharification efficiency of each the feedstock sample, based on the results of the applying step, and identifying one or more plants in the population that have a higher predicted saccharification efficiency relative to the average predicted saccharification efficiency for the population. In some aspects, a method of selecting a plant comprises providing a population of plants of a biomass species, collecting NIR spectral data from a feedstock sample from each of the plants in the population, applying a NIR model of one or more of S weight percent, G weight percent, and H weight percent in feedstocks of the same type as the sample to the spectral data, predicting the weight percents of one or more of S, G, and H of each feedstock sample, based on the results of said applying step, and identifying one or more plants in the population that have an altered weight percent of one or more of S, G, or H relative to the average predicted weight percent of S, G, or H for the population. The feedstock sample can be an herbaceous or woody material, e.g., switchgrass, sorghum, sugarcane, miscanthus, poplar, willow, rice and corn.

In another aspect, the invention features a method of breeding a plant variety. The method comprises crossing two or more parent biomass plants, and selecting progeny of the cross that have a higher predicted saccharification conversion efficiency relative to the saccharification conversion efficiency of at least one of the parents. The selecting step can include collecting NIR spectral data from a feedstock sample from one or more progeny of the cross, applying a NIR model of accessible carbohydrate in feedstocks of the same type as the sample to the spectral data, and predicting the saccharification conversion efficiency of the sample, based on the results of the applying step. Progeny are then selected that have a predicted increase in saccharification conversion efficiency relative to the predicted saccharification conversion efficiency of at least one of the parent plants. Also featured is a method of breeding a plant variety, in which progeny of a cross are selected that have a higher predicted amount of accessible carbohydrate relative to the amount of accessible carbohydrate of at least one of the parent plants. In some aspects, a method of breeding a plant variety comprises crossing two or more parent biomass plants and selecting progeny of the cross that have an altered predicted weight percent of one or more of S, G, or H relative to the weight percent of S, G, or H of at least one of the parent plants. The feedstock sample can be an herbaceous or woody material, e.g., switchgrass, sorghum, sugarcane, miscanthus, poplar, willow, rice and corn.

In another aspect, the invention features a method of breeding a plant variety that includes identifying one or more members of a population of plants of a biomass species that have a higher predicted saccharification conversion efficiency relative to the average saccharification conversion efficiency of the population. The one or more identified members are then propagated by sexual or asexual techniques. Also featured is method of breeding a plant variety, in which one or more members of such a population are identified that have a higher predicted amount of accessible carbohydrate relative to the average amount of accessible carbohydrate of the population. Such identified plants are propagated by sexual or asexual techniques.

The invention also features a method for managing a feedstock supply chain. The method includes collecting NIR spectral data from a feedstock sample to be tested, applying a NIR model of accessible carbohydrate in feedstocks of the same type as the sample to the spectral data, predicting the saccharification conversion efficiency of the feedstock sample based on the results of the applying step, and inputting the predicted saccharification conversion efficiency into a crop index system accessible by a feedstock processor. The method can further include classifying the feedstock according to feedstock quality specifications set by the feedstock processor, and offering a specified price to the producer of the feedstock based on the feedstock classification.

The invention also features a computer readable medium comprising computer program instructions, which when executed by a processor perform a method. The method comprises receiving NIR spectral data from a feedstock sample to be tested, applying a NIR model of accessible carbohydrate in feedstocks of the same type as the sample to the spectral data, and conveying the amount of accessible carbohydrate material in the feedstock sample, based on the results of applying the model, to a crop index system.

In another aspect, the invention features a computer-implemented method, that comprises collecting NIR spectral data from a feedstock sample to be tested, applying a NIR model of accessible carbohydrate in feedstocks of the same type as the feedstock sample to the spectral data, predicting saccharification conversion efficiency of the feedstock sample based on the application of the NIR model, and outputting the predicted saccharification conversion efficiency for use by a crop index system. The system is configured to determine biomass quality for feedstocks from which the feedstock sample was obtained. In another aspect, a computer-implemented method comprises receiving, at a crop index system, a predicted saccharification conversion efficiency of a feedstock, the feedstock associated with a producer providing the feedstock, determining a supply chain distribution based on the predicted saccharification conversion efficiency, and outputting an indication of the supply chain distribution to a feedstock processor.

In another aspect the invention features a system comprising an interface for receiving NIR spectral data from a feedstock sample, and a NIR model of accessible carbohydrate in feedstocks of the same type as the feedstock sample that outputs, for use by a crop index system, a predicted saccharification conversion efficiency of the feedstock sample based on the application of the NIR model. The crop index system is configured to determine biomass quality for feedstocks of the same type as the feedstock sample.

The invention also features a method of formulating a NIR model. The method comprises subjecting a plurality of biomass feedstock samples of the same type to near infrared spectroscopy to produce NIR spectroscopic data from each sample. The thermochemical product yield of each feedstock sample is measure by thermochemical techniques, and the NIR model is generated from the spectroscopic data and the thermochemical product yields. The resulting NIR model is capable of predicting the thermochemical product yield of a test feedstock sample. The thermochemical product can be a liquid biofuel.

In another aspect the invention features a method for determining the amount of fixed carbon in a feedstock sample. Such a method includes collecting NIR spectral data from a feedstock sample to be tested, applying a NIR model of fixed carbon in feedstocks of the same type as the sample to the spectral data, and predicting the amount of fixed carbon in the feedstock sample, based on the results of applying the model. In another aspect, the invention features a method for predicting C:H:O weight percents in a feedstock sample. The method comprises collecting NIR spectral data from a feedstock sample to be tested, applying a NIR model of C:H:O weight percents in feedstocks of the same type as the sample to the spectral data, and predicting C:H:O weight percents in the feedstock sample, based on the results of the applying step. In another aspect the invention features a method for predicting the Higher Heating Value (HHV) of a feedstock sample. The method comprises collecting NIR spectral data from a feedstock sample to be tested, applying a NIR model of the HHV of feedstocks of the same type as the sample to the spectral data, and predicting the HHV of the feedstock sample, based on the results of applying the model.

The invention also features a computer-implemented method of predicting economic value of a biomass. Such a method includes collecting NIR spectral data from a feedstock sample to be tested. A NIR model of the HHV of feedstocks of the same type as the sample is applied to the spectral data, and the HHV of the feedstock sample is predicted based on the application of the model. A NIR model of the fixed carbon of feedstocks of the same type as the sample is also applied to the spectral data, and the fixed carbon of the feedstock sample is predicted based on the application of the fixed carbon model. A NIR model of accessible carbohydrate in feedstocks of the same type as the sample is also applied to the spectral data and the saccharification conversion efficiency of the feedstock sample is predicted based on the application of the accessible carbohydrate model. Defined biochemical and thermochemical processing conditions that result in a defined economic value from the feedstock sample are then predicted, based on the results from each of the NIR models. Such methods can be used to place a value on biomass material in terms of end product yield, predict optimum biofuel yield of a material. Such methods can also be used to select varieties from a population and/or direct crosses in a breeding program to achieve optimum economic value.

In another aspect, the invention features a computer-implemented method comprising receiving, at a crop index system, a predicted HHV, a predicted fixed carbon amount and a predicted saccharification efficiency of a feedstock, the feedstock associated with a producer providing the feedstock, determining a supply chain distribution based on the predicted HHV, predicted fixed carbon amount and predicted saccharification efficiency, and outputting an indication of the supply chain distribution to a feedstock processor.

In another aspect, the invention features a method for predicting the amount of energy obtainable from a feedstock sample, comprising collecting NIR spectral data from a feedstock sample to be tested, applying a NIR model of the HHV and the amount of fixed carbon in feedstocks of the same type as the sample to the spectral data, and predicting the amount energy obtainable from the feedstock sample, based on the results of the applying step. In another aspect, a method for determining processing conditions for a biomass feedstock is disclosed, comprising collecting NIR spectral data from a feedstock sample to be tested, applying one or more NIR models of the amount of fixed carbon and the HHV of feedstocks of the same type as the sample to the spectral data, and predicting processing conditions that produce a defined combustion of the feedstock sample, based on the results of the applying step. The processing conditions can comprise a pretreatment.

In another aspect, the invention features a method of formulating a NIR model. The method comprises subjecting a plurality of biomass feedstock samples of the same type to near infrared spectroscopy to produce NIR spectroscopic data from each sample, measuring the chemical composition of each feedstock sample by one or more analytical chemistry techniques, and generating the NIR model from the spectroscopic data and the chemical composition data. The NIR model is capable of predicting one or more of S weight percent, G weight percent and H weight percent in a test feedstock sample. A method for determining one or more of S, G, and H weight percents in a feedstock sample comprises collecting NIR spectral data from a feedstock sample to be tested, applying a NIR model of one or more of S weight percent, G weight percent and H weight percent in feedstocks of the same type as said sample to the spectral data and, based on the results of said applying step, predicting one or more of S weight percent, G weight percent, and H weight percent in the feedstock sample.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF THE DRAWINGS

FIG. 2A-F is a protein NIR/PLS equation using three principal components (PCs). Coefficients for each PC at each wavelength are shown. Weighting coefficients for protein concentration are also given. Math treatment options are also shown indicating first derivative treatment followed by standard normal variate smoothing with a segment of 4 cm$^{-1}$ and a block of 4 cm$^{-1}$ with a first order polynomial fit. The equation was developed using WinISI version 4.0 multivariate analysis software from Infrasoft International, State College, Pa., USA.

Like reference symbols in the various drawings indicate like elements.

DETAILED DESCRIPTION

1. Overview

Figure 1:
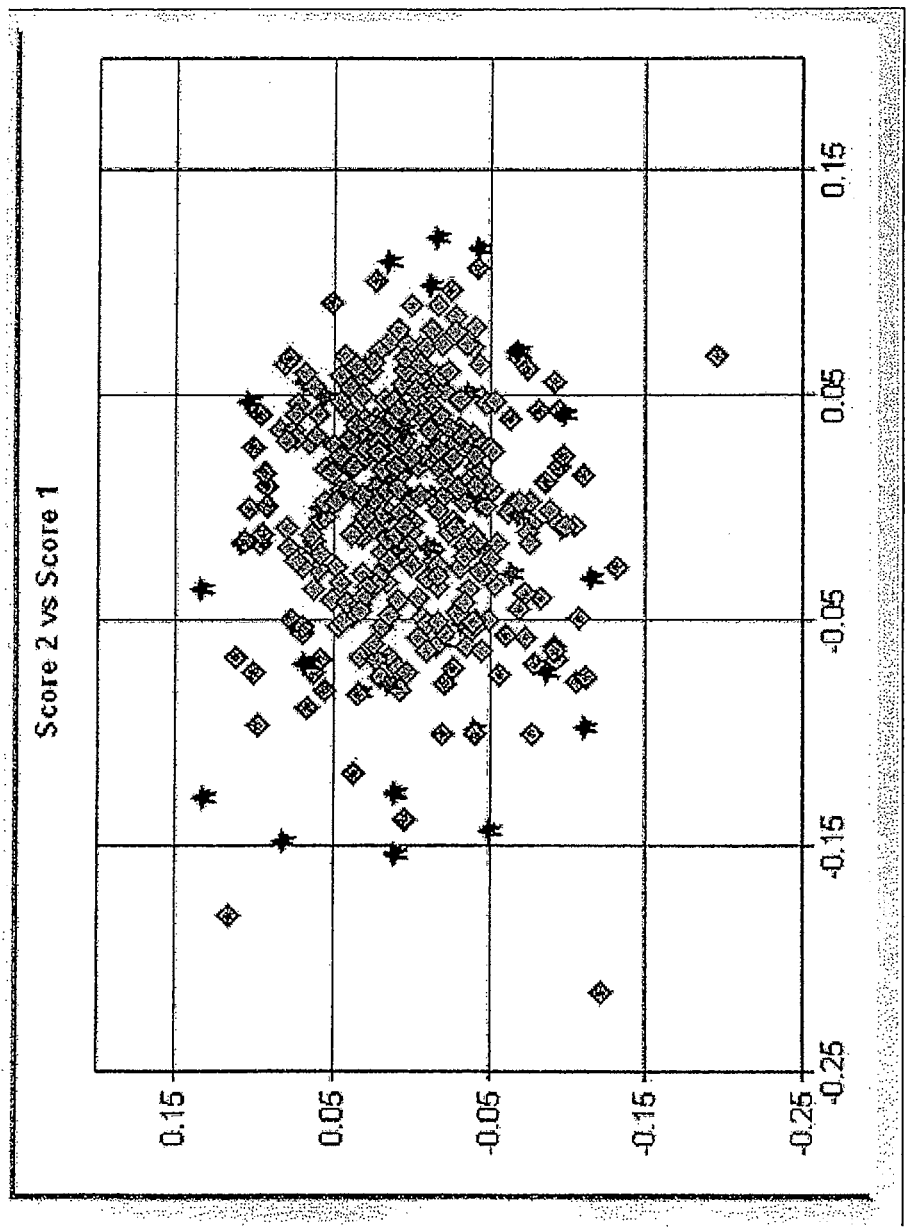
FIG. 1 is a Principal Components Analysis (PCA) score plot of switchgrass survey samples and the subset of 55 samples selected for method calibration. Diamonds are survey samples and stars are calibration samples.

Plant biomass can be used for the production of energy by 1) conversion to biofuels via a) biochemical processes (employing enzymes and/or microorganisms) or b) thermochemical processes such as Biomass to Liquids (BtL) technology (using high temperature and non-enzymatic catalysts); or 2) generation of heat and/or electricity via thermochemical processes (combustion).

The efficiency by which biomass can be converted into energy via these processes is dependent upon a number of compositional characteristics of the biomass. The relevant compositional characteristics differ based on the conversion process design.

Generally, the conversion efficiency of biochemical processes is most influenced by the concentration of carbohydrate in the biomass and the ease with which that carbohydrate can be hydrolyzed to fermentable sugars. Lignin in a biochemical process is typically converted to energy after passing through the fermentation process, when it is burned to generate heat and electricity. Similarly, the efficiency and yield of thermochemical processes for the production of biofuels are most influenced by the overall amounts of carbon to hydrogen to oxygen (C:H:O weight percents) and ash content of the biomass. The efficiency of thermochemical combustion processes is most influenced by the higher heating value (HHV) and ash content of the biomass. The HHV of biomass is a function of carbon, hydrogen and oxygen content of the biomass.

Some of these compositional parameters are multi-parametric in nature and/or are influenced by other components in the biomass matrix. As a result, the evaluation of these parameters often results in inaccurate estimates of the conversion efficiency of biomass in a particular process. Methods utilizing data from direct conversion efficiency measurements could be very useful for understanding the relative utility of various biomass materials for the production of energy.

The concept of conversion efficiency describes the yield of energy (in terms of biofuel, heat, and/or electricity) derived from a biomass starting material subjected to a particular process as compared to a theoretical yield of all the energy stored in the biomass starting material. In particular, for biochemical processing of biomass to biofuels, it is possible that two plant materials having similar compositional parameters by weight (i.e., cellulose, hemicellulose, pectins, lignin, etc.) can have different conversion efficiencies. These differences are likely to be due to variations in the three dimensional composite structure of the four major polymers that make up the bulk of plant cell walls. For thermochemical processes, these same two compositionally similar feedstocks would be expected to give similar process efficiencies, because thermochemical processes are less sensitive to cell wall architecture and these two samples have the same C:H:O weight percents. Following the same reasoning, samples with dissimilar amounts of cellulose, hemicellulose, pectin and lignin, but that have similar C:H:O weight percents overall, would also be expected to have similar thermochemical process efficiencies.

The invention features materials and methods related to rapid prediction of parameters useful for biofuel production and for development of improved plant varieties and populations. These materials and methods include Near Infrared (NIR) spectroscopic models that rapidly characterize plant material and identify those with higher levels of enzyme-accessible carbohydrate (for biochemical conversion processes), as well as materials and methods for processing plant material having higher levels of accessible carbohydrate. These materials and methods also include NIR models that predict biofuel yield in thermochemical Biomass-to-Liquids (BtL) processes, as well as fixed carbon and/or Higher Heating Value (HHV) for heat and electricity production. The ability to rapidly and inexpensively characterize these parameters greatly facilitates the development of improved plant varieties, populations and crops with enhanced characteristics for bioenergy production. The ability to rapidly and inexpensively characterize such parameters may also be used to define operations in a biorefinery to optimize economic return from a biomass feedstock and process.

2. Definitions

"Accessible Carbohydrate" refers to mono- and oligo-saccharides released into the aqueous phase after processing of a biomass feedstock. The amount of accessible carbohydrate in a feedstock is related to the pretreatment and enzymatic saccharification conditions chosen for the saccharification process and to the composition and structure of the initial biomass feedstock.

"Ash" refers to inorganic material that contributes to the dry weight of the feedstock. Ash content in biomass feedstocks can be determined using published, standard methods such as ASTM Standard E1755.

"Biochemical processing" refers to a primarily biological process where plant materials are converted to liquid products using enzymes and/or fermentation organisms. Biochemical processing may require thermochemical pretreatments.

"Biofuels" include, but are not limited to, biodiesel, methanol, ethanol, butanol, linear alkanes ($C_5$-$C_{20}$), branched-chain alkanes ($C_5$-$C_{26}$), mixed alkanes, linear alcohols ($C_1$-$C_{20}$), branched-chain alcohols ($C_1$-$C_{26}$), linear carboxylic acids ($C_2$-$C_{20}$), and branched-chain carboxylic acids ($C_2$-$C_{26}$). In addition, ethers, esters and amides of the aforementioned acids and alcohols, as well as other conjugates of these chemicals may be of interest. Many of these chemicals can be subsequently converted by chemical reactions to other high value, high volume chemicals.

"Biomass" refers to organic matter. Biomass includes plant matter derived from herbaceous and woody energy crops, agricultural food and feed crops, agricultural crop wastes and residues, wood wastes and residues, aquatic plants, and other plant-derived materials. Biomass may also include algae, yard wastes, and include some municipal wastes. Biomass is a heterogeneous and chemically complex renewable resource. Components of biomass include glucan, xylan, fermentable sugars, arabinan, sucrose, lignin, protein, ash, extractives, ferulate, and acetate.

"Biopower" refers to the process of using plant biomass to generate electricity and heat. There are three different types of biopower systems: direct-fire, co-firing, and gasification. Direct-firing involves burning plant biomass directly to produce steam for heat. This steam may also be captured and directed to spin a turbine that produces electricity. This system is very similar to conventional power production that uses coal or oil to generate electricity. Co-firing is similar to direct-firing except for the fact that plant biomass is burned in combination with a fossil fuel, most often coal, in a high-efficiency boiler. Gasification systems are different than the other two methods, in that high temperatures are used in an oxygen-starved environment to convert biomass into a gas (a mixture of hydrogen, carbon monoxide, and methane). This gas can then be used to fuel an energy efficient combined-cycle gas turbine, which is much like a jet engine only it turns an electric generator instead of propelling a jet. The electricity produced may also be stored in batteries.

"Carbohydrate material" refers to polysaccharides found in biomass, such as glucans, arabinans, xylans, and pectins.

"Cellulose" refers to a glucan polysaccharide, i.e., a glucose polymer with β-1,4-glycosidic linkages. The β-linkages in cellulose form linear chains that are highly stable and resistant to chemical attack because of the high degree of hydrogen bonding that can occur between chains of cellulose. Hydrolysis of cellulose results in the production of cellobiose, $C_{12}H_{22}O_{11}$, and the monosaccharide glucose, $C_6H_{12}O_6$. Cellulose is the principal carbohydrate constituent of wood and other biomass.

"Co-products" refers to chemicals of interest that may be obtained from plant biomass crops or as byproducts of biofuel production. Co-products may be produced by processes employing the carbohydrate portion of plant biomass or from other components. Exemplary co-products include, but are not limited to, 1,3-propanediol, 3-hydroxypropionic acid, glycerol, ethylene glycol, propylene glycol, acetone, acrylic acid, methacrylic acid, succinic acid, 1,4-butanediol, tetrahydrofuran, butyrolactone, fumaric acid, malic acid, 2,5-furandicarboxylic acid, 2,5-dimethylfuran, aspartic acid, glucaric acid, glutamic acid, itaconic acid, levulinic acid, 3-hydroxybutyrolactone, sorbitol, xylitol, and arabinitol. See, T. Werpy and G. Peterson "Top Value Added Chemicals from Biomass" U.S. Dept. of Energy (2004), available on the world wide web at osti<dot>gov/bridge. In addition, ethers, esters and amides of the aforementioned acids and alcohols, as well as other conjugates of these chemicals may be of interest. Many of these chemicals can be subsequently converted by chemical reactions to other high value, high volume chemicals. Other co-products of interest may include lignin, phenylpropanoids, nutritional ingredients, nutritionally-enriched animal feed, protein-enriched animal feed, collagen, and gelatin.

"Extractives" refers to a number of different compounds in biomass that can be extracted from biomass by means of polar and non-polar solvents that do not degrade the biomass structure. Such solvents include water, ethanol, hexane, ether, benzene, and methanol. The amount and chemical nature of extractives found in a biomass sample can vary by species, harvest time and sample type.

"Ferulate and acetate content" refers to the concentration of ferulic acid and acetic acid molecules attached to the xylan backbone of hemicellulose as measured by the procedure described in Sluiter, et al., NREL/TP-510-42618, April 2008, National Renewable Energy Laboratory, Golden, Colo., and the procedure described in Saulinier, L. et al., Carbohydrate Research (1995) Vol. 272:241-253.

"Fixed carbon" refers to the amount of non-volatile carbon in a biomass sample after thermochemical processing under standardized conditions, as outlined in ASTM method D3175. Fixed carbon is also known as "coke."

"Glucan," "Xylan" and "Arabinan" refer to the anhydro forms of glucose, xylose and arabinose that are found in cellulose and hemicellulose carbohydrate polymers. Thus, for example, "glucan" refers to a polysaccharide of D-glucose monomers linked by glycosidic bonds. The following are glucans: cellulose (β-1,4-glucan), dextran (α-1,6-glucan) and starch (α-1,4- and α-1,6-glucan).

"Hemicellulose" is a general term used to refer to cell wall polysaccharides that are not celluloses or pectins. Hemicelluloses contain repeating monomeric units of a five-carbon sugar (usually D-xylose or L-arabinose) and/or a six-carbon sugar (D-galactose, D-glucose, and D-mannose). See, U.S. Pat. No. 7,112,429. Hemicelluloses typically are shorter in length than cellulose and are highly branched. Xylan is often the structural backbone of hemicelluloses from hardwoods and grasses, and hydrolysis of these biomass types releases products high in the five-carbon sugar, xylose. Hemicelluloses from softwoods are most commonly gluco-galacto-mannans, which have a mannan backbone and yield mannose as the main product of hydrolysis. Hemicelluloses often contain side groups such as acetyl groups, uronic acids and ferulates.

"Higher heating value" (HHV) refers to the amount of heat released by a specified quantity of a fuel at an initial temperature of 25° C., following combustion, and return of the combustion products to a temperature of 25° C. The HHV is also known as the gross calorific value or gross energy.

"Lignin" refers to a polyphenolic polymeric substance of plant cells, with a complex, cross-linked, highly aromatic structure. Lignin is synthesized in plants principally from three monolignol monomers, which can be methoxylated to various degrees: sinapyl alcohol ($C_{11}H_{14}O_4$) that is incorporated into lignin as (S) syringyl units; coniferyl alcohol ($C_{10}H_{12}O_3$) that is incorporated into lignin as (G) guaiacyl units; and p-coumaryl alcohol ($C_9H_{10}O_2$) that is incorporated into lignin as (H) p-hydroxyphenyl units. These monomers can be synthesized into lignin by extensive condensation polymerization. The lignin present in different plant varieties can have different syringyl:guaiacyl:p-hydroxyphenyl weight percents (S:G:H weight percents). For example, certain grass varieties can have lignin composed almost entirely of guaiacyl (G). Lignin is a major structural constituent of plant cells in woody species.

"Mass Closure (%)" refers to the sum of the weight percent of all measured constituents. Examples of measured constituents are: extractives, ash, protein, total lignin, acetic acid, uronic acids, arabinan, xylan, mannan, galactan, glucan and starch. Constituent values are typically reported on a dry-weight basis. Mass closure is an indicator of the accuracy of a complete biomass compositional analysis.

"NIR Model" refers to a series of validated mathematical equations that predict one or more properties of a sample based on NIR spectral data from the sample. The one or more properties may be: conversion efficiency, accessible carbohydrate, recalcitrant carbohydrate, lignin, S, G, or H weight percents, saccharification efficiency or sugar yield (Glu, Xyl, Ara, Man, Gal), product extraction/conversion efficiency or yield, biofuel conversion efficiency or yield, co-product extraction efficiency or yield, ethanol conversion efficiency or yield, higher heating value (HHV), fixed carbon, ash, C:H:O weight percents, enzymatic conditions (type, ratio, load) for saccharification, pretreatment conditions, fermentation conditions, economic value, ferulate and acetate content, NOX emissions, protein coproducts, sustainability indicators, and/or correlations of any of the previous parameters to specific transgene sequences, genetic markers, or genetic loci. In many cases, a different NIR model is developed for each combination of processing steps, such as pretreatment conditions and enzyme(s).

"NIR Model Application" refers to a computer application for making use of one or more NIR models. A NIR model application accepts as input a representation of NIR characteristics of a sample, and processes it by applying the NIR model to output a representation of the predicted properties of the sample. A NIR model application may also comprise additional input and/or output modules. For example, an input module may allow a user to specify a feedstock species, cultivar, or genetic marker profile, and/or available enzymes for biochemical processing, thus directing the NIR model application to select the most accurate NIR model. An output module may allow further processing of the predicted properties of the sample to a desired format. For example, an output module may transform a representation of recalcitrant carbohydrate and total carbohydrate into gallons of ethanol per acre of feedstock or into monetary value per ton of feedstock.

In the case of saccharification efficiency, a different NIR model is developed for each combination of pretreatment conditions and enzyme(s). NIR spectral data typically is obtained from the sample at a plurality of different wavelengths, and the mathematical equations are applied to the spectral data to calculate the predicted value. The calibration equations can be derived by regression among spectroscopic data for feedstock samples of the same type, e.g., by multiple-linear regression, by partial least squares, or by neural network analysis.

"NOX emissions" refers to mono-nitrogen oxides ($NO_x$), such as NO and $NO_2$, released into the atmosphere. While oxygen and nitrogen gases do not typically react at ambient temperatures, oxygen and nitrogen gases can react at higher temperatures to create various oxides of nitrogen, including mono-nitrogen oxides. Mono-nitrogen oxides can also be produced by combusting materials including elemental nitrogen. Mono-nitrogen oxides ($NO_x$) released into the atmosphere can react with volatile organic compounds to produce smog. Accordingly, NOX emissions may be regulated by various governmental agencies. Oxides of sulfur ($SO_x$), specifically sulfur dioxide, are often generated in the same processes. $SO_x$ emissions are known to contribute to acid rain.

"Pectin" refers to a polysaccharide having a backbone of α-(1-4)-linked D-galacturonic acid residues, with regions of 1,2-linked L-rhamnose. Side chains containing arabinose, xylose and galactose are present depending on the source material. Polygalacturonans, rhamnogalacturonans and some arabinans, galactans and arabinogalactans are pectins. Pectins are typically found in the middle lamella and primary wall of plant cells.

"Predicting" is a term used in the field of statistics to designate determination made using a model as distinguished from a direct calibration.

"Product" refers to the final product of plant biomass processing which is used by consumers or industry. Plant biomass-derived products include energy, liquid transportation fuel, biofuel, automotive fuel, jet fuel, ethanol, coproducts, biopower, heat, and electricity.

"Protein" refers to a polymer of amino acids linked by amide bonds. A protein can contain up to several hundred amino acids. In their biologically active states, proteins function as catalysts in metabolism and to some extent as structural elements of cells and tissues. Protein can provide nutritional value in animal feed. Protein content in biomass can be estimated by multiplying the mass % nitrogen of the sample by a conversion factor.

"Recalcitrant carbohydrate material" refers to mono- and oligo-saccharides that are not released into the aqueous phase after processing of a biomass feedstock. It is related to the pretreatment and enzymatic saccharification conditions chosen for the saccharification process.

"Saccharification" refers to the hydrolysis of carbohydrate material to the mono- and disaccharides that constitute the polymer. For example, saccharification of xylan results in the production of xylose, the monosaccharide constituent of xylan. Saccharification occurs during the biochemical processing of biomass in biorefineries, ultimately leading to the production of biofuels such as ethanol.

"Saccharification efficiency" of a feedstock sample refers to the total amount of mono and disaccharides solubilized by pretreatment/enzymatic saccharification processes, divided by the theoretical maximum amount of mono and disaccharides in the biomass sample that could have been released based on compositional analysis, converted to a percentage by multiplying by 100.

"Sustainability indicators" refer to components of biomass processing byproducts, such as the expected ash composition and soil nutrients, which may be recycled.

"Thermochemical processing" refers to a non-biological process by which plant materials are converted to liquid products, power and/or heat using high temperatures and pressures.

3. NIR Models for Assessment of Plant Biomass 3.1 NIR Models for Biochemical Processing of Feedstocks It has been discovered that NIR models can be developed for complex lignocellulosic feedstocks that correlate patterns in spectroscopic data with the compositional and biofuel conversion performance characteristics of a feedstock. In these models, validated mathematical correlations are established between NIR spectra and independently determined chemical constituents using multivariate statistical regression methods, preferably Principal Component Analysis (PCA) and Projection to Latent Structures (PLS; see, e.g., Martens H. and Naes T., *Multivariate Calibration*, Wiley & Sons, New York (1989); Hoskuldsson A., *J. Chemometrics*, 2:211-228 (1988); Geladi P. and Kowalski B. R., *Analytica Chimica Acta*, 185: 1-17 (1986) and Wold S. et al., *Chemometrics Intelligent Laboratory Systems*, 2:37-52 (1987)). Properly constructed models of this sort robustly and accurately reflect the true chemical composition and/or biofuel conversion characteristics of the feedstock sample. For example, a NIR model designated SWG_2 was developed in which PLS equations were obtained that convert spectroscopic data from switchgrass feedstock samples directly into compositional information.

A NIR model is typically developed from a single type of biomass, i.e., herbaceous, hardwood or softwood types. A NIR model is usually developed using a single species of biomass, i.e., corn stover, poplar wood chips, etc. In order to obtain diverse compositional profiles and thus a representation of the variability in composition for the type of biomass under consideration, samples are collected from many different sources. For example, biomass samples may be collected from plants at different stages in development, e.g., early vegetative, mid-vegetative, and fully senesced plants. Samples may be collected representing different anatomical fractions, e.g., leaves, stalks and nodes. Samples may be collected from genetically different varieties, different geographic locations and different harvest years. Biomass is often a heterogeneous material, and preparation of biomass samples according to techniques such as ASTM method E1757-01 can facilitate collection of NIR spectral data representative of the sample.

A NIR model is formulated by subjecting a plurality of plant feedstock samples of the same type to near infrared spectroscopy, to produce NIR spectroscopic data from each sample. Multivariate statistical techniques are used to identify a subset of the plurality of samples from which NIR data were obtained that span the variance space described by all of the samples. This subset is designated the calibration set. A similar, non-overlapping set of samples is set aside as the validation set. The composition of each feedstock sample in the calibration set is measured by independent analytical chemistry techniques, typically standard wet chemical techniques. Components that are typically useful to measure for biochemical processing include, without limitation, glucan, xylan, arabinan, lignin, protein and ash. For biochemical processing via pretreatment coupled with enzymatic saccharification, the saccharification efficiency of each feedstock calibration sample can be measured when processed by a defined set of pretreatment and enzyme loading conditions. A NIR model is then generated from the spectroscopic data, wet chemical composition data and saccharification efficiency data by regressing the spectral data against the wet chemical composition data and the saccharification efficiency data, for example, by multivariate analysis of the data and validating calibration equations derived therefrom. Although mathematical treatments are not necessary for the development of a NIR model, they are often employed to minimize non-constituent variables. Common mathematical treatments include scatter correction and baseline adjustments that minimize scatter effects due to path length variations, and non-uniform particle sizes in the samples.

Once the calibrated NIR model is built, it is independently validated using the validation set of samples. The NIR spectra of the validation samples is first used to produce composition and conversion values for those samples. Then, chemical analysis of the validation samples is carried out using standard analytical techniques, and the NIR values are compared with those from the wet chemical analysis. If the two sets of data from the validation samples agree within the limits of the standard deviation of the primary methods used to obtain the calibration data, then the model is considered validated. For thermochemical processing, the higher heating value (HHV) and the amount of fixed carbon in each feedstock sample is measured by thermochemical techniques. A NIR model is then generated from the spectroscopic data, chemical composition data and thermochemical data by regressing the spectral data against the chemical composition data and the thermochemical data, for example, by multivariate analysis of the data and validating calibration equations derived therefrom. The model is further validated as described above.

Suitable NIR instruments for collecting NIR spectral data from feedstock samples are known. FT-NIR (Fourier transform near-infrared) spectroscopy is one of several related spectroscopic techniques that can provide spectral data in a sensitive, non-invasive and high-throughput manner. FT-NIR spectrometers use interferometers, which split the source light into a beam that is reflected off a fixed mirror and a beam that is reflected off an oscillating mirror. The two beams are then recombined to create an interferogram, and a Fourier Transform is applied to produce a spectrum. See, e.g., U.S. Pat. Nos. 5,499,095 and 6,137,108. Examples of NIR instruments include the Bruker Optics MPA™ FT-NIR spectrometer (Bruker Optics, Ettlingen, Germany), and the Foss NIR-Systems Spectrometers (Denmark). Field-mobile spectrometers are available from Analytical Spectral Devices (Boulder, Colo., USA), Ocean Optics (Dunedin, Fla.), Polychromix (Wilmington, Mass.) and others. Real-time and near real-time instruments can also be used (see, e.g., U.S. Pat. No. 6,483,583 and EP 1 894 461 A1). Spectral information is collected from visible and NIR wavelengths, typically in the range of 400 to 2500 nm.

The chemical composition of the selected biomass type can be determined by established methods, e.g., ASTM methods E1758-01, E1721-01 and E1755-01, and US Department Of Energy/Energy Efficiency and Renewable Energy (DOE/EERE) methods *Determination of Protein Content in Biomass and Determination of Extractives in Biomass*. Hames, et al., NREL/TP-510-42625, January 2008, and Sluiter, et al., NREL/TP-510-42619, January 2008, both available from the National Renewable Energy Laboratory. Thermochemical methods for determining Higher Heating Values and fixed carbon can be determined by standard methods known in the art, e.g. ASTM methods D5865-07a, D3175-07, D3176-89 (2002) and D3172-07a, available from ASTM International, West Conshohocken, Pa., US.

NIR spectral data typically is obtained from the sample at a plurality of different wavelengths, and the mathematical equations are applied to the spectral data to calculate the predicted value. The calibration equations can be derived by regression among spectroscopic data for feedstock samples of the same type, e.g., by multiple-linear regression, by partial least squares, or by neural network analysis.

Enzymatic processing conditions are defined by the type of enzymes used and the amount of each enzyme(s) used during the saccharification process in a biorefinery. For example, an enzymatic processing condition can entail the use of a single enzyme preparation such as Spezyme® CP (Genencor, USA) or Celluclast 1.5L (Novozymes, Franklinton, N.C.). Spezyme® CP and Celluclast 1.5L are commercially available enzyme mixtures containing cellulases that are prepared by submerged culture fermentation of the filamentous fungus, *Trichoderma reesei*. These cellulase preparations are deficient in β-glucosidase activity, so they are often supplemented with a β-glucosidase preparation such as Novozyme 188, obtained by submerged culture fermentation of *Aspergillus niger*. Novozyme 188 is available from Sigma (St. Louis, Mo., USA) as catalogue number C6105. NIR models can also be developed for the following examples of other enzymes: β-1,4-endoglucanases (EG I, EG II, EG III, and EG V); β-1,4-cellobiohydrolases (CBH I & CBH II); xylanases (XYN I & XYN II); β-glucosidase; α-L-arabinofuranosidase; acetyl xylan esterase; β-mannanase; and α-glucuronidase. In some embodiments, a NIR model is developed for an enzymatic processing condition that includes the use of two types of enzyme. For example, a NIR model can be developed for an enzymatic processing condition that includes the use of Spezyme® CP in combination with a xylanase. See, e.g., U.S. Pat. No. 5,874,274; U.S. Pat. No. 6,333,181 and U.S. Patent Publication 2007/0092935. Enzyme cocktails containing a plurality of enzymes are sometimes used in biomass processing, such cocktails differing from each other in the type and amount of each enzyme. It will be appreciated that a NIR model can be developed for each such cocktail and each type of biomass. Thus, for example, a NIR model is developed for an enzymatic processing condition that includes the use of three enzymes, an endo-β-(1,4)-glucanase (EC 3.2.1.4), an exo-β-(1,4)-glucanase (EC 3.2.1.91) and a β-D-glucosidase (EC 3.2.1.21). See, U.S. Pat. No. 7,059,993.

Biomass processing sometimes includes a pretreatment before enzymatic processing. A typical pretreatment is a dilute-acid thermochemical pretreatment, which partially or completely hydrolyzes the hemicellulose and can also hydrolyze some of the lignin. See, e.g., U.S. Pat. No. 6,090,595. NIR models can be developed for such procedures. Thus, in some embodiments, a NIR model is generated that predicts saccharification efficiency for a feedstock when a pretreatment is used before enzymatic processing.

Saccharification conversion is determined and conversion efficiency is calculated by known techniques. Saccharification efficiency can be calculated for individual monosaccharides, e.g., glucose conversion efficiency, for combinations of monosaccharides, e.g., glucose+xylose conversion efficiency, or for all monosaccharides. The choice of mono and disaccharide(s) for which saccharification efficiency is calculated in a particular NIR model is based on factors such as the type of biomass to be processed, and the capability of the conversion process to use all or just some of the sugars made available for fermentation.

Once a NIR model has been generated, the model can be applied to a biomass test sample to rapidly predict various parameters and characteristics useful for biofuel production. For example, the amount of accessible carbohydrate material in a test sample can be predicted by collecting NIR spectral data from a feedstock sample to be tested, applying a NIR model of accessible carbohydrate in feedstocks of the same type as the sample to the spectral data and predicting the amount of accessible carbohydrate material in the test sample, based on the output of the model. As another example, a NIR model as described herein permits the saccharification efficiency of a feedstock sample to be predicted by collecting NIR spectral data from a feedstock sample to be tested, applying a NIR model of accessible carbohydrate in feedstocks of the same type as the sample to the spectral data, and predicting the saccharification efficiency of the sample based on the output of the model. It will be appreciated that the amount of accessible carbohydrate material and the saccharification yield are mathematically interconvertible values. Thus, a NIR model that is capable of predicting one value is readily modified to predict the other value. Similarly, a NIR model can be generated that predicts the amount of recalcitrant carbohydrate material in a feedstock sample, i.e., the difference between total carbohydrate material and accessible carbohydrate material.

It will be appreciated that the amount of accessible carbohydrate material in a feedstock may be different if the feedstock is processed by a second defined pretreatment/enzymatic loading condition. Thus, two, three, or more NIR models are typically generated from a given feedstock, each model related to a different defined pretreatment/enzymatic loading condition.

In some embodiments, a NIR model is developed that predicts the efficiency with which biomass is saccharified under a defined pretreatment and/or enzyme load combination. A series of such models can be used to determine optimum conditions for biorefinery processing of a feedstock having a particular composition profile. In some embodiments, a NIR model is generated to predict pretreatment/enzyme loading conditions for biomass processing that are optimized for either product yield or process profitability. For example, NIR spectral data from a test feedstock sample can be collected, and one or more NIR models of accessible carbohydrate in feedstocks of the same type as the sample are applied to the spectral data. Based on the results of the application of the model, pretreatment/enzyme loading conditions that produce maximum saccharification of the feedstock sample are identified. As another example, a biorefinery can collect NIR spectral data after pretreatment of a feedstock batch and predict average accessible carbohydrate using NIR models for that type of biomass and different saccharification conditions. The saccharification condition that is most economical or gives the greatest biofuel production can then be selected. It is also contemplated that NIR spectral data can be collected during saccharification and used in NIR models to modify saccharification conditions in "real time," whether the process is batch saccharification, semi-continuous saccharification or continuous saccharification. Thus, biorefineries can identify pretreatment conditions and/or enzyme cocktails that optimize biomass processing for maximum economic output. See, e.g., US Patent Publication 2003/0092097.

3.2 NIR Models for Thermochemical Processing of Feedstocks

Thermochemical processing conditions are defined by the amount of oxygen present, the processing temperature, and processing time in the reaction zone of the biorefinery. Depending on the conditions selected, thermochemical processing results in either 1) complete degradation of biomass polymers to carbon monoxide (CO) and hydrogen (H2) (i.e., synthesis gas or syngas), a process known as gasification, or 2) partial breakdown of the biomass polymers to pyrolysis oil, a process known as pyrolysis. In hybrid thermochemical processes, biofuels are produced from syngas or producer gas subjected to fermentation, for example by anaerobic or facultative acetogenic bacteria such as *Acetogenium kivui*, *Acetobacterium woodii*, *Acetoanaerobium noterae*, *Clostridium aceticum*, *Butyribacterium methylotrophicum*, *Clostridium acetobutylicum*, *Clostridium thermoaceticum*, *Eubacterium limosum*, *Clostridium ljungdahlii* PETC, *Clostridium ljungdahlii* ER12, *Clostridium ljungdahlii* C-01, *Clostridium ljungdahlii* O-52, and *Peptostreptococcus productus*. See, e.g. U.S. Pat. No. 7,285,402, US Pub Nos. 20070275447 and 20080057554, and Datar et al. (2004) Biotechnology and Bioengineering, v. 86, no. 5, 587-594.

For example, a thermochemical processing condition can be the use of a fluidized-bed reactor for pyrolysis, in which biomass is pyrolyzed in the reactor in the absence of oxygen, followed by gasification of the pyrolysis vapors to synthesis gas by introducing steam in a multi-stage process in order to provide hydrogen and the proper amount of oxygen to carry out the gasification. Heat for the process is provided by burning the char. As another example, a thermochemical processing condition can be the use of a screw auger reactor, in which moisture, and thus oxygen, is introduced at the pyrolysis stage. Heat for the process is provided by burning some of the gas produced in the pyrolysis stage. In yet another example, a thermochemical processing condition can be the use of a fluidized-bed reactor and a single-stage gasification reactor in which external steam and air are introduced in an entrained flow during gasification.

NIR models can be developed for thermochemical processes in an analogous manner as described for biochemical processes. Similar to biochemical processes, a pretreatment is sometimes used before thermochemical processing and NIR models can be developed for such procedures as well. See, e.g., U.S. Pat. No. 4,982,027. Thus, in some embodiments, a NIR model is generated that predicts thermochemical processing efficiency for a feedstock when a pretreatment is used with a particular thermochemical processing condition.

Once a NIR model has been generated, the model can be applied to a biomass test sample to rapidly predict various parameters and characteristics useful for biofuel production or for heat/electricity generation. For example, the amount of fixed carbon in a test sample can be predicted by collecting NIR spectral data from a feedstock sample to be tested, applying a NIR model of fixed carbon in feedstocks of the same type as the sample to the spectral data and predicting the amount of fixed carbon in the test sample, based on the output of the model. As another example, a NIR model as described herein permits the pyrolysis efficiency/yield of a feedstock sample to be predicted by collecting NIR spectral data from a feedstock sample to be tested, applying a NIR model of fixed carbon in feedstocks of the same type as the sample to the spectral data, and predicting the amount of volatile material in the sample based on the output of the model. It will be appreciated that the amount of fixed carbon and the amount of volatile material are mathematically interconvertible values. Thus, a NIR model that is capable of predicting one value is readily modified to predict the other value. These values can then be correlated with the energy content of the feedstock allowing a prediction of the heat, electricity, or biofuel yield and/or conversion efficiency upon thermochemical processing of the feedstock.

In some embodiments, a NIR model is developed that predicts product yields from biomass gasification under defined thermochemical processing conditions. Such a model can be used to predict product yields for biorefinery processing of a feedstock having a particular composition profile. For example, NIR spectral data from a test feedstock sample can be collected, and one or more NIR models of fixed carbon in feedstocks of the same type as the sample are applied to the spectral data. Based on the results of the application of the model, thermochemical processing conditions that produce maximum gasification of the feedstock sample are identified. As another example, a biorefinery can collect NIR spectral data after pretreatment of a feedstock batch and predict average product yields and/or conversion efficiencies using NIR models for that type of biomass and different thermochemical processing conditions. The thermochemical processing condition that is most economical and/or efficient (e.g., gives the greatest biofuel production) can then be selected. It is also contemplated that NIR spectral data can be collected during gasification and used in NIR models to modify thermochemical processing conditions in "real time." Thus, biorefineries can identify pretreatment conditions and/or processing conditions that optimize biomass processing for maximum economic output.

3.3 NIR Models for Biomass to Heat and Electricity Processing of Feedstocks

Thermochemical processing conditions are defined by the amount of oxygen present, the processing temperature, and processing time in the reaction zone of the biorefinery. Depending on the conditions selected, thermochemical processing results in either 1) complete degradation of biomass polymers to carbon monoxide (CO) and hydrogen ($H_2$) (i.e., synthesis gas or syngas), a process known as gasification, or 2) partial breakdown of the biomass polymers to pyrolysis oil, a process known as pyrolysis. Thermochemical processes designed to produce electricity and heat take the former (i.e., syngas) approach. After production of syngas, hydrogen is purified away from other non-combustible gases and is burned to generate additional heat, which is used to fire steam generators that make electricity, much like what is done today in modern coal-fired electric utilities.

For these processes, HHV and fixed carbon are important parameters relating to feedstock quality. NIR models to estimate these parameters are created and validated as described in Section 3.2.

4. Feedstocks for NIR Models

As mentioned above, NIR models are developed for use with a single type of biomass. Thus, NIR models can be generated for feedstocks of monocotyledonous and dicotyledonous plants, whether a herbaceous, hardwood or softwood type, that are known or expected to be useful for producing fuels such as ethanol. Species from the following families are known or expected to be useful: Acanthaceae, Alliaceae, Alstroemeriaceae, Amaryllidaceae, Apocynaceae, Arecaceae, Asteraceae, Berberidaceae, Bixaceae, Brassicaceae, Bromeliaceae, Cannabaceae, Caryophyllaceae, Cephalotaxaceae, Chenopodiaceae, Colchicaceae, Cucurbitaceae, Dioscoreaceae, Ephedraceae, Erythroxylaceae, Euphorbiaceae, Fabaceae, Lamiaceae, Linaceae, Lycopodiaceae, Malvaceae, Melanthiaceae, Musaceae, Myrtaceae, Nyssaceae, Papaveraceae, Pinaceae, Plantaginaceae, Poaceae, Rosaceae, Rubiaceae, Salicaceae, Sapindaceae, Solanaceae, Taxaceae, Theaceae, or Vitaceae. Suitable genera include *Panicum* spp., *Sorghum* spp., *Miscanthus* spp., *Saccharum* spp., *Erianthus* spp. *Salix* spp., *Eucalyptus* spp. and *Populus* spp. Thus, suitable plant species include *Panicum virgatum* (switchgrass), *Sorghum bicolor* (sorghum, sudangrass), *Miscanthus giganteus* (miscanthus), *Saccharum* sp. (energycane), *Populus balsamifera* (poplar), other poplar species and their hybrids, *Zea mays* (corn), *Glycine max* (soybean), *Brassica napus* (canola), *Brassica juncea, Triticum aestivum* (wheat), *Gossypium hirsutum* (cotton), *Oryza sativa* (rice), *Helianthus annuus* (sunflower), *Medicago sativa* (alfalfa), *Beta vulgaris* (sugarbeet), *Pennisetum glaucum* (pearl millet), *Andropogon gerardii* (big bluestem), *Pennisetum purpureum* (elephant grass), *Phalaris arundinacea* (reed canarygrass), *Cynodon dactylon* (bermudagrass), *Festuca arundinacea* (tall fescue), *Spartina pectinata* (prairie cordgrass), *Arundo donax* (giant reed), *Secale cereale* (rye), *Triticosecale* (wheat X rye), *Carthamus tinctorius* (safflower), *Jatropha curcas* (jatropha), *Ricinus communis* (castor), *Elaeis guineensis* (oil palm), *Linum usitatissimum* (flax), or *Manihot esculenta* (cassaya).

5. NIR Model Parameters and Applications

As explained in more detail below, NIR models are useful for a variety of applications. For example, NIR models can be used in methods for: predicting feedstock composition, biofuel conversion characteristics, choosing between available biochemical and/or thermochemical processing alternatives, selecting feedstock for processing, selecting variety for processing, selecting individuals plants from a population, plant breeding, valuing feedstock, defining optimum processing conditions, real-time analyses and feedback for process adjustment, predicting biofuel yield, predicting product yield, managing biorefinery operations, managing a supply chain for a biorefinery, and influencing biorefinery design. NIR models can be made available to users in various ways, such as computer applications or instrument firmware.

5.1 Predicting Composition

In some aspects the invention relates to methods for predicting feedstock composition, such as total carbohydrate, accessible carbohydrate, recalcitrant carbohydrate, glucan, xylan, arabinan, mannan, galactan, lignin, ferulate, acetate, nitrogen, protein, fixed carbon, ash, and elemental composition content. In addition, lignin subunit amounts (S:G:H weight percents), carbon:hydrogen:oxygen (C:H:O) weight percents, and higher heating value (HHV) can be predicted. All of these compositional parameters can be correlated, or linked, to specific transgene sequences, natural sequence polymorphisms, genetic markers, or genetic loci. Accordingly, NIR spectra of biomass samples are collected and used in a NIR model. The result could be a direct prediction of one or more feedstock composition properties, one or more intermediate values that may serve for predicting feedstock composition, or one or more downstream parameters that are influenced by feedstock composition. Predictions of composition may be used to calculate the feedstock performance characteristics in one or more processing methods of interest. Such performance characteristics include saccharification efficiency or sugar yield (Glu, Xyl, Ara, Man, Gal), various enzymatic conditions (type, ratio, load) for saccharification, pretreatment conditions, total or net energy yield or energy conversion efficiency, biopower yield or conversion efficiency, biofuel yield or conversion efficiency, coproduct yield or extraction/conversion efficiency, economic value of the original feedstock, NOX emissions, protein coproducts, or sustainability indicators.

5.2 Predicting Conversion

In some aspects the invention relates to methods for predicting feedstock conversion efficiency. Conversion efficiency may be in terms of the conversion of biomass feedstock to free sugars, fermentable sugars, syngas, biofuel, ethanol, heat, or energy in a laboratory-, pilot-, or production-scale process. The relevant conversion efficiency parameters are dependent on the type of conversion process employed (biochemical, thermochemical to biofuel, or thermochemical to heat and electricity). All of these conversion parameters can be correlated, or linked, to specific transgene sequences, natural sequence polymorphisms, genetic markers, or genetic loci. Accordingly, NIR spectra of biomass samples are collected and translated by a NIR model. The result could be a direct prediction of feedstock conversion properties (such as free sugars or accessible carbohydrate), one or more intermediate values that may serve for predicting feedstock conversion properties (such as recalcitrant carbohydrate), or one or more downstream parameters that are influenced by feedstock conversion efficiency (such as biofuel or energy yield) Predictions of conversion properties may be used to calculate the feedstock performance characteristics in one or more processing methods of interest. Such performance characteristics include saccharification efficiency or sugar yield (Glu, Xyl, Ara, Man, Gal), various enzymatic conditions (type, ratio, load) for saccharification, pretreatment conditions, total or net energy yield or energy conversion efficiency, biofuel yield or biofuel conversion efficiency, biopower yield or biopower conversion efficiency, coproduct yield or extraction/conversion efficiency, economic value of the original feedstock, NOX emissions, protein coproducts, or sustainability indicators.

5.3 Selecting Feedstock (Species and/or Variety)

In some aspects the invention relates to methods for selecting a plant species that has desirable composition or conversion characteristics for a biomass feedstock. Accordingly, NIR spectra of biomass samples are collected and translated by a NIR model to predict composition or conversion characteristics, or product or biofuel yield of the different plant species under consideration. Comparison of composition or conversion characteristics, or product or biofuel yields relevant to a particular conversion process under consideration may allow the selection of biomass feedstocks particularly well-suited for use in that process. The selected plant species may require less resources (heat, energy, reagents, enzymes, catalysts) to process, yield higher amounts of product (biofuel, biopower, heat, electricity, energy, or coproducts), thus improving the economics of the process of converting plant biomass to products. Desirable species may also be selected by detection of specific transgene sequences, natural sequence polymorphisms, genetic markers, or genetic loci that have been associated with desirable composition or conversion characteristics, or product or biofuel yield.

In some aspects the invention relates to methods for selecting a variety, cultivar, inbred, hybrid, line, or genotype of a plant biomass feedstock that has desirable composition or conversion characteristics. Accordingly, NIR spectra of biomass samples are collected and translated by a NIR model to predict composition or conversion characteristics of plant varieties, cultivars, inbreds, hybrids, lines, or genotypes under consideration. Comparison of composition or conversion characteristics relevant to a particular conversion process under consideration may allow the selection of biomass feedstocks particularly well-suited for use in that process. A selected variety, cultivar, inbred, hybrid, line, or genotype may require less resources (heat, energy, reagents, enzymes, catalysts) to process, yield higher amounts of product (biofuel, biopower, heat, electricity, energy, or coproducts), thus improving the economics of the process of converting feedstock to products. A variety, cultivar, inbred, hybrid, line, or genotype may also be selected by detection of specific transgene sequences, natural sequence polymorphisms, genetic markers, or genetic loci that have been associated with desirable composition and conversion characteristics. Specific transgene sequences that confer a desired alteration in biomass composition and/or conversion characteristics can be identified by screening model plants that contain those transgenes, using NIR models as described herein. Suitable model plants include, without limitation, *Arabidopsis, Brachypodium* and rice.

5.4 Selecting from a Population

In some aspects the invention relates to methods for selecting individuals from a genetically diverse population of a variety, cultivar, inbred, hybrid, line, or genotype of a plant biomass feedstock that has desirable composition or conversion characteristics. Accordingly, NIR spectra of biomass samples of individual plants are collected and translated by a NIR model to predict composition or conversion characteristics of the individuals under consideration. Comparison of composition or conversion characteristics of interest amongst individuals in the genetically diverse population may allow the selection of unique genotypes that are particularly well-suited for biomass to energy production systems. Selected individuals may be sexually or vegetatively propagated to develop a new variety, cultivar, inbred, hybrid, line, or genotype which may require less resources (heat, energy, reagents, enzymes, catalysts) to process, yield higher amounts of product (biofuel, biopower, heat, electricity, energy, or coproducts), thus improving the economics of the process of converting feedstock to products. Selected individuals may be used as parents in genetic crosses or in a polycross to develop a new variety, cultivar, inbred, hybrid, line, or genotype which may require less resources (heat, energy, reagents, enzymes, catalysts) to process, yield higher amounts of product (biofuel, heat, energy, or coproducts), thus improving the economics of the process of converting feedstock to products.

5.5 Plant Breeding

In some aspects the invention relates to methods for breeding plants with desirable composition or conversion characteristics that would make them more valuable as dedicated biofuel feedstocks. Accordingly, NIR spectra of biomass samples from individual plants in a breeding population are collected and translated by a NIR model to predict composition or conversion characteristics. NIR models can be used to select for breeding plants predicted to have desirable attributes related to conversion efficiency. Conversion efficiency may be in terms of saccharification efficiency, the conversion of biomass feedstock to free sugars, fermentable sugars, syngas, biofuel, ethanol, heat, energy, or product in a laboratory-, pilot-, or production-scale process. The relevant conversion efficiency parameter(s) are dependent on the type of conversion process employed (biochemical, thermochemical to biofuel, or thermochemical to biopower, heat and electricity). Composition characteristics include total carbohydrate, accessible carbohydrate, recalcitrant carbohydrate, glucan, xylan, arabinan, mannan, galactan, lignin, ferulate, acetate, nitrogen, protein, fixed carbon, ash, and elemental composition content or yield. In addition, syringyl:guaiacyl: p-hydroxyphenol (S:G:H weight percents), carbon:hydrogen:oxygen (C:H:O) weight percents, and higher heating value (HHV) can be predicted. All of these conversion and compositional parameters can be correlated, or linked, to specific transgene sequences, natural sequence polymorphisms, genetic markers, or genetic loci which may be useful in accelerating the plant breeding process using the approach of marker assisted breeding. Selection of breeding parents with desirable biomass composition or conversion characteristics may be used in conjunction with marker assisted breeding, resulting in accelerated development of superior germplasm for dedicated bioenergy feedstocks.

In some aspects the invention relates to methods for breeding plants which allow favorable enzymatic conditions (type, ratio, load) for saccharification, pretreatment conditions, economic value, NOX emissions, protein coproducts, sustainability indicators when employed in a biomass to fuels, biopower, or energy processing system. Selection of breeding parents with the above desirable biomass characteristics may be used in conjunction with marker assisted breeding, resulting in accelerated development of superior germplasm for dedicated bioenergy feedstock.

Thus, a method of breeding a plant variety comprises crossing two or more parent biomass plants and selecting progeny of the cross that have higher saccharification efficiency relative to the saccharification efficiency of at least one of the parents.

Techniques suitable for use in a plant breeding program are known in the art and include, without limitation, backcrossing, polycrossing, mass selection, pedigree breeding, bulk selection, crossing to another population and recurrent selection. These techniques can be used alone or in combination with one or more other techniques in a breeding program.

The number of plants used in the initial cross is chosen based on the biology of the species to be used in the method and on breeding programs suitable for that species. Any of the monocotyledonous and dicotyledonous plants mentioned above can be used in the breeding methods described herein. Plants such as switchgrass, sorghum or sudangrass, miscanthus, energycane, poplar, corn, cassaya, soybean, canola, safflower, jatropha, castor, palm, triticale, wheat, cotton, rice, sunflower, alfalfa, sugarcane, sugarbeet, tall fescue, reed canarygrass, prairie cord-grass, Bermuda grass, elephant grass, big bluestem, giant reed, rye, flax, or pearl millet are particularly suitable. Breeding techniques applicable to various biomass species are known in the art. See, e.g., Allard, *Principles of Plant Breeding*, John Wiley & Sons, Inc. (1960); Simmonds, *Principles of Crop Improvement*, Longman Group Limited (1979); and, Jensen, *Plant Breeding Methodology*, John Wiley & Sons, Inc. (1988). For example, breeding techniques applicable to open-pollinated species such as switchgrass are known. See, e.g., Vogel and Jung, *Critical Rev. Plant Sci.* 20:15-49 (2001).

Progeny of the cross of parental plants are screened for those that have higher accessible carbohydrate levels. Progeny that can be screened include descendants of $F_1$, $F_2$, $F_3$, $F_4$, $F_5$, $F_6$ and subsequent generation plants, $BC_1$, $BC_2$, $BC_3$, and subsequent generation plants, or $F_1BC_1$, $F_1BC_2$, $F_1BC_3$, and subsequent generation plants. Thus, the selecting step can include collecting NIR spectral data from a feedstock sample from each of one or more progeny plants, applying a NIR model of accessible carbohydrate in feedstocks of the same type as the sample, and predicting the saccharification efficiency of the sample. Those progeny that have a predicted increase in saccharification efficiency relative to the predicted saccharification efficiency of at least one of the parent plants are selected for further breeding.

Selection using predicted levels of accessible carbohydrate from NIR models can be applied beginning with the $F_1$ generation progeny, or can be applied beginning with progeny of a subsequent generation. For example, an open-pollinated population can utilize a program of selection with progeny testing. Examples of selection with progeny testing breeding programs for switchgrass include Restricted Recurrent Phenotypic Selection (RRPS) and Between and Within Half-Sib Family Selection (B&WFS). Alternatively, a program of mass selection can be used. In mass selection, desirable individual plants are chosen, seed harvested, and the seed composited without testing to produce the next generation. Since selection is based on the maternal parent only, and there is no control over pollination, mass selection amounts to a form of random mating with selection. Mass selection typically increases the proportion of desired genotypes in the population. Switchgrass can be used in either of these programs although selection with progeny testing is generally preferred over mass selection.

As another alternative, plants of an open-pollinated species can be used as parents in an initial cross to generate a synthetic variety. A synthetic variety is produced by crossing several parental plants. The number of parental plant varieties, populations, wild accessions, ecotypes, and the like, that are used to generate a synthetic can vary from as little as 10 to as many as 500. Typically, about 100 to 300 varieties, populations, etc., are used parents to generate a synthetic variety. Seed from the parental seed production plot of a synthetic variety can subsequently undergo one or two generations of multiplication, depending on the amount of seed produced in the parental plot before being subjected to selection as discussed herein.

Selection and/or screening can be carried out over one or more generations, and/or in more than one geographic location. In addition, selection and/or screening can be applied during a particular developmental stage in which the phenotype is expected to be exhibited by the plant. Selection and/or screening can be carried out to choose those plants having a statistically significant difference in the level of accessible carbohydrate material relative to a control plant or to the average of a control population.

In another aspect, NIR models described herein can be used to identify those members of plant populations that have higher saccharification conversion efficiencies. A population of biomass plants is provided, for example, as a collection of plants from different accessions or a synthetic population. Biomass samples from plants in the populations are screened using NIR models to determine the average saccharification efficiency of the population. One or more plants in the population that have a higher saccharification efficiency relative to the average can then be identified. In particular, plant(s) that have a statistically significantly higher saccharification efficiency are then propagated by sexual or asexual techniques. Such plants can be further evaluated for their suitability for commercial production in different geographic locations, or used in breeding programs as described herein.

In another aspect, NIR models described herein can be used in methods of identifying whether one or more genetic polymorphisms are associated with variation in the level of accessible carbohydrate material. Such methods involve determining whether genetic polymorphisms in a given population exhibit linkage with the predicted level of accessible carbohydrate material in plants of the population. If the presence of a particular allele is statistically significantly correlated with a desired difference in the predicted level of accessible carbohydrate material, the allele is associated with variation for the trait and is useful as a marker for the trait. If, on the other hand, the presence of a particular allele is not significantly correlated with the desired modulation, the allele is not associated with variation for the trait and is not useful as a marker.

Genetic polymorphisms that are useful in such methods include simple sequence repeats (SSRs, or microsatellites), rapid amplification of polymorphic DNA (RAPDs), single nucleotide polymorphisms (SNPs), amplified fragment length polymorphisms (AFLPs) and restriction fragment length polymorphisms (RFLPs). SSR polymorphisms can be identified, for example, by making sequence specific probes and amplifying template DNA from individuals in the population of interest by PCR. If the probes flank an SSR in the population, PCR products of different sizes will be produced. See, e.g., U.S. Pat. No. 5,766,847. Alternatively, SSR polymorphisms can be identified by using PCR product(s) as a probe against Southern blots from different individuals in the population. See, U. H. Refseth et al., (1997) Electrophoresis 18: 1519. The identification of RFLPs is discussed, for example, in Alonso-Blanco et al. (Methods in Molecular Biology, vol. 82, "Arabidopsis Protocols," pp. 137-146, J. M. Martinez-Zapater and J. Salinas, eds., c. 1998 by Humana Press, Totowa, N.J.); Burr ("Mapping Genes with Recombinant Inbreds", pp. 249-254, in Freeling, M. and V. Walbot (Ed.), The Maize Handbook, c. 1994 by Springer-Verlag New York, Inc.: New York, N.Y., USA; Berlin Germany); Burr et al. Genetics (1998) 118: 519; and Gardiner, J. et al., (1993) Genetics 134: 917). The identification of AFLPs is discussed, for example, in EP 0 534 858 and U.S. Pat. No. 5,878,215.

Genetic polymorphisms identified as described above can be used in a marker assisted breeding program to facilitate the development of lines that have higher levels of accessible carbohydrate material. Once a suitable genetic polymorphism is identified as being associated with variation for the trait, one or more individual plants are identified that possess the polymorphic allele correlated with the desired variation. Those plants are then advanced in a breeding program to combine the polymorphic allele with a plurality of other alleles at other loci, if any, that are correlated with the desired characteristic. The breeding program can be carried out for a number of generations as appropriate in order to achieve the desired uniformity and stability in the resulting plant variety or population, which retains the polymorphic allele(s). In most breeding programs, analysis for the particular polymorphic allele will be carried out in each generation, although analysis can be carried out in alternate generations if desired.

Plant varieties and populations obtained by the methods described herein typically have a level of accessible carbohydrate material relative to a control that is statistically significantly higher at $p \leq 0.05$ with an appropriate parametric or non-parametric statistic, e.g., Chi-square test, Student's t-test, Mann-Whitney test, or F-test. In some embodiments, the difference in the amount of accessible carbohydrate material is statistically significant at $p<0.01$, $p<0.005$, or $p<0.001$.

In some cases, selection for other useful traits is also carried out, e.g., selection for fungal resistance or drought tolerance. Selection for such other traits can be carried out before, during or after identification of individual plants that possess the desired level of accessible carbohydrate.

5.6 Product Yield

In some aspects the invention relates to methods for predicting product yield from a biomass feedstock. Relevant products derived from biomass feedstock include energy, liquid transportation fuel, biofuel, automotive fuel, jet fuel, ethanol, coproducts, biopower, heat, and electricity. Product yield may be predicted for laboratory-, pilot-, or production-scale processes. Accordingly, NIR spectra of biomass samples are collected and translated by a NIR model. The result can be a direct prediction of one or more product yields or one or more intermediate values that may be correlated to product yield(s). A NIR model for product yield produced from laboratory-scale data may be used to predict performance in a production-scale facility. Predictions of product yield may be useful for managing biorefinery or biopower generation operations, selecting preferred feedstocks for processing, placing value on delivered feedstocks, anticipating and scheduling production, and managing a supply chain. Predictions of product yield may be useful in selecting plant species, varieties, populations, or individual plants that will be most productive. Individual plants selected in this manner may be introduced into breeding programs to produce new varieties, cultivars, inbreds, and hybrids with improved product yield.

5.7 Biofuel Yield

In some aspects the invention relates to methods for predicting biofuel yield from a biomass feedstock. Biofuels are defined above and include ethanol, butanol, biodiesel, syngas, and mixed alkanes. Biofuel yield may be predicted for laboratory-, pilot-, or production-scale processes. Accordingly, NIR spectra of biomass samples are collected and translated by a NIR model. The result can be a direct prediction of biofuel yield or one or more intermediate values that may be correlated to biofuel yield. A NIR model for biofuel yield produced from laboratory-scale data may be used to predict performance in a production-scale facility. Predictions of biofuel yield may be useful for managing biorefinery operations, selecting preferred feedstocks for processing, placing value on delivered feedstocks, anticipating and scheduling production, and managing a supply chain. Predictions of biofuel yield may be useful in selecting plant species, varieties, populations, or individuals that will be most productive. Individuals selected in this manner may be introduced into breeding programs to produce new varieties, cultivars, inbreds, and hybrids with improved biofuel yield.

5.8 Valuing Feedstock (Grading)

In some aspects the invention relates to methods for placing an economic value on a plant biomass feedstock. Accordingly, NIR spectra of plant biomass samples are collected and translated by a NIR model to predict composition or conversion characteristics known to be favorable for a particular process, or a direct, or indirect, prediction of biofuel or product yield. The value of a feedstock may be determined by predictions of the feedstock's composition or conversion characteristics that reveal that reduced resources (heat, energy, reagents, enzymes, catalysts) are required for the processing of such feedstock, thus improving the overall economics. Predictions of product or biofuel yield from a plant biomass feedstock may be used to directly predict the revenue produced by processing the feedstock. The value that a farmer, wholesaler, broker, or other merchant of plant biomass feedstock is then paid for their feedstock can then be directly influenced by the value of products produced and the costs of production. The valuation of feedstock may be implemented at the gate of a biorefinery or biopower generation facility. As railcars, trucks, or barges of plant biomass arrive for processing, NIR spectra are taken and translated by a NIR model to assign a value on the basis of the overall economics of the process.

5.9 Defining Processing Costs

In some aspects the invention relates to methods for determining the cost of converting a plant biomass feedstock to product(s). The cost associated with multiple alternate processes may be determined simultaneously. Accordingly, NIR spectra of plant biomass samples are collected and translated by a NIR model to predict composition or conversion characteristics, or product or biofuel yield. These results are then used to calculate the economics associated with processing the biomass using alternate methods. The prediction of processing costs may allow a decision as to when a feedstock is most productive in a particular process. For instance, NIR spectra of a biomass feedstock may be translated by a NIR model to predict lignin content. Feedstocks above a specified lignin content may be selected for a thermochemical combustion process to generate heat and electricity for the biorefinery, while biomass samples below the specified lignin content are directed to a biochemical process to produce biofuels.

5.10 Defining Process Conditions

In some aspects the invention relates to methods for determining the conditions for converting a plant biomass feedstock to one or more products. Parameters associated with multiple alternate processes may be determined simultaneously. Accordingly, NIR spectra of plant biomass samples are collected and translated by a NIR model to predict composition or conversion characteristics. These results are then used to calculate economically important parameters (heat, energy, time, reagents, enzymes, catalysts, and feedstock loading) associated with processing the biomass into product(s) or biofuel(s). The prediction of processing conditions may allow a decision to optimize the parameters in a particular process in order to minimize processing costs thereby enhancing the economics of the biorefinery. For instance, NIR spectra of a biomass feedstock may be translated by a NIR model to predict accessible carbohydrate. Feedstocks above a specified accessible carbohydrate level may be selected for an accelerated preprocessing protocol, while biomass samples below the specified accessible carbohydrate level are processed by a more costly and time consuming process.

5.11 Real Time Analysis and Feedback

In some aspects the invention relates to methods for monitoring the biomass to products conversion process. The conversion of plant biomass to biofuels and products is a multi-step process. Chemical changes that occur during, and at each step of, the process have potential effects on subsequent steps. Composition characteristics of the biomass, preprocessed biomass, saccharification mixture, fermentation mixture, syngas, and other intermediates may be determined during, in between, or after steps in this multistep process. Accordingly, NIR spectra of biomass, preprocessed biomass, saccharification mixture, fermentation mixture, syngas, and other intermediates are collected and translated by a NIR model to predict composition or conversion characteristics. These results are then used to calculate economically important parameters (heat, energy, time, reagents, enzymes, catalysts, and feedstock loading) associated with processing the biomass into product(s) (e.g., biofuel) in the current, or subsequent steps in the process. The prediction of processing conditions may allow a decision to optimize the parameters in a particular process in order to minimize processing costs thereby enhancing the economics of the biorefinery.

5.12 Feedstock and Biorefinery Management

Figure 9:
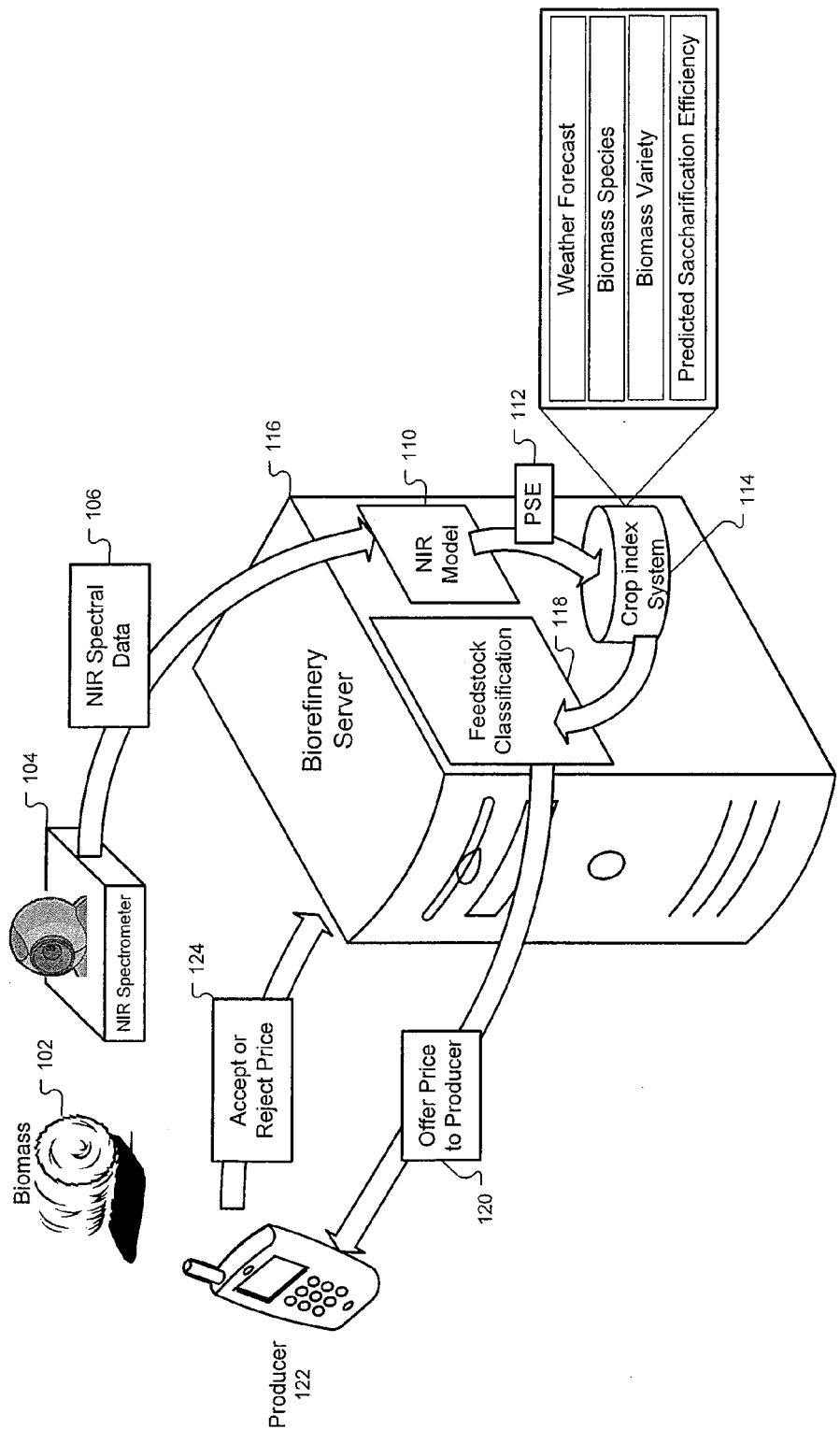
FIG. 9 is an example of a method and system for managing a feedstock supply to a biorefinery.

NIR models developed as described herein can also be incorporated into methods for managing feedstock production and supply, and/or managing biorefinery operations and economics. In some embodiments, an example of which shown in FIG. 9, NIR spectral data 106 is collected from a feedstock sample 102 to be tested using NIR spectrometer 104. A NIR model 110 of accessible carbohydrate in feedstocks of the same type as the sample is applied to the spectral data, and the saccharification efficiency 112 of the feedstock sample is predicted based on the results of the applying step. The predicted saccharification efficiency 112 is then entered into a crop index system 114 accessible by a feedstock processor such as a biorefinery, shown as server 116. The crop index system 114 can contain various data in addition to predicted saccharification efficiency 112, e.g., weather data, weather analyses, planting data, yield data and harvest information. A feedstock processor 116 is better able to manage feedstock resources, operations facilities and product distribution by accessing such information in the crop index system 114. For example, a feedstock processor 116 utilizing switchgrass as a source of biomass may require less biomass when incoming lots of biomass are predicted to have a particularly high saccharification efficiency. A processor 116 with access to a crop index system 114 can take into account predicted saccharification efficiency 112 as well as factors such as expected harvest time and geographic distance between a producer and the biorefinery, in order to more efficiently manage refinery operations. In some cases, the feedstock 102 is further classified according to feedstock quality specifications set by the feedstock processor 116, and a specified price 120 is offered to the producer 122 of the feedstock 102 based on the feedstock classification 118. For example, a feedstock processor may set a higher price for biomass having a higher predicted saccharification efficiency but also modify the price based on distance between the producer and the biorefinery. In some cases, the producer 122 may accept or reject the price 124.

Figure 10:
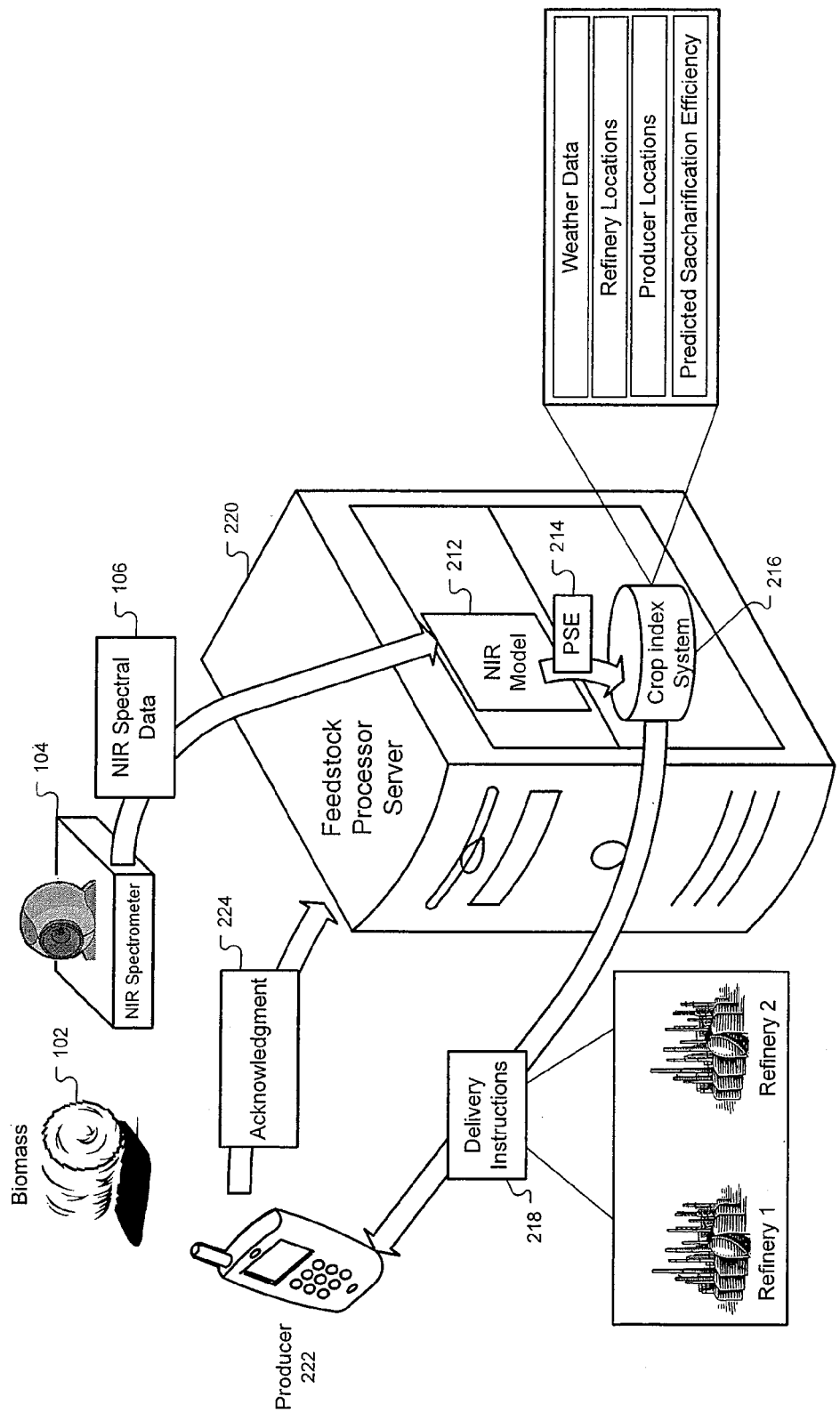
FIG. 10 is an example of a method and system for determining a feedstock supply chain distribution.

Typically, the methods described above are implemented in a computer system configured to accept NIR spectral data collected from a feedstock sample to be tested, an example of which is shown in FIG. 10. Such systems typically contain a NIR model 212 of accessible carbohydrate in feedstocks of the same type as the feedstock sample, so that the saccharification efficiency 214 of the feedstock sample can be predicted based on the application of the NIR model 212. The predicted saccharification efficiency 214 is then output for use by a crop index system 216. In some embodiments, such computer-implemented methods include receiving, in a crop index system 216, a predicted saccharification efficiency 214 of a feedstock 102. The feedstock 102 is associated in the computer system with the producer 222 who provided the feedstock. A supply chain distribution is then determined based on the predicted saccharification efficiency 214 and other information in crop index system 216, and an indication of the supply chain distribution is output 218 in a format accessible to a feedstock processor, shown as server 220. Feedstock processor 220 may then send delivery instructions to producer 222, who may acknowledge receipt of such instructions 224 and may delivery feedstock 102 according to those instructions.

A system useful in such methods includes an interface for receiving NIR spectral data from a feedstock sample, a NIR model of accessible carbohydrate in feedstocks of the same type as the feedstock sample that outputs, for use by a crop index system, a predicted saccharification efficiency of the feedstock sample based on the application of the NIR model. The crop index system is configured to determine biomass quality for feedstocks of the same type as the feedstock sample.

The invention also features a method of predicting the yield of biofuel from consolidated bioprocessing and thermochemical process conditions. The method is useful not only for predicting yield of biofuel from a biomass, but also for selecting suitable varieties in a plant breeding program and for placing a value on biomass received by a feedstock processor. Such a method involves collecting NIR spectral data from a feedstock sample to be tested. A NIR model of the HHV and/or fixed carbon of feedstocks of the same type as the sample is applied to the spectral data to determine the HHV and or fixed carbon of the feedstock sample, based on the results of the applying step. A NIR model of accessible carbohydrate in feedstocks of the same type as the sample is also applied to the spectral data and the saccharification efficiency of the feedstock sample is predicted, based on the results of the applying step. Consolidated biochemical and thermochemical processing conditions that produce a defined biofuel yield from the feedstock sample are then predicted, based on the results of the application of the NIR models.

5.13 Supply Chain Management

In some aspects the invention relates to methods for managing the supply chain of plant biomass feedstock for a biorefinery or biopower generating station. The knowledge of optimal harvesting time for biomass crops, transport distance and time, predicted processing time, and predicted product or biofuel yield will allow on-time delivery of adequate feedstock to assure the biorefinery or biopower generating station is running at optimal efficiency. Accordingly, NIR spectra of plant biomass samples are collected and translated by a NIR model to predict composition or conversion characteristics known to be favorable for a particular process, or a direct, or indirect, prediction of biofuel or product yield. This information can be collected from multiple fields growing multiple crops, and produced by multiple growers. Predictions of composition or conversion characteristics, or product or biofuel yield from a plant biomass feedstock may be made in the field in order to determine optimal harvest time. Predictions of optimal harvest time across multiple fields allows for the coordination of harvest to bring greatest value to the farmer and the biorefinery. Coordinating harvest time with transport distance and time may also allow "on-time" delivery of feedstock thus reducing the amount of on-site storage the biorefinery requires. Further, the prediction of composition or conversion characteristics and the direct, or indirect, prediction of biofuel or product yield may allow the biorefinery or biopower generating station operator to manage the quantity and quality of feedstock processed at any time in order to assure that production goals and quotas are dependably met. As noted above, the NIR measurements and parameter predictions can start in the field, but may also be used as trucks, railcars, or barges of biomass feedstock enter the biorefinery, and continue as materials are brought into the process and during processing.

5.14 Sustainability Indicators

In some aspects the invention relates to methods for predicting the sustainability of a plant biomass production system by monitoring the levels of nitrogen, sulfur, phosphorus, potassium, magnesium, calcium, silicon, manganese, iron, zinc, chlorine, boron, and other micronutrients present in harvested plant biomass. (ref: Biochemistry and Molecular Biology of Plants, Buchanan, Gruissem, Jones, Ed., ASPB Press, 2000, pg 1205). Accordingly, NIR or Raman spectra of plant biomass samples are collected and translated by a NIR or Raman model to predict elemental composition. Analysis of biomass materials using methods such as atomic absorption (AA) and inductively coupled plasma (ICP) spectroscopy allow direct measurement of elemental composition that can then be correlated to NIR and Raman spectral features to create the NIR or Raman model for predicting these parameters. Prediction of elemental levels in harvested plant biomass may be used to monitor the amount and rate that certain elements and micronutrients are being removed from the soil and thus the amount and rate that these elements must be replaced. This knowledge may be used to make crop management decisions, such as determining crop rotations or co-cropping decisions. This knowledge may also be used to determine the quantity and composition of fertilizer applied to fields in subsequent years to assure a sustainable production system.

5.15 NOX emissions

In some aspects the invention relates to methods for predicting the NOX, SOX, and other greenhouse gas emissions associated with the processing of a plant biomass feedstock in a particular biorefinery or biopower generating station. The nitrogen, sulfur and other elemental composition of feedstock may be used to predict the emission produced upon processing. Accordingly, NIR or Raman spectra of plant biomass samples are collected and translated by a NIR or Raman model to predict elemental composition. Analysis of biomass materials using methods such as atomic absorption (AA) and inductively coupled plasma (ICP) spectroscopy allow direct measurement of elemental composition that can then be correlated to NIR and Raman spectral features to create the NIR or Raman model for predicting these parameters. Prediction of elemental levels in harvested plant biomass may be used to monitor the amount and rate that certain elements are being released to the atmosphere upon processing of the plant biomass under different conditions. This knowledge may be used to make feedstock supply management decisions. With the likelihood that certain emissions will be taxed, decisions such as the selection of plant biomass feedstock to be used at a biorefinery or biopower generating station or the price paid for a plant biomass feedstock may be influenced by the prediction of NOX, SOX, and other greenhouse gas emissions.

5.16 Protein and Other Co-Products

In some aspects the invention relates to methods for predicting the yield of protein and other co-products from a plant biomass feedstock used in a biorefinery. Relevant protein co-products derived from plant biomass feedstock include distillers grains, protein-enriched fractions of plant biomass for animal feed, or food applications, collagen, gelatin, nutritionally-relevant protein, and proteins useful for food processing, nutritional, and pharmaceutical applications. Other co-products of interest may include phytochemicals with nutritional, health, and pharmaceutical applications. Chemical co-products such as methacrylic acid, acrylic acid and their esters, as well as other chemicals and intermediates for chemical processing may be predicted. These include the chemicals defined as part of the definition of biofuels above. Co-product yield may be predicted for laboratory-, pilot-, or production-scale processes. Accordingly, NIR spectra of biomass samples are collected and translated by a NIR model. The result can be a direct prediction of one or more co-product yields or one or more intermediate values that may be correlated to co-product yield(s). A NIR model for co-product yield produced from laboratory-scale data may be used to predict performance in a production-scale facility. Predictions of co-product yield may be useful for managing biorefinery or biopower generation operations, selecting preferred feedstocks for processing, placing value on delivered feedstocks, anticipating and scheduling production, and managing a supply chain. Predictions of co-product yield may be useful in selecting plant species, varieties, populations, or individuals that will be most productive. Individuals selected in this manner may be introduced into breeding programs to produce new varieties, cultivars, inbreds, and hybrids with improved co-product yield.

6. Software

In some aspects the invention relates to software for developing NIR models. For example, the software can correlate spectroscopic data with compositional and biofuel conversion performance characteristics for lignocellulosic feedstocks. The software can establish validated mathematical correlations between NIR spectra and independently determined chemical constituents using multivariate statistical regression methods, such as those discussed above.

In some aspects the invention relates to software for using one or more NIR models to determine compositional characteristics and/or conversion efficiencies for a biomass sample. The software can be used to predict the composition of a feedstock, such as total carbohydrate, accessible carbohydrate, recalcitrant carbohydrate, glucan, xylan, arabinan, mannan, galactan, lignin, ferulate, acetate, nitrogen, protein, fixed carbon, ash, and elemental composition content. The software can also predict the syringyl:guiacyl:p-hydroxyphenol (S:G:H weight percents), carbon:hydrogen:oxygen (C:H:O) weight percents, and higher heating value (HHV). The software can also predict the conversion efficiency of a feedstock to free sugars, fermentable sugars, syngas, biofuel, ethanol, heat, or energy in a laboratory-, pilot-, or production-scale process. The software can also predict the yield of protein and other co-products from a plant biomass feedstock used in a biorefinery. The software can also predict the NOX, SOX, and other greenhouse gas emissions associated with the processing of a particular plant biomass feedstock in a particular biorefinery or biopower generating station. The software can also predict composition and/or conversion characteristics in a breeding population and/or recommend or select plants for breeding based on those predictions.

The software can also use NIR models to select a particular feedstock for a particular process. The software can also be used to design a particular process, design a biorefinery, and/or design a biopower generation facility based on the feedstock. Particular feedstocks can be grouped and analyzed based on the species, variety, cultivar, inbred, hybrid, line, genotype, and/or individual plants within a genetically diverse population of plants. The software can also use NIR spectra and NIR models to value a particular batch of feedstock based on the feedstock's composition or conversion characteristics. In giving a valuation of the batch of feedstock, the software can factor in the processing, transportation, taxation, and other costs for that batch of feedstock for a particular process.

The software can also be used for managing feedstock production and supply, and/or managing biorefinery operations and economics. For example, the software can manage the supply chain of the biomass feedstock for a biorefinery or biopower generation station. The software can also predict the sustainability of a plant biomass production system by tracking the levels of nitrogen, sulfur, phosphorus, potassium, magnesium, calcium, silicon, manganese, iron, zinc, chlorine, boron, and other micronutrients present in harvested plant biomass from a particular source.

7. Uses/Advantages

The described technology provides a number of advantages when compared to alternative solutions, although not all advantages may be present in a specific embodiment. In general, NIR models greatly reduce cost and speed up feedstock content analysis, and therefore are useful to many participants in the biofeedstock energy conversion industry. Consequently, NIR models can accelerate the development of economically viable processes for degrading cellulosic biomass to fermentable sugars. In some aspects, the methods and materials described herein can be used to achieve more efficient processing into free sugars, and subsequently ethanol. For example, the use of NIR models as described herein to quickly and accurately analyze feedstock samples provides new means with which to adjust biomass conversion conditions to achieve more economical and/or more efficient processing. Using this technology, a biorefinery can choose the most effective processes for the available feedstocks. For example, feedstock queuing, pretreatment conditions, and enzyme combinations and loading and other saccharification parameters, can be selected based in part on results of applying NIR models to data from feedstock samples. Particularly attractive are predictions of accessible carbohydrate material in biomass samples which permit biomass facilities to optimize the enzyme load for each lot of biomass feedstock, since enzyme cost is often a major cost component in cellulosic bioethanol production. By providing higher yields at an equivalent or even decreased cost of production, the methods and materials described herein improve profitability for farmers and processors as well as decrease costs to consumers, thus helping biofuels become more price competitive, and decreasing the need for subsidies for their adoption. Analysis of variables other than cost, such as biofuel, product, and/or co-product yield, emissions, system sustainability, biorefinery design, feedback to upstream or downstream activities, and can also be performed to influence biomass processing decisions and managing industry supply chains.

In other aspects, NIR models contribute to development and production of better feedstocks. The use of NIR models as described herein permits rapid identification of compositional and conversion efficiency variability and heritability within populations of biomass plants thereby guiding the breeding of plant varieties or populations with superior performance in yield of biomass and biofuel. The models are also helpful in selecting potential parents from populations and evaluating their progeny, thus advancing bioenergy feedstock breeding programs. Valuable bioenergy conversion attributes can be associated to specific molecular markers of a feedstock species of interest, further helping breeding toward high energy yield targets. For example, feedstock varieties may be developed with optimized characteristics for specific energy conversion options. Using the described technology, plant breeders can optimize germplasm for economically valuable characteristics, such as increased yield of biofuel produced per acre of farmland, increased yield for a specific conversion process, co-product yield and quality, sustainability of feedstock farming, and lowered greenhouse emissions from feedstock energy conversion processes. The described technology can help determine suitable or optimum harvesting time, transportation, and/or storage conditions.

Furthermore, NIR models report data in a form that can be integrated directly into engineering, economic, and life-cycle models for a clearer evaluation of enhanced value and appropriate price points across a wide variety of biomass conversion processes. Feedstock valuation may be more precise, as it may take into account more accurate estimates of yield and processing costs. In sum, the disclosed technology can be valuable to many participants in the biofuel production industry, such as NIR instrument manufacturers, researchers in fields such as germplasm improvement and enzyme production, feedstock farmers, wholesalers and biorefiners, as well as associated transportation and logistic operations.

The invention will be further described in the following examples, which do not limit the scope of the invention described in the claims.

EXAMPLES

Example 1

Sample Preparation and NIR Spectroscopy

Samples of biomass (typically at least 20 g dry weight) from switchgrass plants were collected and prepared for compositional analysis as described in "Preparation of Samples for Compositional Analysis," September 2005, by the US Dept. of Energy National Renewable Energy Laboratory, which is substantially similar to ASTM method E1757-01. Briefly, samples were dried to a moisture content of 10% or less, either at room temperature or in a forced air oven set at or below 45° C. After drying, samples were milled in a standard laboratory knife mill to pass a 2 mm screen.

Near infrared spectral data were acquired from switchgrass samples using a Bruker Optics MPA™ FT-NIR spectrometer (Bruker Optics, Ettlingen, Germany), running Opus 5.5 software essentially according to the manufacturer's protocols.

An integrating sphere with a rotating sample cup assembly cup was used to obtain spectra. A standard lead-sulfide detector array was used to monitor NIR light from 12,800-5,800 $cm^{-1}$. A Blackman-Harris 3-term apodization function was selected with a zero filling factor of 2. The Bruker instrument has a maximum resolution of 2 $cm^{-1}$. To minimize the effect of water in the biomass spectra, each sample was air dried to less than 10% moisture prior to NIR analysis. Spectral information was collected from 12,500 $cm^{-1}$ to 3600 $cm^{-1}$ with a resolution of 8 $cm^{-1}$. For each spectroscopic sample, a total of 64 spectra were collected and averaged to compensate for sample heterogeneity. Each calibration sample was subsampled three times and the sub-sample spectra were averaged. Final averaged spectra were used in the method calibration. These spectroscopic techniques enabled a high quality, reproducible NIR reflectance spectrum to be obtained for each of the calibration samples. The spectrum was representative of the wet chemistry data as indicated by the validation experiments discussed below. Instrument reproducibility tests indicated that the reproducibility limits of the NIR spectrometer contributed less than 0.2% to the absolute prediction errors in NIR/PLS models.

Example 2

Composition Ranges of Calibration Set

Approximately 1,000 samples of switchgrass biomass were collected from diverse geographic locales in the United States. Using principal component analysis (PCA), a calibration set of 55 field-grown and greenhouse-grown samples was selected to represent the larger sample set. FIG. 1 compares the PCA scores of the calibration set relative to the scores of the larger switchgrass population, demonstrating the ability of the smaller calibration set to represent the larger population. The glucan, xylan, arabinan, lignin and ash components were determined by ASTM methods E1758-01 *Determination of Biomass Sugars by High Performance Liquid Chromatography*, E1721-01 *Determination of Acid Insoluble Residue (Lignin) in Biomass* and E1755-01 *Determination of Ash Content in Biomass*. Protein was determined using the DOE/EERE Method *Determination of Protein Content in Biomass*. Extractives were measured following the Automated Solvent Extraction (ASE) methods in the DOE/EERE method *Determination of Extractives in Biomass*. Fermentable sugars were calculated as the sum of glucan, xylan and arabinan. The composition ranges of the calibration set are shown in Table 1.

TABLE 1

| Composition Ranges of Calibration Set | |
|---|---|
| Component | Range (% dry weight) |
| Glucan | 17.9-42.5 |
| Xylan | 15.7-26.7 |
| Fermentable Sugars | 45.6-64.5 |
| Arabinan | 3.1-9.0 |

TABLE 1-continued

| Composition Ranges of Calibration Set | |
|---|---|
| Component | Range (% dry weight) |
| Sucrose | 0.4-12.7 |
| Lignin | 17.2-23.5 |
| Protein | 0.9-1.8 |
| Ash | 0.9-7.9 |
| Extractives | 5.0-28.3 |

A summative mass closure analysis of all 55 samples was obtained using a portfolio of standard analytical methods listed above. The average mass closure for the calibration samples was 100.34±3.5% (95% Confidence Interval).

Example 3

Composition Model Development and Validation

Multivariate analysis methods were used to reveal correlations between the chemical composition of the 55 switchgrass biomass samples of Example 2 and NIR spectral data from the same samples. A full cross validation procedure was used to develop and validate a series of projection to latent structures (PLS-1) multivariate analysis equations that could be used to determine the chemical composition of unknown samples. During the cross validation process, a single sample was removed from the calibration set, all other samples were used to make an equation and the missing sample was predicted using that equation. The final method equations were an average of all of the cross validation equations. The resulting PLS-1 equations were designated the SWG_2 model. A representative equation is shown in FIG. 2.

Figure 3:
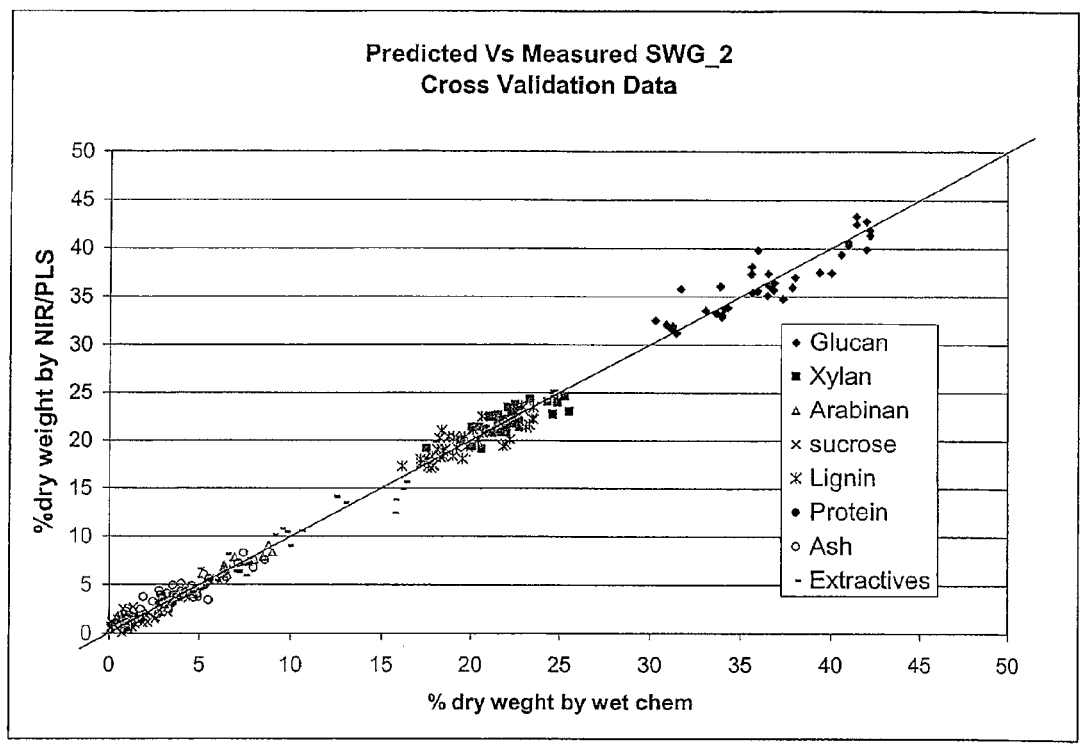
FIG. 3 is a comparison of the composition of calibration samples determined by wet chemical methods and cross validation values for the SWG_2 model.

FIG. 3 shows the percent dry weight of various biomass components predicted by the SWG_2 model for each sample versus the percent dry weight of those components as determined by wet chemistry. The graph indicates that the SWG_2 model predicts the compositional analysis for a wide range of samples with an accuracy that matches the wet chemical methods.

Figure 4:
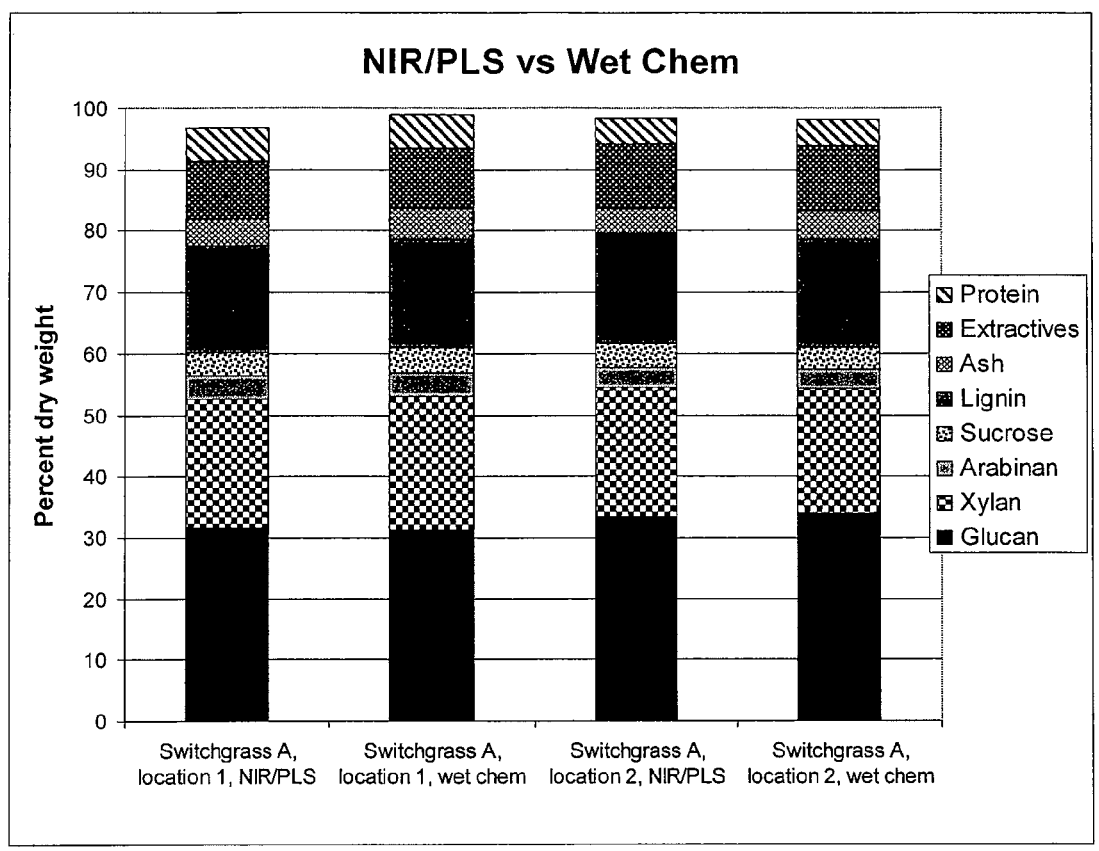
FIG. 4 is a comparison of the composition of independent validation samples determined by wet chemical methods and the SWG_2 model.

The composition of two switchgrass biomass samples was determined by the methods of Example 2. NIR spectral data were collected from each sample and the composition predicted by the SWG_2 model. FIG. 4 shows the results of the analyses. The results indicate that the composition predicted by the SWG_2 model is indistinguishable from the composition determined by wet chemistry within method errors. Thus, the SWG_2 NIR model can be used to determine the chemical composition of switchgrass test samples directly from their NIR spectra.

The SWG_2 model was used to identify additional biomass samples that had amounts of one or more components that fell outside the range for that component in the calibration set and/or had a value not represented in the original calibration set. Expanded NIR models were then developed using the original SWG_2 calibration samples as well additional samples, and validated. Representative results for certain biomass components of additional NIR models are shown in Table 2.

TABLE 2

| Model | Number of Calibration Samples | No. of PCs | $R^2$ | RMSECV | Range (% dry weight) |
|---|---|---|---|---|---|
| Lignin | | | | | |
| SWG_2 | 44 | 4 | 0.72 | 1.1 | 16.1-23.5 |
| SWG_3 | 81 | 6 | 0.93 | 0.8 | 11.6-22.6 |
| SWG_4 | 85 | 6 | 0.93 | 0.8 | 11.6-22.6 |
| Glucan | | | | | |
| SWG_2 | 37 | 4 | 0.79 | 1.7 | 30.3-40.2 |
| SWG_3 | 55 | 6 | 0.81 | 2.1 | 23.3-40.8 |
| SWG_4 | 83 | 6 | 0.82 | 2.3 | 20.8-42.8 |

Example 4

Conversion Model Development and Validation

Twenty-eight of the samples used in the development of the SWG_2 composition model (Example 3) were used for NIR conversion model development and validation. NIR spectra were collected from each sample prior to further processing. Each sample was then subjected to an acid pretreatment and enzymatic saccharification procedure as follows. About 0.025 g dry weight of each sample and 55.6 ul of 72% (w/w) sulfuric acid in 5 ml total volume (1.3 wt % acid in the liquid phase of the vessel) were added to a microwave tube. The tube was heated in a Biotage Initiator 60 microwave system at 160° C. for 5 minutes with stirring. After cooling with forced convective cooling, each tube was centrifuged at 4,000 rpm for 5 minutes. The supernatant (pretreatment liquor, PL) was removed, the pH recorded, and the supernatant was frozen. The centrifuged solids of each sample tube were then washed three to four times with water until the pH of the wash was between 5-6.

After removing excess water from the tubes, the washed, wet solids from each sample were transferred to a new tube containing 50 mM citrate buffer (pH 4.8), 0.04 mg/ml tetracycline, 0.03 mg/ml cycloheximide, and 20 mg total protein of Spezyme® CP and 20 mg total protein Novozyme 188 mixture per gm dry biomass. The total volume was 1 ml. Each tube was incubated at 50° C. with shaking After 1 hr, 150 ul was removed from each tube using a wide bore 200 ul tip, transferred to a 1.5 ml centrifuge vial, and boiled for 5 minutes. The wide bore tip allowed complete collection of the solids in each tube. Each vial was then centrifuged at 14,000 rpm for 2 min. A 100 ul portion of each supernatant was transferred to a 12×75-mm tube, 900 ul of water was added, and the samples were analyzed for glucose in a YSI 2700D Dual-Channel Biochemistry Analyzer (YSI Life Sciences, Yellow Springs, Ohio). After 24 hours, all of the remaining sample was removed, boiled, and centrifuged as described above. A 100 ul aliquot was removed, diluted 1:10, and analyzed for glucose in the YSI analyzer.

The amount of total glucose released into the acid pretreatment liquor was determined as follows. For monomeric glucose, calcium carbonate was added to a portion of each PL sample while vortexing, until the pH reached 5-6. The vials were then centrifuged at 4000 rpm for 5 min, a 1 mL aliquot of each sample was transferred to a 12×75-mm tube, and each aliquot was analyzed for glucose in the YSI Analyzer. For the determination of the amount of oligomeric glucose, the previously recorded pHs were used to determine the amount of 72% sulfuric acid that must be added in order to achieve 4% total acid (NREL Lab Practice "Determination of Sugars, Byproducts, and Degradation Products in Liquid Fraction Process Samples"). The 72% sulfuric acid was added to 2 mL of PL in a serum vial, then crimp sealed and autoclaved at 121° C. for 60 min using the liquid cycle. After allowing samples to cool to room temperature, calcium carbonate was added while vortexing until pH was raised to 5-6. Calcium carbonate was then separated from the liquid by centrifuging and glucose was measured by YSI. Oligomeric glucose was then calculated by subtracting the monomeric glucose concentration measured in the original PL sample from the monomeric glucose concentration measured in the acid-hydrolyzed PL sample.

Thirty-seven diverse switchgrass samples were analyzed using a base pretreatment procedure. For alkaline pretreatment, 5 mL of a dilute solution of ammonium hydroxide was added to approximately 0.025 g dry weight of biomass in a 2-5 mL Biotage microwave tube such that the mass ratio of ammonia to biomass was 2:25. The tube was heated in a Biotage Initiator 60 microwave to 205° C. and held at constant temperature for 30 minutes while stirring at 900 rpm. After forced convective cooling to 50° C., the tube was centrifuged at 4000 rpm for 5 min and the pretreatment liquor (PL) was collected. Solids were washed by adding water, centrifuging, and discarding wash water 2-3 times until pH 5-6 was reached as measured by a pH 2-9 indicator strip.

The washed, wet solids from each acid and alkaline pretreatment sample were saccharified as described above, using 20 mg protein/gm dry biomass of each of filtered Spezyme® CP and Novozyme 188. The amount of glucose released was determined as described for the acid pretreatment system. For alkaline pretreatment saccharification samples, an additional assessment of oligomeric sugars was performed. 200 ul of saccharification liquid was diluted 1:10, and 69.7 ul of 72% sulfuric acid was added to each sample. The vials were then autoclaved and oligomeric sugar was determined in the same manner as the acidic pretreated PL samples.

The amount of total glucose released into the alkaline pretreatment liquor was determined as follows. For monomeric glucose, a portion of the PL was directly assessed for glucose content in the YSI Analyzer. The amount of oligomeric glucose was determined by adding 69.7 ul of 72% sulfuric acid to 2 ml of PL in a serum vial. The vials were then autoclaved and assessed by the same methods as described above for the acid pretreatment PL samples.

A full sugar analysis was performed via HPLC on each PL sample and the 24 hr saccharification sample in order to quantify all other available sugars, e.g., xylose and arabinose.

The SWG_2 composition model was used to calculate the theoretical yield of glucose that could maximally be released by a given biomass sample. The glucose conversion efficiency was calculated as the total amount of glucose released by acid pretreatment/enzymatic saccharification, divided by the theoretical maximum amount of glucose in the biomass sample that could have been released, and converted to a percentage by multiplying by 100.

Figure 5:
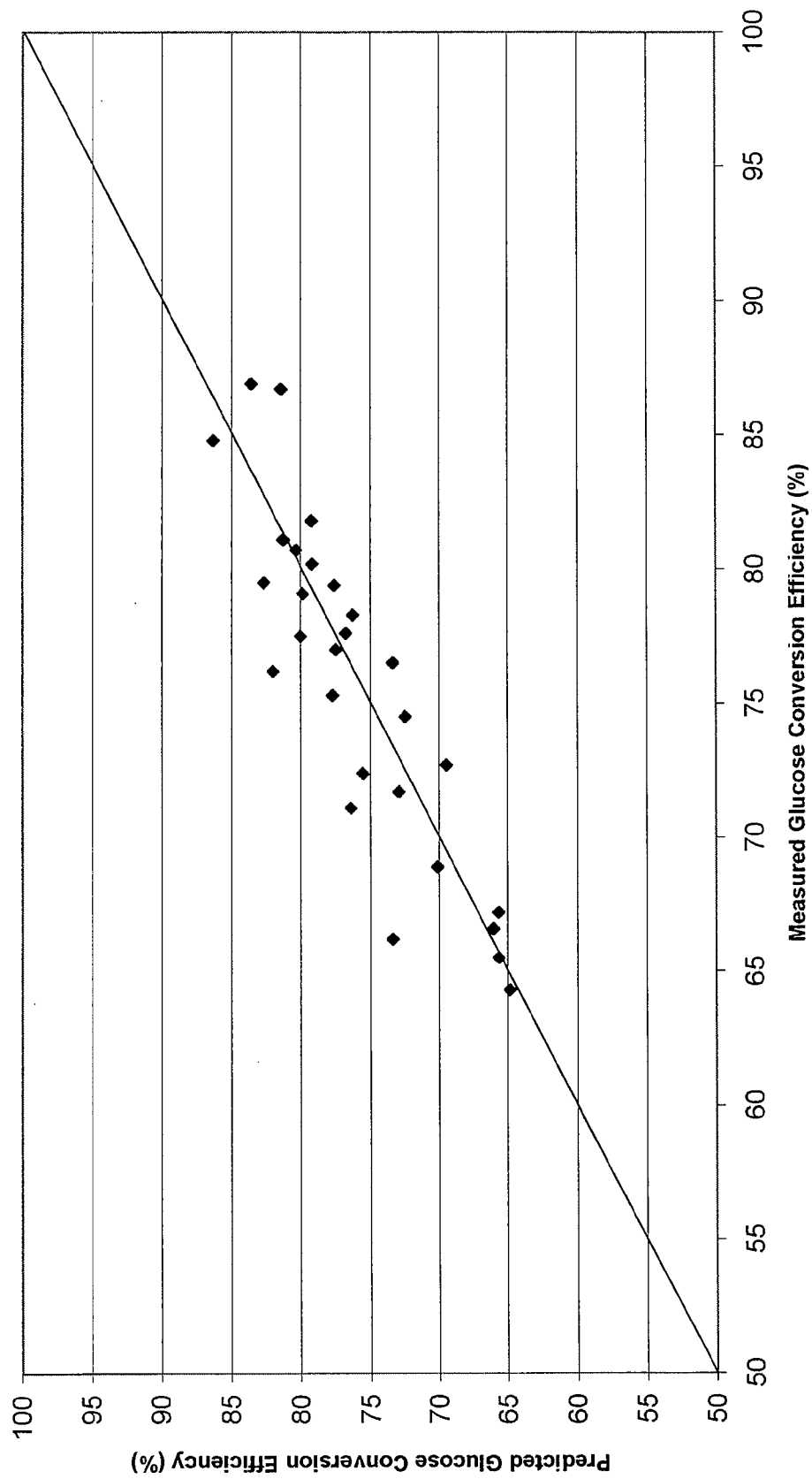
FIG. 5 is a comparison of the glucose conversion efficiency determined by wet chemical methods versus the glucose conversion efficiency predicted by a NIR conversion model, for samples subjected to acid pretreatment and enzymatic saccharification.

Multivariate analysis methods were used to reveal correlations between the percent of theoretical glucose yield under acidic conversion conditions and NIR spectral data from the same samples. FIG. 5 compares the measured percent glucose conversion efficiency versus the glucose conversion efficiency predicted from the NIR conversion model. The results showed that the $R^2$ value for percent glucose conversion efficiency predicted by the conversion model versus the measured conversion efficiency was 0.78, with a Root Mean Square Error of Cross Validation (RMSECV) of 2.89, indicating a good correlation.

Multivariate analysis methods were used to reveal correlations between the total glucose released per gram dry biomass under the alkaline pretreatment/saccharification conditions and NIR spectral data from the same samples. The cross validation results indicated that the $R^2$ value for measured versus predicted total glucose released per gram dry biomass was 0.85 with a RMSECV of 12.4. The good correlation between the measured values and those predicted by the model indicates that NIR models for other types of biomass can be developed to predict total glucose released per gram dry biomass under alkaline conversion conditions.

The percent of theoretical yield, weight percent recalcitrant glucan, and total glucose released per gram dry biomass are interconvertible values, and a NIR model that can determine one of these values from NIR spectra can be used to determine the other values.

Example 5

Variability in Switchgrass Populations

Figure 6:
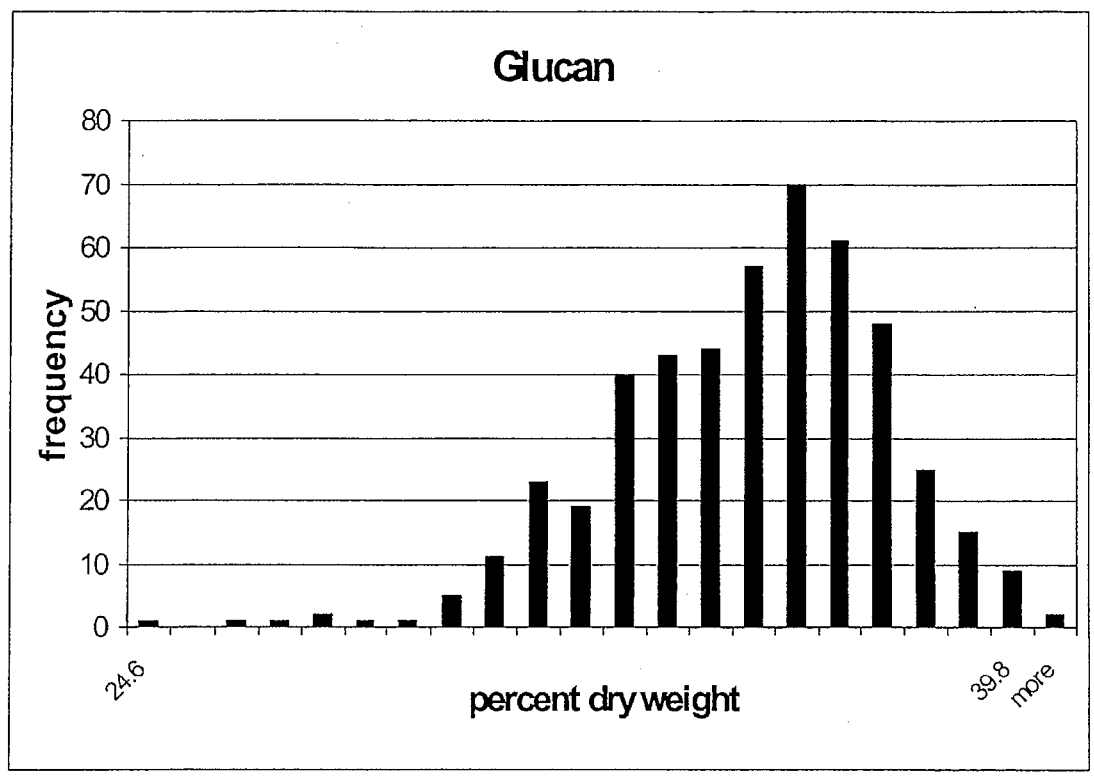
FIG. 6 is a plot of the distribution of glucan amounts in a switchgrass population.
Figure 7:
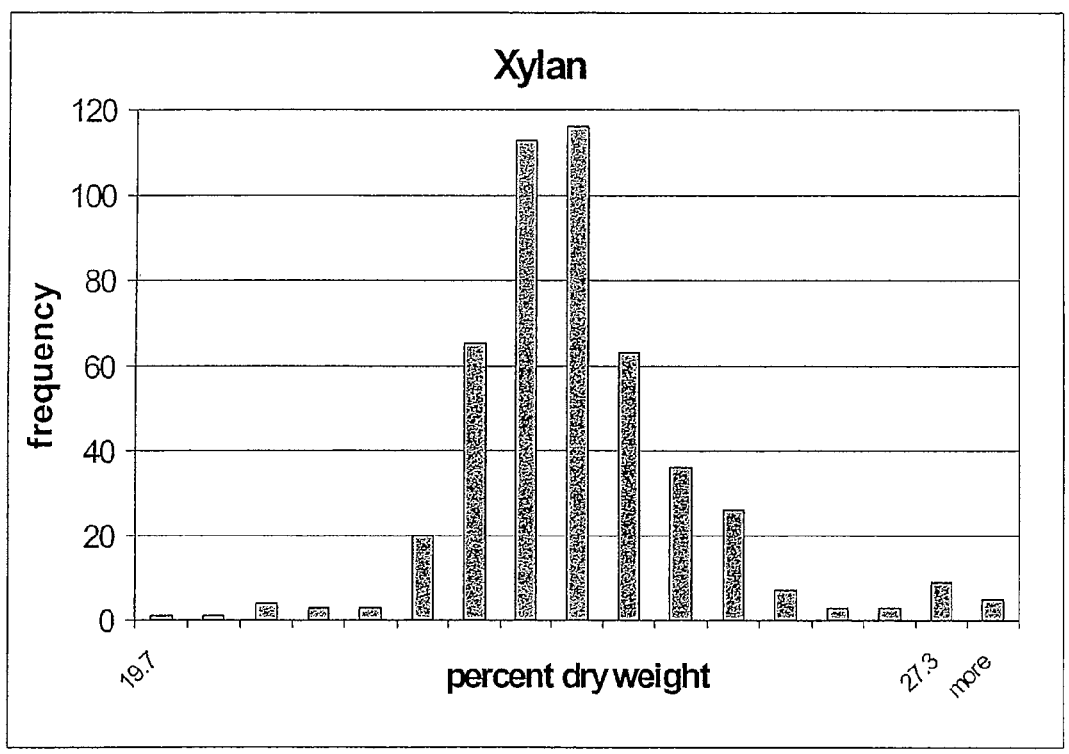
FIG. 7 is a plot of the distribution of xylan amounts in a switchgrass population.
Figure 8:
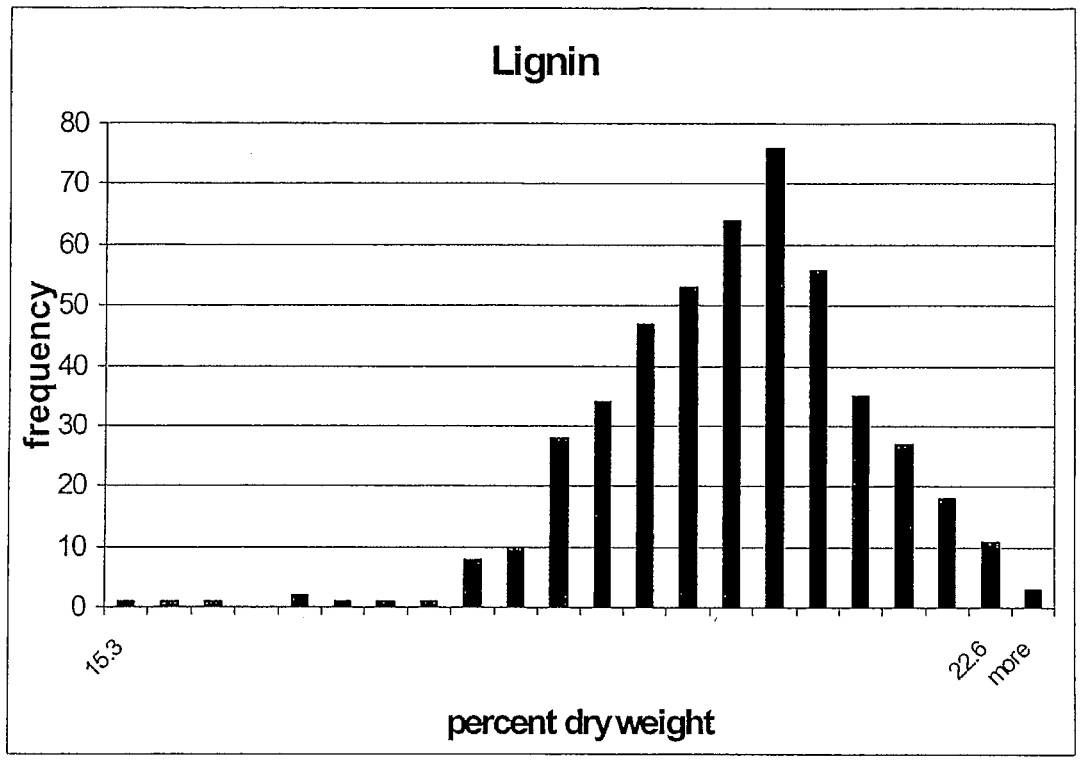
FIG. 8 is a plot of the distribution of lignin amounts in a switchgrass population.

About 30 to 200 gm of biomass was collected as described in Example 1 from each of 790 switchgrass plants grown at one location in the south central plains region of the United States. The biomass was obtained from plants that had been established for about 10 to 15 years. The plants were from 150 different switchgrass accessions. An FT-NIR spectrum was acquired as described in Example 1 and the composition of each sample was predicted using the SWG_2 model. FIGS. 6-8 are histograms showing the frequency distribution of the glucan, xylan and lignin amounts, respectively, in biomass from the 790 plants. Table 3 shows the range and mean amounts of certain biomass components in the set of 790 plants.

TABLE 3

Composition of Switchgrass Plants

| Biomass Component | Mean | Range |
| --- | --- | --- |
| Glucan | 34.9 | 27.6-41.1 |
| Xylan | 23.0 | 17.1-27.8 |
| Lignin | 20.1 | 15.3-22.9 |
| Ash | 4.5 | 1.0-12.1 |

Composition was determined from the NIR data using the SWG_2 model. The amounts of biomass components are shown in Table 4 below.

TABLE 4

Biomass Composition at Different Developmental Stages

| Biomass | SWG E | | | SWG F | | |
| --- | --- | --- | --- | --- | --- | --- |
| Component | young tiller | booting tiller | flowering tiller | young tiller | booting tiller | flowering tiller |
| Glucan | 31.2 | 33.6 | 35.1 | 29.3 | 32.1 | 36.6 |
| Xylan | 20.2 | 20.2 | 21.0 | 19.8 | 19.9 | 20.6 |
| Arabinan | 4.1 | 4.6 | 6.2 | 3.8 | 4.2 | 4.7 |
| Sucrose | 0.0 | 0.2 | 0.5 | 0.5 | 0.3 | 2.3 |
| Lignin | 17.0 | 18.3 | 19.6 | 16.1 | 17.5 | 20.0 |
| Protein | 7.0 | 5.8 | 5.2 | 8.9 | 7.4 | 5.5 |
| Ash | 3.0 | 2.6 | 1.9 | 3.6 | 2.6 | 2.0 |
| Extractives | 13.9 | 13.2 | 11.1 | 13.4 | 12.9 | 10.1 |

The acid pretreatment/enzymatic saccharification procedure described in Example 4 was carried out on each of the biomass samples. Table 5 shows the percent glucose conversion at the 1 and 24 hour time points after acid pretreatment/enzymatic saccharification of the biomass samples.

The results indicate that the amount of glucan and other components in switchgrass varies at different developmental stages. The results also indicate that the glucose conversion efficiency for these samples is more than 87% at the young tiller stage after a 24 hour saccharification. In contrast, the glucose conversion efficiency for these samples is 81% or less at the flowering tiller stage. Such data can be used to develop a NIR model to predict composition at various developmental stages of a given biomass type and accessible carbohydrate at each such stage with a given pretreatment/saccharification procedure. One use of such a model is to manage a biomass crop so that harvest occurs at the plant developmental stage that results in maximum biofuel production for the crop with a given pretreatment/saccharification procedure.

TABLE 5

| | SWG E | | | SWG F | | |
| --- | --- | --- | --- | --- | --- | --- |
| Sample | young tiller | booting tiller | flowering tiller | young tiller | booting tiller | flowering tiller |
| % Glucose Conversion Efficiency (1 hr incubation) | 59.5 | 55.0 | 44.2 | 66.0 | 56.8 | 42.2 |
| % Glucose Conversion Efficiency (24 hr incubation) | 87.8 | 85.5 | 79.3 | 89.3 | 88.4 | 81.0 |

Example 6

Switchgrass Composition at Different Developmental Stages

Biomass samples from two switchgrass plants were collected at different developmental stages. The samples were prepared and NIR data acquired as described in Example 1.

Example 7

Glucose Conversion Efficiency of Switchrass Samples

The biomass composition for two of the 790 switchgrass plants from Example 5 as predicted by the SWG_2 model is shown in Table 6.

TABLE 6

| Plant | Glucan | Xylan | Arabinan | Sucrose | Fermentable Sugars | Lignin | Protein | Ash | Extractives |
|---|---|---|---|---|---|---|---|---|---|
| A | 39.54 | 24.10 | 7.79 | 1.04 | 63.64 | 22.36 | 1.14 | 2.28 | 5.62 |
| B | 35.24 | 23.34 | 7.68 | 2.5 | 58.58 | 20.17 | 1.22 | 4.82 | 6.7 |

Figure 11:
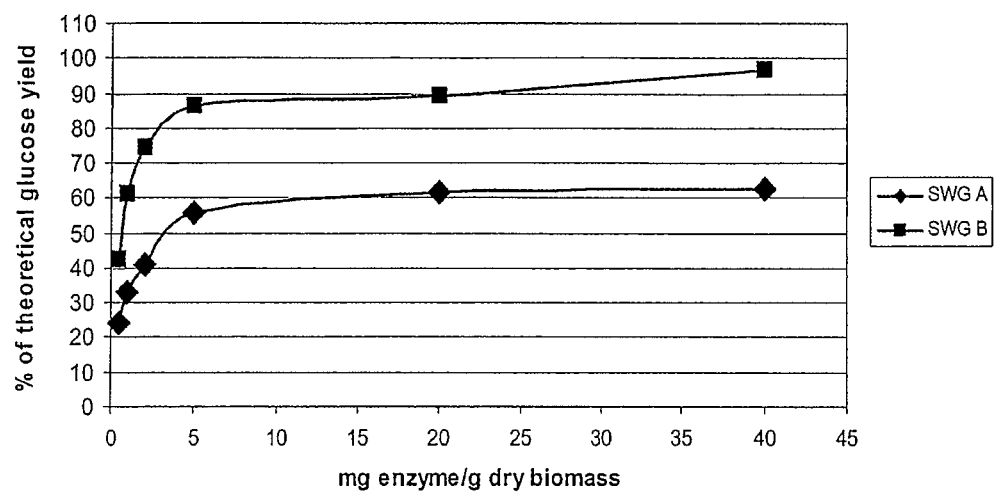
FIG. 11 is a conversion analysis of two switchgrass samples after acidic pretreatment/enzymatic saccharification.

The procedure for the determination of conversion efficiency under acid pretreatment conditions described in Example 4 was repeated for biomass samples from plants A and B, measuring the glucose conversion efficiency at 24 and 72 hours of incubation with varying amounts of a cellulase mixture supplemented with Novozyme 188. FIG. 11 shows the conversion efficiency at the 72 hour time point after acid pretreatment/enzymatic saccharification of biomass from switchgrass plants A and B, versus the amount of enzyme. The results indicate that more than 90% of the maximum theoretical glucose yield from plant B is achieved when about 5 to 20 mg of cellulase is added per gm of biomass. In contrast, about 55 to 65% of the maximum theoretical glucose yield from plant A is achieved when about 5 to 20 mg of cellulase is added per gm of biomass. These results indicate that biomass from plant B is more easily digested with a given amount of enzyme compared to biomass from plant A, and that plant A cannot achieve 100% conversion to glucose under these conditions even at high enzyme loadings.

Figure 12:
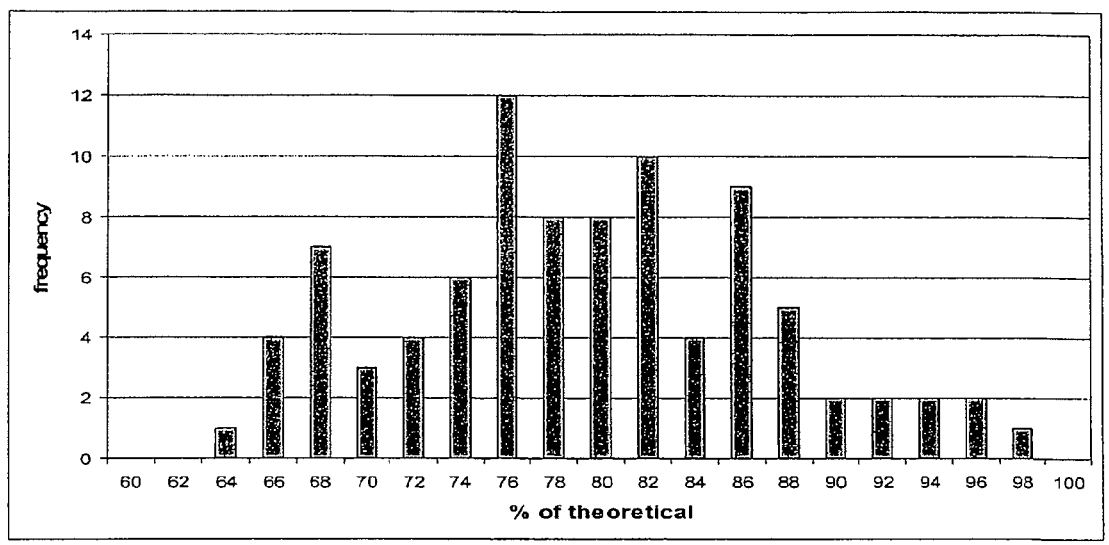
FIG. 12 is a histogram of the conversion efficiencies of 90 different switchgrass samples assessed using acidic pretreatment/enzymatic saccharification.

Biomass samples from 90 other switchgrass plants were subjected to the same acid pretreatment and enzymatic saccharification procedure as described above for plants A and B, using 20 mg protein/gm dry biomass of each of filtered Spezyme® CP and Novozyme 188. FIG. 12 shows the frequency distribution for glucose conversion efficiency for all 90 biomass samples. The results indicate that glucose conversion efficiency varies considerably among switchgrass plants.

Example 8

Predicted Weight Percentage Glucan vs. Glucose Released

Multiple biomass samples were collected from a variety of different switchgrass plants from diverse geographic locales in the United States, and prepared as described in Example 1. NIR data from each biomass sample was then used to predict the weight percentage of glucan in each sample using the SWG_2 model. The biomass samples were then subjected to the acid pretreatment procedure or alkaline pretreatment procedure described in Example 4.

Figure 13:
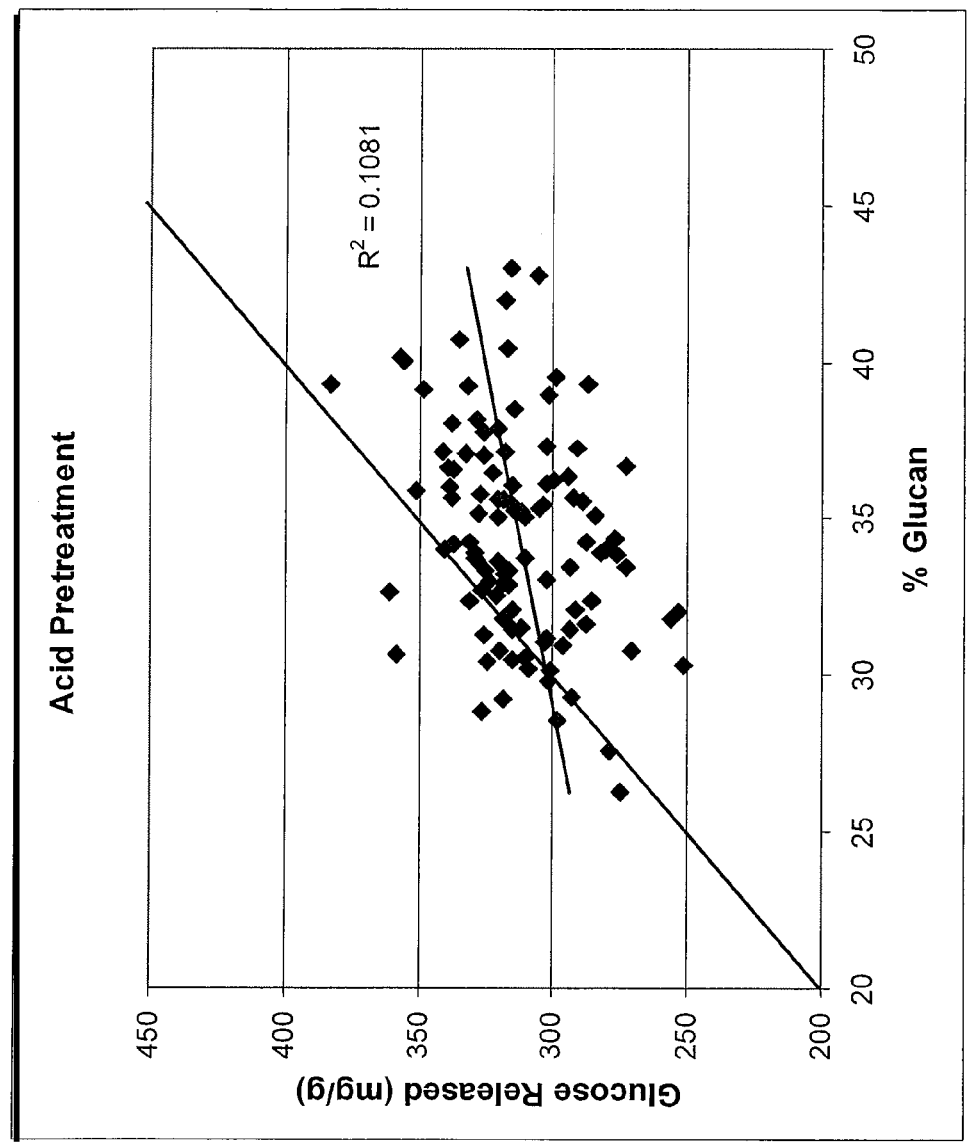
FIG. 13 is a plot of the amount of glucose released from different switchgrass samples after an acid pretreatment/enzymatic saccharification.
Figure 14:
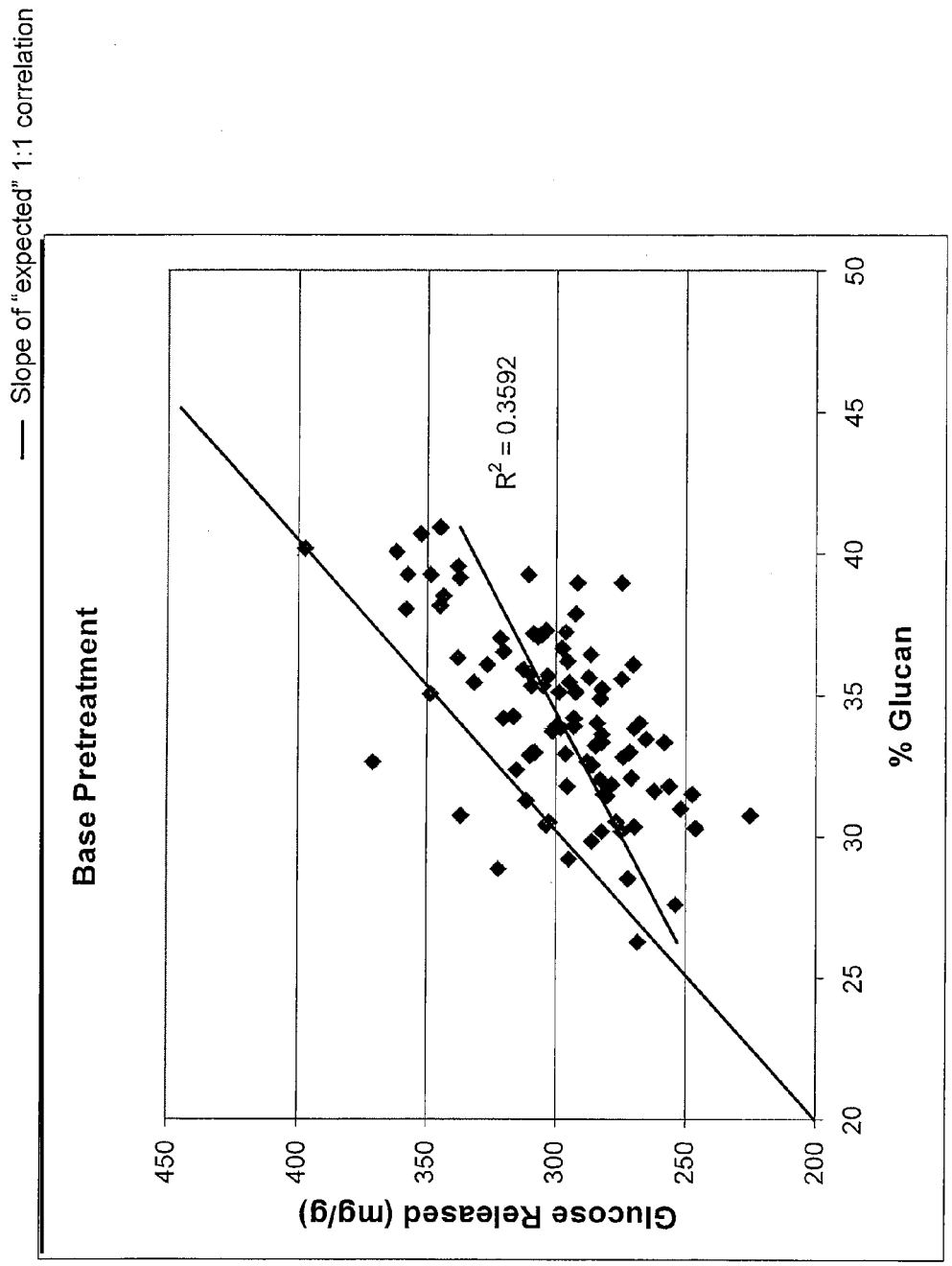
FIG. 14 is a plot of the amount of glucose released from different switchgrass samples after an alkaline pretreatment/enzymatic saccharification.

The amount of glucose released, in terms of mg/g, was then plotted against the SWG_2-predicted weight percentage of glucan for each acid pretreatment sample and for each base pretreatment sample. The results are shown in FIGS. 13 and 14. The results indicate there is no significant correlation between the predicted amount of glucan versus the amount of glucose released for acid pretreatment, and a slight positive correlation for base pretreatment.

The results of these experiments along with the results described in Example 4 indicate that measuring or predicting the amount of glucan present in a biomass sample is insufficient to identify biomass material that yields a greater amount of glucose. In addition, the results indicate that a conversion NIR model such as that described in Example 4 predicts glucose conversion efficiency with sufficient accuracy to identify a biomass material that yields a relatively higher amount of glucose released even though the material possesses a relatively lower glucan content.

Example 9

Ethanol Yield from Switchgrass Biomass

Biomass was collected from three switchgrass plants and NIR data acquired as described in Example 1. The amount of glucan was predicted using the SWG_2 model for each plant, and the yield of biomass from each plant was determined. The results, which are shown in Table 7, indicate that the amount of glucan in each sample was similar, whereas the biomass yield varied among the samples. Based on these data, the maximum theoretical yield of ethanol from glucan per ton of biomass and the maximum theoretical yield of ethanol per acre were calculated for each sample, and are shown in Table 7.

TABLE 7

% Glucan and Biomass Yield for Switchgrass Samples

| Switchgrass Variety | % Glucan* | Theoretical Ethanol Yield (Gal/Ton)** | Biomass Yield (tons/acre) | Theoretical Ethanol Yield (Gal/Acre)*** |
|---|---|---|---|---|
| Parent | 39.11 | 67.6 | 7.7 | 518 |
| Variety C | 40.18 | 69.4 | 7.9 | 548 |
| Variety D | 39.27 | 67.9 | 6.4 | 435 |

*Predicted from SWG_2 model.
**Gal ethanol/ton of biomass (based on amount of glucan and assuming 100% conversion of glucan to glucose).
***Gal ethanol/acre of Switchgrass (based on amount of glucan, biomass yield, and assuming 100% conversion of glucan to glucose).

The glucose conversion efficiency of biomass from each plant was determined using the acid pretreatment/enzymatic saccharification procedure described in Example 4, and the results are shown in Table 8. The results indicate that biomass from Variety D had a higher glucose conversion efficiency than biomass from the other two plants and thus has more accessible carbohydrate as a % of total carbohydrate relative to Variety C.

TABLE 8

Glucose Conversion Efficiency of Switchgrass Samples

| Switchgrass Variety | % Glucan | Glucose Conversion Efficiency (%) | Ethanol Yield (Gal/Ton)* | Theoretical Ethanol Yield (Gal/Acre)** |
|---|---|---|---|---|
| Parent | 39.11 | 75.7 | 51.2 | 393 |
| Variety C | 40.18 | 74.8 | 52.0 | 410 |
| Variety D | 39.27 | 83.2 | 56.5 | 362 |

*Based on amount of glucan and glucose conversion efficiency.
**Based on amount of glucan, glucose conversion efficiency and biomass yield.

Based on the glucose conversion efficiency and biomass yield, the ethanol yield per ton and ethanol yield per acre that would be produced by each plant were calculated. The results are shown in Table 5, and indicate that higher glucose conversion efficiency can compensate for reduced biomass yields. The results also indicate that plants can be identified that have both higher biomass yield and higher glucose conversion efficiency.

Example 10

Predicting Enzyme Load Conditions for Biomass Processing

Biomass was collected from a plurality of field-grown switchgrass plants of a single variety. A biomass sample was prepared as described in Example 1 and composition determined using wet chemistry techniques described in Example 1. The glucan component constituted 36.8% of the dry weight of the biomass. The theoretical maximum amount of glucose in the biomass sample that could have been released was calculated to be 408 mg glucose per gm dry biomass.

The acid pretreatment/enzymatic saccharification procedure described in Example 4 was carried out on the biomass sample, and the average amount of glucose released after a 24 hour incubation with an excess of Spezyme® and Novozyme 188 (20 mg Spezyme® supplemented with 20 mg Novozyme 188 per gm biomass) was determined to be 254 mg of glucose per gm of biomass. Based on the theoretical maximum glucose yield with an excess of enzyme, the amount of enzyme needed to achieve maximum glucose conversion efficiency was calculated to be 12.5 mg Spezyme and 12.5 mg Novozyme 188 per gm of accessible glucan.

The acid pretreatment/enzymatic saccharification procedure was repeated with the biomass sample, except that 12.5 mg Spezyme® and 12.5 mg Novozyme 188 were used per gm accessible glucan. The amount of glucose solubilized after incubation for 1 and 24 hours was determined and is shown in Table 9. The results indicate that percent glucose conversion at 12.5 mg/gm accessible glucan is equivalent to or better than the percent glucose conversion at 20 mg/gm biomass.

TABLE 9

| Enzyme Amount (mg/gm) | % Glucose Conversion (1 hr incubation) | % Glucose Conversion (24 hr incubation) |
|---|---|---|
| 20 | 25 | 65 |
| 12.5 | 26 | 70 |

Assuming an enzyme cost of $0.32 per gallon of ethanol, these results indicate that a savings of $0.13 per gallon of ethanol would result. Under this assumption, a biorefinery that produces 100,000,000 gallon of ethanol per year could reduce annual enzyme costs about $12,800,000 by loading enzymes on the basis of accessible carbohydrate.

Example 11

Predicting Optimum Enzyme Mixtures for Biomass Processing

Biomass was collected from a plurality of field-grown switchgrass plants of a single variety. A biomass sample was prepared as described in Example 1 and composition determined using wet chemistry techniques described in Example 1. The glucan component constituted 36.8% of the dry weight of the biomass. The theoretical maximum amount of glucose in the biomass sample that could have been released was calculated to be 408 mg glucose per gm dry biomass.

The acid pretreatment/enzymatic saccharification procedure described in Example 4 was carried out on the biomass sample, except that different enzyme cocktails were used. Enzyme cocktail I contained a proprietary cellulase complex (designated S13) and Novo 188. The cellulase complex catalyzes the breakdown of cellulosic material into glucose, cellobiose, and higher glucose polymers. Enzyme cocktail II contained a proprietary enzyme complex (designated S12) and Novo 188. The enzyme complex contained various carbohydrases, including arabinase, cellulase, beta-glucanase, hemicellulase and xylanase. Enzyme cocktail III contained a proprietary xylanase (designated S14), Spezyme® and Novo 188. The xylanase was a high temperature endo-xylanase that hydrolyzes xylans and arabino-xylans into oligosaccharides and some mono-, di- and trisaccharides, and is active with both soluble and insoluble arabino-xylans. An enzyme cocktail containing Spezyme® and Novo 188 was used as a control.

The results are shown in Table 10. The results indicate that the amount of glucose solubilized varies depending upon the enzyme cocktail used for saccharification. Such data can be used to develop a NIR model of accessible carbohydrate for each combination of enzyme cocktail, biomass type and pretreatment/saccharification procedure.

TABLE 10

| | % Glucose Conversion Efficiency (24 hr incubation) | | | |
|---|---|---|---|---|
| Enzyme amounts* | Control Enzyme Mixture | Enzyme Cocktail I | Enzyme Cocktail II | Enzyme Cocktail III |
| 0 | 0 | 0 | 0 | ND |
| 2.5 | 45 | 42 | 5 | ND |
| 5 | 53 | 52 | 7 | ND |
| 10 | 56 | 55 | 12 | ND |
| 20 | 58 | 58 | 14 | 56 |
| 40 | 58 | 58 | 13 | ND |

*= mg of each enzyme or enzyme complex per gm biomass.
ND = Not determined

Example 12

NIR Models for Lignin Content

Biomass samples were prepared as described in Example 1 from switchgrass, *Arabidopsis thaliana*, and sorghum plants. Twenty six, 71 and 24 samples were prepared from switchgrass, *Arabidopsis*, and sorghum, respectively. NIR spectra were collected for each of the switchgrass, *Arabidopsis*, and sorghum biomass samples prior to further processing.

S, G, and H amounts were determined by the following wet chemistry technique. Pyrolysis GC-MS was performed on a Py-2020 is pyrolyzer (Frontier Labs, Japan) coupled to a QP2010 GC-MS (Shimadzu, Japan). Three mg of finely ground biomass material (2 mm maximum) from each sample was weighed into a deactivated stainless steel cup. Each sample was introduced by gravity into the pyrolyzer set at 550° C. The interface between the pyrolyzer and GC inlet was set at 300° C. Separation of pyrolysates was performed on a GC-column (VF-5MS, 30M×0.25 mm×0.25 um). Helium flow through the pyrolyzer and column was set at 450 mL/min and 1.0 mL/min respectively. The inlet split ratio was 350:1. The column temperature program was initially set at 70° C. (held for 4 minutes) at a ramp rate of 20° C./min to a final temperature of 350° C. Mass spectral acquisition was at 3333 amu/sec from 50 amu-300 amu after a 4.5 min delay.

The areas of the peaks corresponding to different lignin units and to levoglucosan and furfural (both as cellulose markers) were collected. Methylstearate was used as an internal standard to quantify the amount of each component and thus quantitatively determine the amount of H, G, and S present in the sample. Total lignin was calculated as the sum of H, G, and S.

The pyrolysis GC-MS data and NIR spectral data were used to develop and validate NIR models for H, G, S, and total lignin amounts in switchgrass, *Arabidopsis*, and sorghum. The $R^2$ and RMSECV values for measured versus predicted H, G, S, and/or total lignin content are shown in Table 11. The significant positive correlations between the measured values and those predicted by the models indicate that NIR models can be developed for H, G, S, and total lignin amounts in other types of biomass and other plant species.

TABLE 11

| Plant Species | Component | $R^2$ | RMSECV |
|---|---|---|---|
| Switchgrass | H Lignin | 0.61 | 0.408 |
| | G Lignin | 0.81 | 0.487 |
| | S Lignin | 0.91 | 0.0591 |
| | Total Lignin | —* | — |
| *Arabidopsis* | H Lignin | 0.78 | 0.347 |
| | G Lignin | 0.78 | 0.763 |
| | S Lignin | 0.70 | 0.133 |
| | Total Lignin | 0.79 | 1.13 |
| *Sorghum* | H Lignin | — | — |
| | G Lignin | 0.77 | 0.886 |
| | S Lignin | 0.90 | 0.22 |
| | Total Lignin | 0.81 | 1.86 |

*— = Not Determined

Example 13

NIR Model for Ferulate Content

Extractives-free biomass samples were obtained as follows. One gram of a biomass sample, prepared as described in Example 1, was extracted with 70 mL water and 70 mL ethanol for 15 minutes each at 70° C. to remove extractives. The solids remaining after removal of the solvent were oven dried at 45° C. and stored in a dessicator.

NIR spectra were collected from each of ten extractives-free switchgrass samples. Fifty mg of each sample was extracted with 1.5 mL of 2M KOH at 80° C. for 10 minutes using a microwave assisted extractor. The extract was removed and solids discarded. Each extract, dark brown in color, was neutralized with 500 microliters of 4M HCl, which turned each extract pale yellow in color. Each extract was dried in a vacuum dryer with a cryogenic trap, resuspended in 1.0 mL of methanol, sonicated to facilitate resuspension, and filtered to remove particulates. The resulting solution had a clear golden color.

Five hundred microliters of each filtered solution was transferred to a LC-MS vial, along with 200 ul of a 1 mg/mL sinapinic acid standard (50/50 methanol:water). Added to the vial was 300 uL of water. Separation of ferulic acid was performed on a Agilent 1200 mass spectrometer coupled to a Unique ToF using a Phenonmenex Synergi Max-RP (150×4.6 mm) and a gradient elution profile from 10% Methanol with 1% Acetic Acid to 90%. The time of flight mass spec acquisition was set at 4 spectra/sec with a range of 50-500 m/z. The ferulate content in each sample was calculated.

The MS data and NIR spectral data were used to develop and validate a NIR model for ferulate content in switchgrass. The cross validation results indicated that the $R^2$ value for measured versus predicted ferulate content was 0.95 with a RMSECV of 0.26. The good correlation between the measured values and those predicted by the model indicates that NIR models can be developed for ferulate content for other types of biomass and other plant species.

Example 14

Analysis of Upland and Lowland Switchgrass Varieties

An expanded NIR model for switchgrass composition and glucose conversion efficiency was developed and validated as described for the SWG_2 model. The expanded model was designated the SWG_5 model. Three upland varieties and three lowland varieties were grown at a single location in Illinois. The SWG_5 model was used to predict extractives-free glucan content and glucose conversion efficiency of each variety. The data showed that upland and lowland varieties can be distinguished based on their extractives-free glucan content and glucose conversion efficiency.

Example 15

Sorghum Model Development and Validation

Biomass samples were prepared as described in Example 1 from 30 sorghum samples. NIR spectra were collected from each sample prior to further processing as described in Example 1.

The composition of the 30 sorghum samples was determined using methods as described in Example 2. Starch was measured following the DOE/EERE method *Determination of Starch in Biomass.*

Twenty four of the biomass samples were subjected to acid pretreatment and enzymatic saccharification as described in Example 4 except that the acid pretreatment conditions were 0.6 wt % acid in the liquid phase of the vessel and the microwave system was set to 180° C. Total glucose released per gram dry biomass was measured as well as the theoretical glucose yield, as described in Example 4. In addition, the amount of recalcitrant glucan in weight percent was measured.

The total glucose released, the theoretical glucose yield and the amount of recalcitrant glucan were used to develop and validate NIR conversion models for sorghum. The models were generated using Opus software as described in Example 1. NIR models were developed using the multivariate analysis software integrated into the OPUS software. Models for analysis of sorghum composition used a wavelength range of 8000-3800 $cm^{-1}$. Math treatments used were first derivative and vector normalization with 17 smoothing points.

The model for theoretical glucose yield utilized five principle components, the model for recalcitrant glucan utilized four principle components and the model for total glucose released utilized five principle components. The cross validation results indicated that the $R^2$ value for measured versus predicted theoretical glucose yield was 0.92, with a RMSECV of 2.45. The $R^2$ value for measured versus predicted recalcitrant glucan was 0.92, with a RMSECV of 1.01. The $R^2$ value for measured versus predicted total glucose released was 0.86, with a RMSECV of 9.4. The good correlation between the measured values and those predicted by the models indicates that various other NIR models can be developed for sorghum.

Near infrared spectral data were acquired from the same 30 sorghum samples using a Foss XDS Rapid content analyzer (Foss North America, Eden Prairie, Minn.), running WinISI 4.0 software according to the manufacturer's protocols.

A Foss RCA solids transport module with a coarse granular sample cell was used to obtain spectra of all samples. The instrument is equipped with a standard reflectance detector array including two silicon detectors to monitor visible light from 400-850 nm and four lead-sulfide detectors to monitor NIR light from 850-2500 nm. The Foss instrument has a maximum resolution of 1 nm. To minimize the effect of water in the biomass spectra, each sample was air dried to less than 10% moisture prior to NIR analysis. Spectral information was collected from 400-2500 nm (25000 cm$^{-1}$ to 4000 cm$^{-1}$) with a resolution of 1 nm. For each spectroscopic sample, a total of 64 spectra were collected and averaged to compensate for sample heterogeneity. Each calibration sample was sub-sampled three times and the sub-sample spectra were averaged. Final averaged spectra were used in the method calibration. These spectroscopic techniques enabled a high quality, reproducible NIR reflectance spectrum to be obtained for each of the calibration samples. Instrument reproducibility tests indicated that the reproducibility limits of the NIR spectrometer contributed less than 0.2% to the absolute prediction errors in NIR/PLS models.

NIR models were developed using the multivariate analysis software integrated into the WinISI software. Models for analysis of sorghum composition used a wavelength range of 400-2500 nm. Math treatments used were first derivative followed by a standard normal variate scatter correction and detrend baseline adjustment with a first order polynomial, 4 nm block, and 4 nm gap.

Cross validation results for NIR models of various biomass components using the Bruker instrument and the Foss instrument are shown in Table 12. The good correlations between the measured values and those predicted by the models indicate that NIR models can be developed using different instruments and software programs. The good correlations also indicate that various other NIR models can be developed for sorghum.

TABLE 12

| Component | Bruker OPUS | | | Foss WinISI | | |
| --- | --- | --- | --- | --- | --- | --- |
| | $R^2$ | SECV | PCs | $R^2$ | SECV | PCs |
| Glucan | 0.923 | 2.1 | 5 | 0.969 | 2.5 | 4 |
| Xylan | 0.858 | 1.0 | 3 | 0.949 | 0.9 | 3 |
| Lignin | 0.861 | 1.2 | 3 | 0.954 | 0.9 | 3 |
| Protein | 0.800 | 0.4 | 7 | 0.951 | 0.3 | 3 |
| Ash | 0.869 | 0.8 | 4 | 0.658 | 0.6 | 2 |
| Starch | 0.547 | 0.4 | 4 | 0.976 | 0.8 | 3 |
| Extractives | 0.925 | 1.2 | 4 | 0.992 | 1.2 | 7 |
| Sucrose | 0.978 | 1.0 | 4 | 0.997 | 1.0 | 6 |
| Acetyl | 0.483 | 1.4 | 3 | 0.875 | 0.2 | 2 |

Example 16

Thermochemical Processing of Biomass

Biomass samples were collected from eleven different switchgrass plants from diverse geographic locales in the United States, and prepared as described in Example 1. An FT-NIR spectrum was acquired as described in Example 1 and the composition of each sample was predicted using the SWG_2 model. The results are shown in Tables 13 and 14.

TABLE 13

Amounts of Various Components in Switchgrass Samples

| Plant | Arabinan | Ash | Extractives | Glucan | Lignin | Protein | Sucrose | Xylan | Total |
| --- | --- | --- | --- | --- | --- | --- | --- | --- | --- |
| 2439 079 | 9.0 | 3.4 | 4.6 | 37.8 | 21.9 | 1.4 | 0.7 | 24.8 | 103.5 |
| 2439 118 | 5.9 | 2.1 | 7.2 | 37.3 | 20.7 | 1.1 | 4.0 | 21.9 | 100.2 |
| 2439 204 | 7.0 | 3.2 | 7.5 | 33.9 | 19.3 | 1.0 | 1.3 | 20.6 | 93.8 |
| 2439 471 | 7.8 | 5.2 | 7.7 | 32.3 | 18.8 | 1.2 | 0.3 | 23.1 | 96.4 |
| 2439 507 | 9.5 | 8.1 | 5.8 | 32.0 | 19.4 | 1.6 | 1.3 | 25.0 | 102.6 |
| 2439 613 | 8.2 | 4.9 | 6.1 | 33.7 | 19.8 | 1.1 | 1.4 | 23.0 | 98.2 |
| 2439_520 | 8.0 | 7.8 | 7.4 | 27.6 | 16.7 | 0.6 | 0.8 | 20.0 | 88.7 |
| 7000 000 | 3.8 | 4.2 | 9.4 | 31.9 | 17.5 | 5.6 | 3.8 | 21.0 | 97.2 |
| 7000 005 | 3.2 | 4.3 | 11.8 | 31.5 | 17.3 | 3.9 | 2.2 | 21.4 | 95.6 |
| 7000 484 | 6.2 | 1.1 | 7.3 | 40.7 | 22.4 | 2.4 | 1.0 | 21.5 | 102.5 |
| 7000 487 | 6.5 | 1.6 | 7.8 | 40.2 | 22.4 | 2.2 | −0.6 | 21.9 | 101.9 |

TABLE 14

Range in Various Components in Switchgrass Samples

| | Arabinan | Ash | Extractives | Glucan | Lignin | Protein | Sucrose | Xylan |
| --- | --- | --- | --- | --- | --- | --- | --- | --- |
| Min | 3.2 | 1.1 | 4.6 | 27.6 | 16.7 | 0.6 | −0.6 | 20.0 |
| Max | 9.5 | 8.1 | 11.8 | 40.7 | 22.4 | 5.6 | 4.0 | 25.0 |
| Mean | 6.6 | 4.2 | 7.8 | 34.1 | 19.4 | 2.1 | 1.5 | 21.9 |
| Std Dev | 2.0 | 2.3 | 1.9 | 4.1 | 2.0 | 1.5 | 1.4 | 1.6 |

An elemental analysis for carbon, hydrogen, nitrogen, oxygen and sulfur was carried out on some of the biomass samples above as well as biomass samples from one additional plant. In addition, the amounts of ash, volatile matter and fixed carbon were determined using the methods shown in Table 15. The results from these wet chemistry techniques are shown in Tables 16 and 17.

TABLE 15

Standard ASTM methods for thermochemical analysis (ASTM 2007)

| Determination | Method |
|---|---|
| Ultimate | ASTM D3176 |
| Proximate | ASTM D3172 |
| Moisture | ASTM D3173 |
| C, H, N | ASTM D5373 |
| Sulfur | ASTM D4239 |
| Oxygen | ASTM D5622 |
| Ash | ASTM D3174 |
| Volatile matter | ASTM D3175 |
| HHV | ASTM D5865 |

TABLE 16

Elemental Composition of Switchgrass Samples*

| Plant | C | H | N | O | S | Ash | Volatile Matter | Fixed Carbon |
|---|---|---|---|---|---|---|---|---|
| 2439 079 | 47.09 | 6.53 | 0.23 | 49.01 | 0.05 | 4.02 | 78.40 | 17.58 |
| 2439 118 | 46.93 | 6.55 | 0.26 | 49.20 | 0.05 | 4.03 | 78.16 | 17.81 |
| 2439 204 | 46.64 | 6.57 | 0.32 | 48.33 | 0.05 | 4.52 | 78.50 | 16.98 |
| 2439 471 | 45.67 | 6.47 | 0.27 | 48.04 | 0.08 | 6.48 | 77.79 | 15.73 |
| 2439 507 | 45.68 | 6.47 | 0.26 | 47.48 | N.D. | 7.73 | 76.59 | 15.68 |
| 2439 613 | 46.76 | 6.37 | 0.25 | 47.24 | 0.05 | 5.26 | 77.37 | 17.37 |
| 2439_520 | 45.29 | 6.42 | 0.33 | 47.44 | 0.05 | 7.38 | 76.66 | 15.96 |
| 7000 000 | 46.91 | 6.75 | 1.11 | 46.82 | 0.12 | 4.68 | 75.80 | 19.52 |
| 7000 005 | 46.21 | 6.64 | 0.97 | 46.23 | 0.10 | 5.42 | 74.87 | 19.71 |
| 7000 484 | 48.01 | 6.74 | 0.49 | 48.76 | 0.08 | 2.84 | 76.62 | 20.54 |
| 7000 488 | 44.16 | 6.29 | 0.84 | 46.25 | 0.09 | 12.07 | 71.84 | 16.09 |

*Values are expressed as percent dry weight

TABLE 17

Range in Elemental Amounts in Switchgrass Samples*

| | Carbon | Hydrogen | Nitrogen | Oxygen | Sulfur | Ash | Volatile Matter | Fixed Carbon |
|---|---|---|---|---|---|---|---|---|
| Min | 44.16 | 6.29 | 0.23 | 46.23 | 0.05 | 2.84 | 71.84 | 15.68 |
| Max | 48.01 | 6.75 | 1.11 | 49.20 | 0.12 | 12.07 | 78.50 | 20.62 |
| Mean | 46.30 | 6.52 | 0.53 | 47.65 | 0.08 | 5.81 | 76.39 | 17.80 |
| Std Dev | 1.00 | 0.14 | 0.35 | 1.02 | 0.02 | 2.42 | 1.98 | 1.86 |

*Values are expressed as percent dry weight.

The HHV for each sample was determined by the wet chemistry techniques described in ASTM D5865, Standard Test Method for Determination of Higher Heating Value in Coal. The results are shown in Table 18.

TABLE 18

HHV of Switchgrass Samples

| Plant | HHV* |
|---|---|
| 2439 079 | 8045.16 |
| 2439 118 | 8031.80 |
| 2439 204 | 7968.95 |
| 2439 471 | 7854.22 |
| 2439 507 | 7834.56 |
| 2439 613 | 7988.43 |
| 2439_520 | 7816.57 |
| 7000 000 | 8166.72 |
| 7000 005 | 8020.21 |
| 7000 484 | 8160.44 |
| 7000 488 | 7508.44 |
| Min | 7508.44 |
| Max | 8166.72 |
| Mean | 7946.69 |
| Std Dev | 178.16 |

*Values are expressed as BTU per pound biomass

The results indicate that the HHV varies about 10% among samples. The results also indicate that the range in fixed carbon amounts among the samples varied about 25%, and that there is not a strong relationship between elemental analysis and fixed carbon.

Example 17

Thermochemical Model Development and Validation

One hundred and twenty-four switchgrass samples were prepared and NIR spectra were collected from each sample as described in Example 1. NIR spectra were collected from each of the samples prior to further processing. The higher heating value, C, H, N, O, and volatile matter of each sample were determined using the ASTM standard methods listed in Example 16.

The thermochemical data and NIR spectral data were used to develop and validate NIR models for HHV, C, H, N, O, and volatile matter in switchgrass. The $R^2$ and RMSECV values for measured versus predicted HHV, C, H, N, O, and volatile matter are shown in Table 19. The significant positive correlations between the measured values and those predicted by the models indicate that NIR models can be developed for HHV, C, H, N, O, fixed carbon and volatile matter in other types of biomass and other plant species.

TABLE 19

| Component (PC) | $R^2$ | RMSECV |
|---|---|---|
| Nitrogen (5) | 0.964 | 0.1 |
| Carbon (9) | 0.719 | 0.4 |
| Volatile Carbon (6) | 0.813 | 1.0 |

TABLE 19-continued

| Component (PC) | R² | RMSECV |
|---|---|---|
| Hydrogen (4) | 0.681 | 0.7 |
| Oxygen (6) | 0.708 | 0.6 |
| HHV (5) | 0.696 | 69.2 |

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of using a NIR model to predict the amount of accessible carbohydrate material in a feedstock sample, comprising:
   a) collecting NIR spectral data from a test feedstock sample;
   b) applying, to said spectral data, a NIR model of accessible carbohydrate calibrated for feedstocks of the same type as said sample, wherein said NIR model is formulated by: i) subjecting a set of biomass calibration feedstock samples to near infrared spectroscopy to produce NIR spectroscopic data from each said sample, each said calibration sample of the same type of feedstock as said test sample; ii) measuring the chemical compositions of each said calibration feedstock sample by wet chemical techniques; iii) measuring the total amount of monosaccharides and disaccharides solubilized by each said calibration feedstock sample after processing under a defined pretreatment condition or defined enzyme load condition; and iv) generating said calibrated NIR model for predicting the amount of accessible carbohydrate in said test feedstock sample processed under said defined pretreatment condition or defined enzyme load condition, from said spectroscopic data, said chemical compositions, and said solubilized mono and disaccharide amounts; and
   c) predicting the amount of accessible carbohydrate material in said test feedstock sample, based on the results of said applying step, wherein steps b) and c) are performed on a suitably programmed computer.

2. The method of claim 1, wherein said generating step comprises regressing said spectral data against said chemical composition data and said monosaccharide and disaccharide amounts.

3. The method of claim 1, wherein said defined condition is a defined pretreatment condition.

4. The method of claim 1, wherein said defined condition is a defined enzyme load condition.

5. The method of claim 1, wherein: step iii) comprises measuring the total amount of monosaccharides and disaccharides solubilized by each said calibration feedstock sample after processing under a defined pretreatment condition and a defined enzyme load condition; and step iv) comprises generating said calibrated NIR model for predicting the amount of accessible carbohydrate in said test feedstock sample processed under said defined pretreatment condition and defined enzyme load condition, from said spectroscopic data, said chemical compositions, and said solubilized mono and disaccharide amounts.

6. The method of claim 1, wherein said test feedstock sample comprises biomass from a species selected from the group consisting of switchgrass, sorghum, sugarcane, miscanthus, poplar, willow, rice, wheat and corn.

7. The method of claim 6, wherein said test feedstock sample comprises biomass from sorghum.

8. The method of claim 6, wherein said test feedstock sample comprises biomass from sugarcane.

9. The method of claim 6, wherein said test feedstock sample comprises biomass from switchgrass.

10. The method of claim 6, wherein said test feedstock sample comprises biomass from corn.

11. The method of claim 6, wherein said test feedstock sample comprises biomass from wheat.

12. The method of claim 1, wherein said NIR model is further for predicting the saccharification efficiency of said test feedstock sample.

13. The method of claim 1, wherein said NIR model is further for predicting the product yield of said test feedstock sample.

14. The method of claim 13, wherein said product yield is ethanol yield.

15. The method of claim 14, wherein said test feedstock sample comprises sorghum, switchgrass or wheat.

* * * * *

UNITED STATES PATENT AND TRADEMARK OFFICE
CERTIFICATE OF CORRECTION

| | | Page 1 of 1 |
|---|---|---|
| PATENT NO. | : 8,489,340 B2 | |
| APPLICATION NO. | : 12/740941 | |
| DATED | : July 16, 2013 | |
| INVENTOR(S) | : Hames et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 116 days.

Signed and Sealed this
Third Day of February, 2015

Michelle K. Lee
*Deputy Director of the United States Patent and Trademark Office*